(12) United States Patent
Carson et al.

(10) Patent No.: US 7,358,261 B2
(45) Date of Patent: Apr. 15, 2008

(54) HETEROARYL ALKYLAMIDE DERIVATIVES USEFUL AS BRADYKININ RECEPTOR MODULATORS

(75) Inventors: John R. Carson, Norristown, PA (US); Michele C. Jetter, Norristown, PA (US); Jung S. Lee, Ambler, PA (US); Mark A. Youngman, Warminster, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 101 days.

(21) Appl. No.: 11/014,471

(22) Filed: Dec. 16, 2004

(65) Prior Publication Data

US 2005/0159443 A1 Jul. 21, 2005

Related U.S. Application Data

(62) Division of application No. 10/403,186, filed on Mar. 31, 2003, now Pat. No. 6,958,349.

(60) Provisional application No. 60/371,350, filed on Apr. 10, 2002.

(51) Int. Cl.
*A61K 31/47* (2006.01)
*C07D 215/38* (2006.01)

(52) U.S. Cl. .................. 514/311; 514/312; 514/314; 546/153; 546/176; 546/178

(58) Field of Classification Search ................ 514/311, 514/312, 314; 546/153, 176, 178
See application file for complete search history.

(56) References Cited

U.S. PATENT DOCUMENTS

| | | | | |
|---|---|---|---|---|
| 5,750,699 A | * | 5/1998 | Oku et al. ................... | 546/121 |
| 6,008,229 A | * | 12/1999 | Oku et al. ................... | 514/311 |
| 6,100,284 A | * | 8/2000 | Oku et al. ................... | 514/394 |
| 6,344,462 B1 | * | 2/2002 | Oku et al. ................... | 514/300 |

FOREIGN PATENT DOCUMENTS

EP    0 596 406 A1 *    5/1994

OTHER PUBLICATIONS

Steranka, Proc. Natl. Acad. Sci, USA, vol. 85, pp. 3245-3249, May 1988, Neurobiology.*

* cited by examiner

*Primary Examiner*—D. Margaret Seaman
(74) *Attorney, Agent, or Firm*—John Harbour

(57) ABSTRACT

This invention is directed towards novel alkylamide derivatives as bradykinin receptor antagonists useful for the treatment of bradykinin modulated disorders such as pain, inflammation, asthma and allergy. Furthermore, the present invention is directed to novel alkylamide derivatives as bradykinin receptor agonists useful for the treatment of bradykinin modulated disorders such as hypertension and the like.

10 Claims, No Drawings

HETEROARYL ALKYLAMIDE DERIVATIVES USEFUL AS BRADYKININ RECEPTOR MODULATORS

This application is a divisional of application Ser. No. 10/403,186, filed on Mar. 31, 2003 now U.S. Pat. No. 6,958,349 and claims priority of provisional application No. 60/371,350, filed on Apr. 10, 2002. The complete disclosures of the aforementioned related U.S. patent applications are hereby incorporated herein by reference for all purposes.

FIELD OF THE INVENTION

The present invention is directed to novel bradykinin ($BK_2$) receptor modulators, pharmaceutical compositions containing them and their use in the treatment of bradykinin (BK) modulated disorders. More particularly, the present invention is directed to novel alkylamide derivatives as bradykinin receptor antagonists useful for the treatment of bradykinin modulated disorders such as pain, inflammation, asthma and allergy. Furthermore, the present invention is directed to novel alkylamide derivatives as bradykinin receptor agonists useful for the treatment of bradykinin modulated disorders such as hypertension and the like.

BACKGROUND OF THE INVENTION

Bradykinin is an endogenous nonapeptide which is thought to play an important role in a variety of inflammatory diseases and pain. Bradykinin (BK) and the decapeptide kallidin are released from plasma and tissue protein kininogens by the proteolytic action of kallikreins. Kinins are also produced during acute inflammation following the release of cellular proteases from immune cells. Rapid degradation of bradykinin and kallidin occurs through kininase activity to yield several active and inactive metabolites such as des-$Arg^9$-bradykinin and des-$Arg^{10}$-kallidin (Bhoola K et al. *Pharmacology Reviews* 1992, 44, 1-80).

Bradykinin itself has been shown to induce pain by direct stimulation of nociceptors (C and Aδ fibers) which innervate most tissues such as skin, joint and muscle. These sensory fibers then become sensitized to various physical and chemical stimuli. Bradykinin may sensitize fibers by synergistic interactions with other inflammatory agents such as prostaglandins or by the release of histamine from mast cells (Nicol G and Cui M *J. Physiol.* 1994, 480, 485-92).

In mammals, the biological effects of kinins are mediated through two distinct bradykinin receptor subtypes, $B_1$ and $B_2$. Both $B_1$ and $B_2$ receptors are members of the superfamily of G-protein coupled receptors (Dray A. and Perkins M. *Trends in Neurosciences* 1993, 16, 99-104). Bradykinin $B_2$ receptors have high affinity for bradykinin and kallidin and are constitutively expressed in contrast to bradykinin $B_1$ receptors which are inducible. $B_2$ receptors are largely distributed in peripheral and central tissues and are present in neurons, endothelial cells, epithelial cells and fibroblasts. Both $B_1$ and $B_2$ receptors have been cloned in many animal species as well as human.

Many of the physiological actions of kinins seem to be mediated by stimulation of the constitutive BK $B_2$ receptor. Because of the important role that kinins are believed to play in a variety of inflammatory diseases and pain, researchers have pursued antagonists for the kinin receptors for years. Potent and selective peptide antagonists, specific for the $B_2$ receptor, were discovered and evaluated in the clinic (Hock et al, *British Journal of Pharmacology* 1991, 102, 769; Cheronis et al, *Journal of Medicinal Chemistry* 1992, 35, 1563). Data collected with these antagonists supported the idea that an increase in endogenous kinins may be involved in inflammation, pain and tissue injury. These non-peptide $BK_2$ antagonists also allowed researchers to further investigate the role that kinins play in vascular disease states such as arteriosclerosis (Hoechst A G, EP-007977997 (1997)).

In 1993, Sterling-Winthrop published their findings on a nbn-peptide bradykinin $B_2$ receptor antagonist, WIN 64338 (Salvino J, Seoane P. and Douty B. *Journal of Medicinal Chemistry* 1993, 36, 2583). There were a number of drawbacks to this series of compounds including low specificity and a species-dependent variable affinity for kinin receptors.

Recently several novel classes of non-peptide bradykinin $B_2$ receptor antagonists were disclosed by Fujisawa (Oku T, Kayakiri H, Satoh S, Abe Y and Tanaka H EP 596406 (1994); Oku T, Kayakiri H, Satoh S, Abe Y and Tanaka H EP 622361 (1994); Inamura N, Asano M and Hatori C et al. *European Journal of Pharmacology* 1997, 333, 79; Asano M, Inamura N And Hatori C et al. *British Journal of Pharmacology* 1997, 120, 617.) These compounds possess high affinity and specificity for the bradykinin $B_2$ receptor. They were also shown to exhibit in vivo functional antagonist activity. (Abe Y, Kayakiri H and Satoh S et al *Journal of Medicinal Chemistry* 1998, 41, 564; Abe Y, Kayakiri H and Satoh S et al *Journal of Medicinal Chemistry* 1998, 41, 4053; Abe Y, Kayakiri H and Satoh S et al *Journal of Medicinal Chemistry* 1998, 41, 4062; Abe Y, Kayakiri H and Satoh S et al *Journal of Medicinal Chemistry* 1998, 41, 4587).

In PCT publication WO 97/41104 and U.S. Pat. No. 6,083,959, Oku, T. et al disclosed bradykinin modulating compounds of the formula:

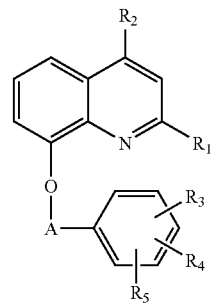

wherein:

$R_1$ is lower alkyl, $R_2$ is hydrogen, lower alkyl or a heterocyclic group, $R_3$ is hydrogen, lower alkyl or halogen, $R_4$ is lower alkyl or halogen, $R_5$ is nitro or amino substituted with substituent(s) selected from the group consisting of lower alkyl and acyl, and A is lower alkylene, provided that $R_3$ and $R_4$ are each lower alkyl when $R_2$ is hydrogen or lower alkyl.

The acyl group of $R_5$ is further defined as including optionally substituted heterocyclic(lower)alkanoyl moieties, in which the term heterocyclic includes unsaturated 3- to 8-membered, preferably 5- or 6-membered heteromonocyclic group containing 1 to 4 nitrogen atoms or a sulfur atom.

Oku T, Kayakiri H, Abe Y, Sawada Y and Mizutani T, in PCT publication WO 97/11069 disclosed bradykinin modulating compounds of formula:

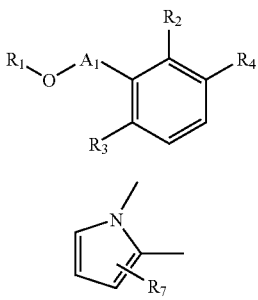

wherein:
A₁ is lower alkylene,
R₁ is substituted quinolyl, etc.,
R₂ is hydrogen, halogen or lower alkyl, and
R₄ is a group of the formula -Q-A₂-R₅, etc. in which
  R₅ is amino, acylamino, etc.,
  A₂ is lower alkylene or a single bond, and
  Q is a group of formula (a), etc.

In U.S. Pat. No. 5,574,042, Oku, T et al disclosed imidazo[1,2-a]pyridines having the formula:

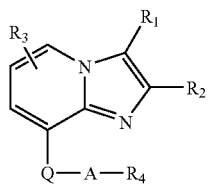

wherein:
R₁ is halogen,
R₂ and R₃ are each hydrogen, lower alkyl, halo(lower)alkyl or acyl,
R₄ is aryl having suitable substituent(s), or a heterocyclic group optionally having suitable substituent(s),
Q is O or N—R₁₁, in which R₁₁ is hydrogen or acyl, and
A is lower alkylene.

The suitable substituents on the aryl group of R₄ are further defined as including acyl groups, which is further defined to include optionally substituted heterocyclic(lower)alkanoyl moieties, in which the term heterocyclic includes unsaturated 3- to 8-membered, preferably 5- or 6-membered heteromonocyclic group containing 1 to 4 nitrogen atoms or a sulfur atom.

In PCT publication WO 96/13485, Oku, T. et al disclose pyridopyrimidones, quinolines and fused N-heterocyclic compounds as bradykinin modulators.

A number of derivatives that are structurally related to the Fujisawa compounds have been disclosed by Fournier (Dodey P, Bondoux M, Pruneau D et al. WO 96 40639 (1996); Dodey P, Bondoux M et al. WO 97 07115 (1997); WO 97 24349 (1997); WO 98 03503 (1998) and also by Hoechst (Heitsch H, Wagner A, Wirth K et al. EP 795547 (1997); EP 796848, EP 835659(1998).

Compounds of the present invention have not been previously disclosed or enabled.

It is expected that bradykinin receptor antagonists may be useful in the treatment and prevention of various mammalian disease states, for example pain, inflammatory joint disease, inflammatory bowel disease, allergy, asthma, rhinitis, brain edema and trauma, tissue injury, septic shock, acute pancreatitis, post-operative pain and migraine. It is also expected that bradykinin receptor agonists may be useful in the treatment and prevention of other disease states such as hypertension and the like.

It is an object of the present invention to provide bradykinin (B₂) receptor modulators. It is a further object of the invention to provide bradykinin antagonists and bradykinin agonists. It is an object of the present invention to provide a method of treating or ameliorating a condition mediated by the bradykinin receptor. It is an object of the invention to provide a useful pharmaceutical composition comprising a compound of the present invention useful as bradykinin modulators.

SUMMARY OF THE INVENTION

The present invention provides bradykinin receptor modulators of Formula (I):

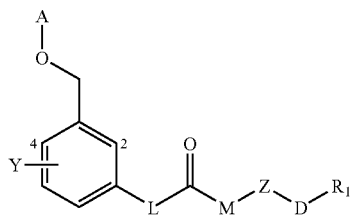

Formula (I)

wherein:
A is selected from a group consisting of:

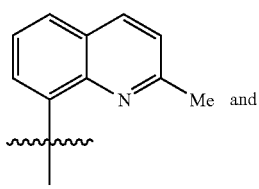

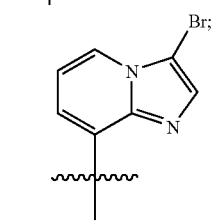

Y is one to three substituents independently selected from the group consisting of halogen and $C_{1-8}$alkyl;
L is selected from the group consisting of:

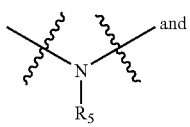

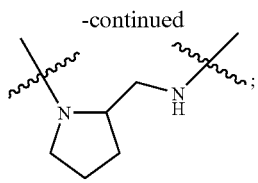

in which $R_5$ is selected from the group consisting of hydrogen, $C_{1-8}$alkyl, $C_{2-8}$alkenyl and aryl($C_{1-8}$)alkyl wherein aryl is optionally substituted with one or more substituents independently selected from the group consisting of $C_{1-8}$alkyl, $C_{1-8}$alkoxy, [($C_{1-8}$)alkyl]$_2$N—, halogen, and cyano;

M is selected from the group consisting of $C_{1-8}$alkylene and $C_{2-8}$alkenylene;

Z is selected from the group consisting of thienylene, (N—$R_6$)pyrrolylene or pyridinylene, each optionally substituted with one or two $C_{1-4}$alkyl substituents; provided that when Z is pyridinylene, then L can only be

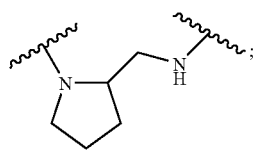

$R_6$ is independently selected from the group consisting of $C_{1-8}$alkyl, $C_{2-8}$alkenyl, $C_{3-8}$cycloalkyl($C_{1-8}$)alkyl and aryl ($C_{1-8}$)alkyl wherein aryl is optionally substituted with one or more substituents independently selected from the group consisting of $C_{1-8}$alkyl, $C_{1-8}$alkoxy, [($C_{1-8}$)alkyl]$_2$N—, halogen, and cyano;

D is selected from the group consisting of —C(O)—, —NH—C(O)—, and phenylene;

$R_1$ is selected from the group $C_{1-8}$alkyl, $C_{2-8}$alkenyl, $C_{1-8}$alkoxy, cyano, [($C_{1-8}$)alkyl]$_2$aminoaryl, aryl($C_{1-8}$) alkyl, aryl($C_{1-8}$)alkenyl, $C_{3-8}$cycloalkyl, ($C_{1-8}$)alkylamino ($C_{1-8}$)alkyl, [($C_{1-8}$)alkyl]$_2$amino($C_{1-8}$)alkyl, ($R_7$)aryl, ($R_8$)heteroaryl, ($R_9$)heteroaryl($C_{1-8}$)alkyl, ($R_{10}$)heterocyclyl($C_{1-8}$)alkyl and [($R_{11}$)heteroaryl][($C_{1-8}$)alkyl]amino ($C_{1-8}$)alkyl;

$R_7$ is one or two substituents independently selected from the group consisting of hydrogen, $C_{1-8}$alkyl, $C_{2-8}$alkenyl, $C_{2-8}$alkynyl, $C_{3-8}$cycloalkyl, aryl($C_{1-8}$)alkyl, $C_{1-8}$alkoxy, aryloxy, aryl($C_{1-8}$)alkoxy, $C_{1-8}$alkylthio, trifluoro($C_{1-8}$) alkyl, trifluoro($C_{1-8}$)alkoxy, heterocyclyl($C_{1-8}$)alkyl, methylenedioxy, amino, —NH($C_{1-8}$)alkyl, —N[($C_{1-8}$) alkyl]$_2$, —NH(aryl), —N(aryl)$_2$, —NH($C_{1-8}$)alkylaryl, —N[($C_{1-8}$)alkylaryl]$_2$, —CO$_2$($C_{1-8}$)alkyl, —CO$_2$(aryl), —C(O)NH$_2$, —C(O)NH($C_{1-8}$)alkyl, —C(O)N[($C_{1-8}$) alkyl]$_2$, —NHC(O)($C_{1-8}$)alkyl, ($C_{1-8}$alkyl)$_2$—N—($C_{1-8}$) alkyl, S(O)($C_{1-8}$)alkyl, —SO$_2$($C_{1-8}$)alkyl, —SO$_2$NH$_2$, —SO$_2$NH($C_{1-8}$)alkyl, —SO$_2$N[($C_{1-8}$)alkyl]$_2$, —C(O) ($C_{1-8}$)alkyl, —C(O)aryl, —C(O)($C_{1-8}$)alkylaryl, halogen, hydroxy, cyano, nitro, phenyl, a 5-membered monocyclic aromatic ring containing one O, S, or N atom and up to three additional N atoms, a 6-membered monocyclic aromatic ring containing at least one N atom and up to two additional N atoms, and a partially saturated or unsaturated 5- or 6-membered monocyclic ring having one O, S or N atom which optionally contains up to one additional O, S or N atom;

$R_8$ is one or two substituents independently selected from the group consisting of hydrogen, $C_{1-8}$alkyl, $C_{2-8}$alkenyl, $C_{2-8}$alkynyl, $C_{3-8}$cycloalkyl, aryl($C_{1-8}$)alkyl, $C_{1-8}$alkoxy, aryloxy, aryl($C_{1-8}$)alkoxy, $C_{1-8}$alkylthio, trifluoro($C_{1-8}$) alkyl, trifluoro($C_{1-8}$)alkoxy, heterocyclyl($C_{1-6}$)alkyl amino, —NH($C_{1-8}$)alkyl, —N[($C_{1-8}$)alkyl]$_2$, —NH(aryl), —N(aryl)$_2$, —NH($C_{1-8}$)alkylaryl, —N[($C_{1-8}$)alkylaryl]$_2$, —CO$_2$($C_{1-8}$)alkyl, —CO$_2$(aryl), —C(O)NH$_2$, —C(O)NH ($C_{1-8}$)alkyl, —C(O)N[($C_{1-8}$)alkyl]$_2$, —NHC(O)($C_{1-8}$) alkyl, ($C_{1-8}$alkyl)$_2$—N—($C_{1-8}$)alkyl, S(O)($C_{1-8}$)alkyl, —SO$_2$($C_{1-8}$)alkyl, —SO$_2$NH$_2$, —SO$_2$NH($C_{1-8}$)alkyl, —SO$_2$N[($C_{1-8}$)alkyl]$_2$, —C(O)($C_{1-8}$)alkyl, —C(O)aryl, —C(O)($C_{1-8}$)alkylaryl, halogen, hydroxy, cyano, nitro, phenyl, a 5-membered monocyclic aromatic ring containing one O, S, or N atom and up to three additional N atoms, a 6-membered monocyclic aromatic ring containing at least one N atom and up to two additional N atoms, and a partially saturated or unsaturated 5- or 6-membered monocyclic ring having one O, S or N atom which optionally contains up to one additional O, S or N atom;

$R_9$ is one or two substituents independently selected from the group consisting of hydrogen, $C_{1-8}$alkyl, $C_{2-8}$alkenyl, $C_{2-8}$alkynyl, $C_{3-8}$cycloalkyl, aryl($C_{1-8}$)alkyl, $C_{1-8}$alkoxy, aryloxy, aryl($C_{1-8}$)alkoxy, $C_{1-8}$alkylthio, trifluoro($C_{1-8}$) alkyl, trifluoro($C_{1-8}$)alkoxy, heterocyclyl($C_{1-6}$)alkyl amino, —NH($C_{1-8}$)alkyl, —N[($C_{1-8}$)alkyl]$_2$, —NH(aryl), —N(aryl)$_2$, —NH($C_{1-8}$)alkylaryl, —N[($C_{1-8}$)alkylaryl]$_2$, —CO$_2$($C_{1-8}$)alkyl, —CO$_2$(aryl), —C(O)NH$_2$, —C(O)NH ($C_{1-8}$)alkyl, —C(O)N[($C_{1-8}$)alkyl]$_2$, —NHC(O)($C_{1-8}$) alkyl, ($C_{1-8}$alkyl)$_2$—N—($C_{1-8}$)alkyl, S(O)($C_{1-8}$)alkyl, —SO$_2$($C_{1-8}$)alkyl, —SO$_2$NH$_2$, —SO$_2$NH($C_{1-8}$)alkyl, —SO$_2$N[($C_{1-8}$)alkyl]$_2$, —C(O)($C_{1-8}$)alkyl, —C(O)aryl, —C(O)($C_{1-8}$)alkylaryl, halogen, hydroxy, cyano, nitro, phenyl, a 5-membered monocyclic aromatic ring containing one O, S, or N atom and up to three additional N atoms, a 6-membered monocyclic aromatic ring containing at least one N atom and up to two additional N atoms, and a partially saturated or unsaturated 5- or 6-membered monocyclic ring having one O, S or N atom which optionally contains up to one additional O, S or N atom;

$R_{10}$ is one or two substituents independently selected from the group consisting of $C_{1-8}$alkyl, phenyl, aryl($C_{1-6}$)alkyl, a 5-membered monocyclic aromatic ring containing one O, S, or N atom and up to three additional N atoms, a 6-membered monocyclic aromatic ring containing at least one N atom and up to two additional N atoms, and a partially saturated or unsaturated 5- or 6-membered monocyclic ring having one O, S or N atom which optionally contains up to one additional O, S or N atom;

$R_{11}$ is one or two substituents independently selected from the group consisting of hydrogen, $C_{1-8}$alkyl, $C_{2-8}$alkenyl, $C_{2-8}$alkynyl, $C_{3-8}$cycloalkyl, aryl($C_{1-8}$)alkyl, $C_{1-8}$alkoxy, aryloxy, aryl($C_{1-8}$)alkoxy, $C_{1-8}$alkylthio, trifluoro($C_{1-8}$) alkyl, trifluoro($C_{1-8}$)alkoxy, heterocyclyl($C_{1-6}$)alkyl amino, —NH($C_{1-8}$)alkyl, —N[($C_{1-8}$)alkyl]$_2$, —NH(aryl), —N(aryl)$_2$, —NH($C_{1-8}$)alkylaryl, —N[($C_{1-8}$)alkylaryl]$_2$, —CO$_2$($C_{1-8}$)alkyl, —CO$_2$(aryl), —C(O)NH$_2$, —C(O)NH ($C_{1-8}$)alkyl, —C(O)N[($C_{1-8}$)alkyl]$_2$, —NHC(O)($C_{1-8}$) alkyl, ($C_{1-8}$alkyl)$_2$—N—($C_{1-8}$)alkyl, S(O)($C_{1-8}$)alkyl, —SO$_2$($C_{1-8}$)alkyl, —SO$_2$NH$_2$, —SO$_2$NH($C_{1-8}$)alkyl, —SO$_2$N[($C_{1-8}$)alkyl]$_2$, —C(O)($C_{1-8}$)alkyl, —C(O)aryl, —C(O)($C_{1-8}$)alkylaryl, halogen, hydroxy, cyano, nitro, phenyl, a 5-membered monocyclic aromatic ring containing one O, S, or N atom and up to three additional N atoms, a 6-membered monocyclic aromatic ring containing at least one N atom and up to two additional N atoms, and a partially saturated or unsaturated 5- or 6-membered monocyclic ring having one O, S or N atom which optionally contains up to one additional O, S or N atom;

and pharmaceutically acceptable enantiomers, diastereomers and salts thereof.

DETAILED DESCRIPTION OF THE INVENTION

Embodiments of the present invention include compounds selected from a compound of Formula (I) wherein, preferably, A is Embodiments of the present invention include compounds selected from a compound of Formula (I) wherein, preferably, there are two Y substituents located at the 2- and 4-position.

Preferably, Y is selected from the group consisting of chlorine and methyl.

Embodiments of the present invention include compounds selected from a compound of Formula (I) wherein, preferably, L is —N($R_5$)—.

Preferably, $R_5$ is selected from the group consisting of hydrogen and $C_{1-6}$alkyl.

More preferably, $R_5$ is selected from the group consisting of hydrogen and methyl.

Embodiments of the present invention include compounds selected from a compound of Formula (I) wherein, preferably, M is selected from $C_{1-8}$alkylene.

More preferably, M is selected from the group consisting of —$CH_2CH_2$— and —$CH_2$—.

Embodiments of the present invention include compounds selected from a compound of Formula (I) wherein, preferably, Z is selected from the group consisting of (N—$R_6$)pyrrolylene and thienylene, each optionally substituted with one or two $C_{1-4}$alkyl substituents. In the case where Z is (N—$R_6$)pyrrolylene and thienylene, then the 2,5-(N—$R_6$)pyrrolylene and 2,5-thienylene is preferred.

More preferably, Z is (N—$R_6$)pyrrolylene optionally substituted with one or two $C_{1-4}$alkyl substituents.

Embodiments of the present invention include compounds selected from a compound of Formula (I) wherein, preferably, $R_6$ is independently selected from the group consisting of hydrogen, $C_{1-8}$alkyl and $C_{3-8}$cycloalkyl($C_{1-8}$)alkyl.

More preferably, $R_6$ is independently selected from the group consisting of hydrogen, methyl, ethyl and cyclopropyl-$CH_2$—.

Embodiments of the present invention include compounds selected from a compound of Formula (I) wherein, preferably, D is selected from the group consisting of —C(O)— and —NH—C(O)—.

Most preferably, D is —C(O)—.

Embodiments of the present invention include compounds selected from a compound of Formula (I) wherein, preferably, $R_1$ is selected from the group consisting of ($R_7$)aryl, ($R_8$)heteroaryl and ($R_{10}$)heterocyclyl($C_{1-8}$)alkyl.

More preferably, $R_1$ is selected from the group consisting of ($R_7$)phenyl, ($R_8$)pyridyl and ($R_{10}$)piperidinyl($C_{1-4}$)alkyl.

Even more preferably, $R_1$ is selected from the group consisting of ($R_7$)phenyl and ($R_8$)pyridyl.

Embodiments of the present invention include compounds selected from a compound of Formula (I) wherein, preferably, $R_7$ is selected from the group consisting of $C_{1-8}$alkyl, $C_{1-8}$alkoxy, $C_{1-8}$thioalkyl, trifluoro($C_{1-8}$)alkyl, heterocyclyl($C_{1-8}$)alkyl, amino, —NH($C_{1-8}$)alkyl, —N[($C_{1-8}$)alkyl]$_2$, —NHC(O)($C_{1-8}$)alkyl, —C(O)NH($C_{1-8}$)alkyl, —C(O)N[($C_{1-8}$)alkyl]$_2$, ($C_{1-8}$alkyl)$_2$—N—($C_{1-8}$)alkyl, —S(O)($C_{1-8}$)alkyl, —SO$_2$($C_{1-8}$)alkyl, —SO$_2$NH$_2$, —CO$_2$($C_{1-8}$)alkyl, halogen, cyano and nitro.

More preferably, $R_7$ is selected from the group consisting of $C_{1-8}$alkoxy, halogen and cyano.

Embodiments of the present invention include compounds selected from a compound of Formula (I) wherein, preferably, $R_8$ is selected from the group consisting of $C_{1-8}$alkyl, $C_{1-8}$alkoxy, $C_{1-8}$thioalkyl, halogen and cyano.

More preferably, $R_8$ is selected from the group consisting of halogen and cyano.

Embodiments of the present invention include compounds selected from a compound of Formula (I) wherein, preferably, $R_9$ is selected from the group consisting of hydrogen, $C_{1-8}$alkyl, $C_{1-8}$alkoxy, $C_{1-8}$thioalkyl, halogen and cyano.

Embodiments of the present invention include compounds selected from a compound of Formula (I) wherein, preferably, $R_{10}$ is selected from the group consisting of phenyl and phenyl($C_{1-4}$)alkyl.

Embodiments of the present invention include compounds selected from a compound of Formula (I) wherein, preferably, $R_{11}$ is selected from the group consisting of hydrogen, $C_{1-8}$alkyl, $C_{1-8}$alkoxy, $C_{1-8}$thioalkyl, halogen and cyano.

Exemplified compounds of the present invention include compounds of Formula (Ia):

Formula (Ia)

Wherein $R_1$ is selected from:

| Compound | $R_1$ |
|---|---|
| 23 | —(CH$_2$)$_4$CH$_3$ |
| 24 | —CH$_2$N(Me)Ph |
| 25 | (5-Cl)2-Thienyl |
| 26 | 2-Naphthyl |
| 27 | —CH=CHPh |
| 28 | —CH$_2$Ph |
| 29 | Ph |
| 30 | Cyclohexyl |
| 31 | —C(CH$_3$)$_3$ |

-continued

| Compound | $R_1$ |
|---|---|
| 32 | Cyclopropyl |
| 33 | 3-Pyridyl |
| 34 | (4-F)Ph |
| 35 | (4-Br)Ph |
| 36 | (2-NHAc)Ph |
| 37 | —CH$_2$Pyrrolidine |
| 38 | 1-Naphthyl |
| 39 | —CH=C(CH$_3$)$_2$ |
| 40 | (4-Cl)Ph |
| 41 | (5-Me)2-Thienyl |
| 42 | (3-NO$_2$)Ph |
| 43 | (5-SMe)2-Thienyl |
| 44 | (3-CN)Ph |
| 45 | 2-Pyridyl |
| 46 | (4-CH$_2$Pyrrolidine)Ph |
| 47 | (4-CH$_2$NMe$_2$)Ph |
| 48 | —CH$_2$NEt$_2$ |
| 49 | —CH$_2$N(Me)2-Pyridyl |
| 50 | (3,4-O$_2$CH$_2$)Ph |
| 51 | (4-CF$_3$)Ph |
| 118 | (4-NMe$_2$)Ph |
| 52 | (5,6-Cl)3-Pyridyl |
| 53 | (2-NH$_2$)Ph |
| 54 | (4-Me)Ph |
| 55 | 3-Thienyl |
| 56 | (4-NH$_2$)Ph |
| 57 | (3-NH$_2$)Ph |
| 58 | —CH$_2$((4-Ph)Piperidine) |
| 59 | —CH$_2$((4-Bn)Piperidine) |
| 60 | 4-Pyridyl |
| 61 | 2-Thienyl |
| 62 | (4-CONMe$_2$)Ph |
| 63 | (4-NO$_2$)Ph |
| 64 | (4-CO$_2$Me)Ph |
| 65 | (3-Me-4-NO$_2$)Ph |
| 66 | (2-NO$_2$)Ph |
| 67 | (6-Cl)3-Pyridyl |
| 68 | (4-OMe)Ph |
| 69 | (4-SMe)Ph |
| 70 | (4-SO$_2$NH$_2$)Ph |
| 71 | (6-CN)3-Pyridyl |
| 72 | (3-NHAc)Ph |
| 73 | (4-SOMe)Ph |
| 74 | (4-NHAc)Ph |
| 75 | (4-SO$_2$Me)Ph |
| 76 | (4-CN)Ph |

Exemplified compounds of the present invention include compounds of Formula (Ib):

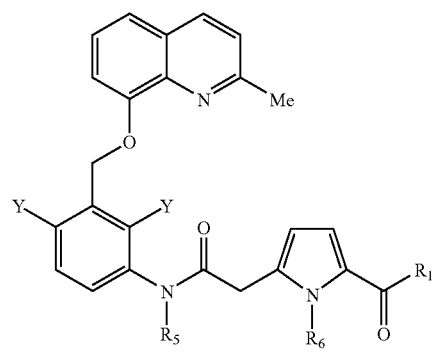

Formula (Ib)

Wherein Y, $R_1$, $R_5$ and $R_6$ are dependently selected from:

| Compound | Y | $R_5$ | $R_6$ | $R_1$ |
|---|---|---|---|---|
| 77 | Me | Me | Me | (6-Cl)3-Pyridyl |
| 78 | Me | Me | Me | (6-CN)3-Pyridyl |
| 79 | Me | Me | Me | (4-CN)Ph |
| 5 | Cl | Me | H | (4-OMe)Ph |
| 6 | Cl | Me | H | (4-CN)Ph |
| 7 | Me | Me | Et | (4-CN)Ph |
| 8 | Cl | Me | Et | (4-CN)Ph |
| 9 | Cl | Me | nPr | (4-CN)Ph |
| 10 | Cl | Me | nBu | (4-CN)Ph |
| 11 | Cl | Me | —CH$_2$cPr | (4-CN)Ph |
| 12 | Cl | Me | iBu | (4-CN)Ph |
| 13 | Cl | Me | iAm | (4-CN)Ph |
| 14 | Cl | H | Me | (6-CN)3-Pyridyl |
| 15 | Cl | H | Me | (4-CN)Ph |
| 16 | Me | Et | Me | (4-CN)Ph |
| 17 | Cl | Et | Me | (6-Cl)3-Pyridyl |
| 18 | Cl | Et | Me | (4-CN)Ph |
| 19 | Cl | nPr | Me | (4-CN)Ph |
| 21 | Cl | Allyl | Me | (4-CN)Ph |
| 119 | Cl | H | Me | (4-OMe)Ph |

Exemplified compounds of the present invention include compounds of Formula (Ic):

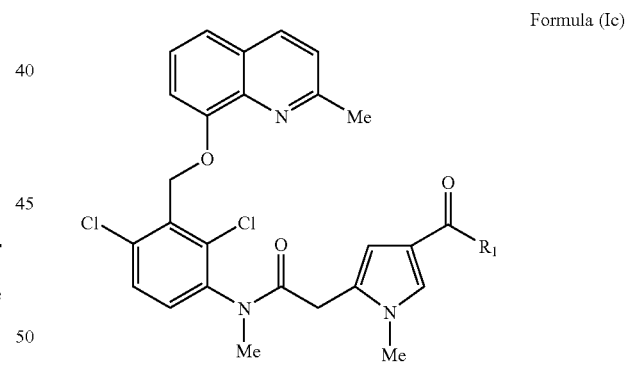

Formula (Ic)

Wherein $R_1$ is selected from:

| Compound | $R_1$ |
|---|---|
| 1 | (4-SO$_2$Me)Ph |
| 2 | (4-OMe)Ph |

Exemplified compounds of the present invention include compounds of Formula (Id):

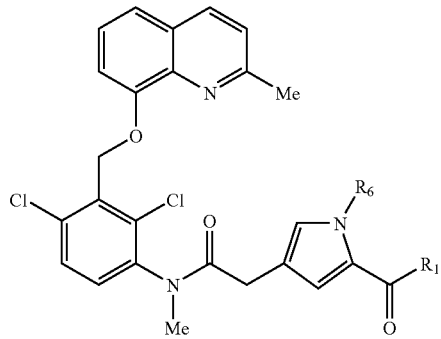

Formula (Id)

Wherein $R_1$ and $R_6$ are dependently selected from:

| Compound | $R_6$ | $R_1$ |
|---|---|---|
| 3 | Et | (4-CN)Ph |
| 4 | Me | (4-CN)Ph |

Exemplified compounds of the present invention include compounds of Formula (Ie):

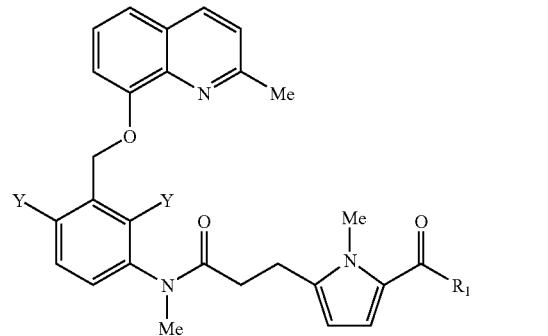

Formula (Ie)

| Compound | Y | $R_1$ |
|---|---|---|
| 80 | Me | 2-Thienyl |
| 81 | Cl | 2-Thienyl |
| 82 | Me | 4-Pyridyl |
| 83 | Cl | 4-Pyridyl |
| 84 | Me | 3-Pyridyl |
| 85 | Cl | 3-Pyridyl |
| 86 | Me | (6-OEt)3-Pyridyl |
| 87 | Cl | (6-OEt)3-Pyridyl |
| 88 | Me | (6-Cl)3-Pyridyl |
| 89 | Cl | (6-Cl)3-Pyridyl |
| 90 | Me | (4-CN)Ph |
| 91 | Cl | (4-CN)Ph |

Exemplified compounds of the present invention include compounds of Formula (If):

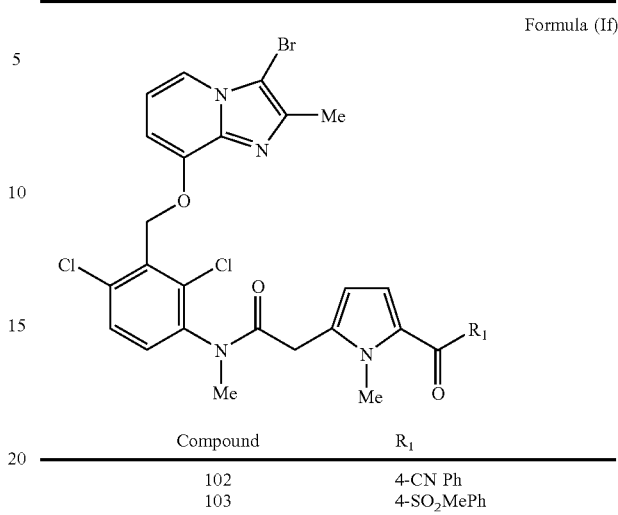

Formula (If)

| Compound | $R_1$ |
|---|---|
| 102 | 4-CN Ph |
| 103 | 4-SO$_2$MePh |

Exemplified compounds of the present invention include compounds of Formula (Ig):

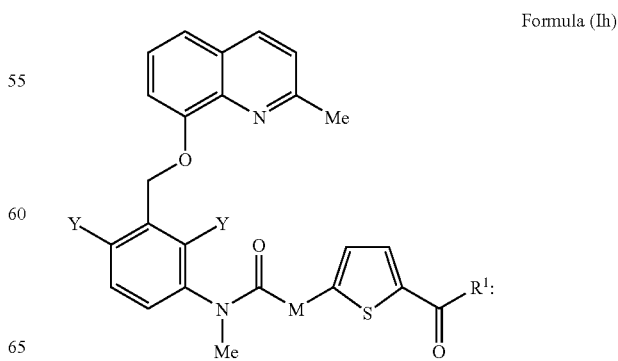

Formula (Ig)

| Compound | $R_1$ |
|---|---|
| 96 | 4-OCH$_3$ |
| 97 | 4-H |
| 98 | 4-CH$_3$ |

Exemplified compounds of the present invention include compounds of Formula (Ih):

Formula (Ih)

Wherein M, Y, and $R_1$ are dependently selected from:

| Compound | M | Y | $R_1$ |
|---|---|---|---|
| 104 | —$CH_2$—$CH_2$— | Me | Ph |
| 105 | —$CH_2$—$CH_2$— | Cl | Ph |
| 106 | —$CH_2$—$CH_2$— | Me | (4-OMe)Ph |
| 107 | —$CH_2$—$CH_2$— | Cl | (4-OMe)Ph |
| 108 | —$CH_2$— | Me | Ph |
| 109 | —$CH_2$— | Cl | Ph |
| 110 | —$CH_2$— | Me | (4-OMe)Ph |
| 111 | —$CH_2$— | Cl | (4-OMe)Ph |

Exemplified compounds of the present invention include compounds of Formula (Ii):

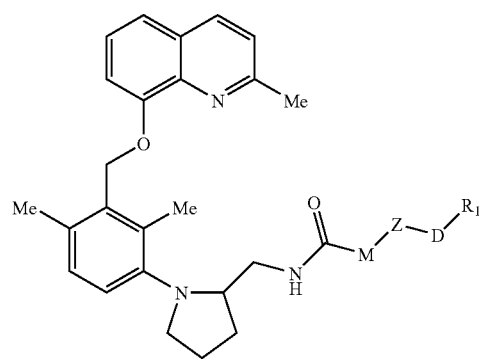

Formula (Ii)

Wherein M, Z, D and $R_1$ are selected from:

| Compound | M | Z | D | $R_1$ |
|---|---|---|---|---|
| 112 | —CH=CH— | 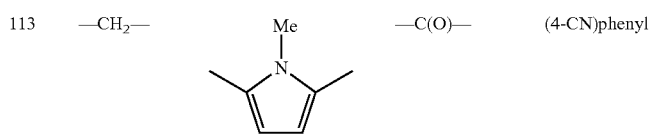 | —NH—C(O)— | Me |
| 113 | —$CH_2$— |  | —C(O)— | (4-CN)phenyl |
| 114 | —$CH_2CH_2$1' |  | —C(O)— | (4-CN)phenyl |

Exemplified compounds of the present invention include compounds of Formula (Ij):

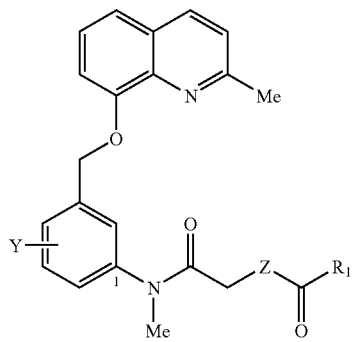

Formula (Ii)

Wherein Y, Z, and $R_1$ are independently selected from:

| Compound | Y | Z | $R_1$ |
|---|---|---|---|
| 115 | 2,5-diCl | (2,4-dimethylthiophene) | (4-CN)phenyl |
| 116 | 2-Cl | (1,2,5-trimethylpyrrole) | (3-CN)phenyl |

-continued

| Compound | Y | Z | R₁ |
|---|---|---|---|
| 117 | 2,4,6-triCl | Me-pyrrole | (6-Cl)3-pyridyl |
| 120 | 2,4-diCl | Me,Me-pyrrole-Me | (4-OMe)phenyl |
| 121 | 2,4-diCl | Me,Me-pyrrole-Me | (4-NH₂)phenyl |

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201-217; J. Pharm. Sci., 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature used throughout this disclosure, the terminal portion of the designated side chain is described first, followed by the adjacent functionality toward the point of attachment. Thus, for example, a "phenylC₁-C₆alkylaminocarbonylC₁-C₆alkyl" substituent refers to a group of the formula

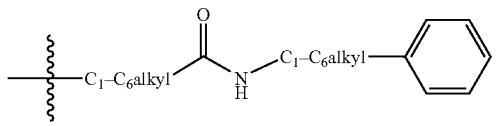

Divalent substituents drawn or named herein are read into the base structure from left to right.

The terms used in describing the invention are commonly used and known to those skilled in the art. However, the terms that could have other meanings are hereinafter defined. These definitions apply to the terms as they are used throughout this specification, unless otherwise limited in specific instances, either individually or as part of a larger group.

An "independently" selected substituent refers to a group of substituents, wherein the substituents may be different. Therefore, designated numbers of carbon atoms (e.g., C₁₋₈)

shall refer independently to the number of carbon atoms in an alkyl or cycloalkyl moiety or to the alkyl portion of a larger substituent in which alkyl appears as its prefix root.

Unless specified otherwise, the term "alkyl" refers to a saturated straight or branched chain consisting solely of 1-8 hydrogen substituted carbon atoms; preferably, 1-6 hydrogen substituted carbon atoms; and, most preferably, 1-4 hydrogen substituted carbon atoms. The term "alkenyl" refers to a partially unsaturated straight or branched chain consisting solely of 2-8 hydrogen substituted carbon atoms that contains at least one double bond. The term "alkynyl" refers to a partially unsaturated straight or branched chain consisting solely of 2-8 hydrogen substituted carbon atoms that contains at least one triple bond. The term "alkoxy" refers to —O-alkyl, where alkyl is as defined supra. The term "hydroxyalkyl" refers to radicals wherein the alkyl chain terminates with a hydroxy radical of the formula HO-alkyl, where alkyl is as defined supra. Alkyl, alkenyl and alkynyl chains are optionally substituted within the alkyl chain or on a terminal carbon atom.

The term "cycloalkyl" refers to a saturated or partially unsaturated monocyclic alkyl ring consisting of 3-8 hydrogen substituted carbon atoms or a saturated or partially unsaturated bicyclic ring consisting of 9 or 10 hydrogen substituted carbon atoms. Examples include, and are not limited to, cyclopropyl, cyclopentyl, cyclohexyl or cycloheptyl.

The term "heterocyclyl" refers to a saturated or partially unsaturated ring having five or six members of which at least one member is a N, O or S atom and which optionally contains additional N, O or S atoms; a saturated or partially unsaturated bicyclic ring having nine or ten members of which at least one member is a N, O or S atom and which optionally contains additional N, O, or S atoms. Examples include, and are not limited to, pyrrolinyl, pyrrolidinyl, 1,3-dioxolanyl, imidazolinyl, imidazolidinyl, pyrazolinyl, pyrazolidinyl, piperidinyl, morpholinyl or piperazinyl. Where the heterocycle is in $R_7$ it is preferably pyrroline, pyrrolidine, imidazoline, pyrazolidine, piperidine, piperazine and morpholine. Where the heterocyclyl is in $R_8$ it is preferably pyrrolidinyl, imidazolinyl, pyrazolidinyl, piperidinyl, piperazinyl and morpholinyl. Where the heterocycle is in $R_9$ it is preferably pyrrolidinyl, piperidinyl, piperazinyl and morpholinyl. Where the heterocycle is in $R_{10}$ it is preferably pyrrolidinyl, piperidinyl, piperazinyl and morpholinyl. Where the heterocycle is in $R_{11}$ it is preferably pyrrolidinyl, piperidinyl, piperazinyl and morpholinyl.

The term "aryl" refers to an aromatic monocyclic ring containing 6 hydrogen substituted carbon atoms, an aromatic bicyclic ring system containing 10 hydrogen substituted carbon atoms or an aromatic tricyclic ring system containing 14 hydrogen substituted carbon atoms. Examples include, and are not limited to, phenyl, naphthalenyl, phenanthracenyl or anthracenyl.

The term "heteroaryl" refers to an aromatic monocyclic ring system containing five or six members of which at least one member is a N, O or S atom and which optionally contains additional N, S or O atoms; an aromatic bicyclic ring having nine or ten members of which at least one member is a N, O or S atom and which optionally contains additional N, S or O atoms. Examples include, and are not limited to, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, indolyl, indazolyl, benzo[b]thienyl, quinolinyl, isoquinolinyl or quinazolinyl. Where the heteroaryl is in $R_7$ it is preferably furanyl, thienyl, oxazolyl, thiazolyl, imidazolyl, pyrazolyl, pyridinyl, pyridazinyl, pyrimidinyl, and pyrazinyl. Where the heteroaryl is in $R_8$ it is preferably furanyl, thienyl, oxazolyl, thiazolyl, imidazolyl, pyrazolyl, pyridinyl, pyridazinyl, pyrimidinyl, and pyrazinyl. Where the heteroaryl is in $R_9$ it is preferably furanyl, thienyl, pyridinyl, pyridazinyl, pyrimidinyl, and pyrazinyl. Where the heteroaryl is in $R_9$ it is preferably furanyl, thienyl, pyridinyl, pyridazinyl, pyrimidinyl, and pyrazinyl. Where the heteroaryl is in $R_{10}$ it is preferably furanyl, thienyl, pyridinyl, pyridazinyl, pyrimidinyl, and pyrazinyl. Where the heteroaryl is in $R_{11}$ it is preferably furanyl, thienyl, pyridinyl, pyridazinyl, pyrimidinyl, and pyrazinyl.

Whenever the term "alkyl" or "aryl" or either of their prefix roots appear in a name of a substituent (e.g., aryl $(C_{1-6})$alkyl) it shall be interpreted as including those limitations given above for "alkyl" and "aryl." Designated numbers of carbon atoms (e.g., $C_{1-6}$) shall refer independently to the number of carbon atoms in an alkyl or cycloalkyl moiety or to the alkyl portion of a larger substituent in which alkyl appears as its prefix root.

The term "halogen" shall include iodine, bromine, chlorine and fluorine.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The novel heteroaryl alkylamide compounds of the present invention are useful bradykinin receptor modulators. In particular, certain heteroaryl alkylamide compounds are bradykinin receptor antagonists useful in the treatment or amelioration of conditions such as pain, inflammatory joint disease, inflammatory bowel disease, allergy, asthma, rhinitis, brain edema and trauma, tissue injury, septic shock or acute pancreatitis. Examples of pain intended to be within the scope of the present invention include, but are not limited to, centrally mediated pain, peripherally mediated pain, structural or soft tissue injury related pain, progressive disease related pain, neuropathic pain and acute pain such as caused by acute injury, trauma or surgery and chronic pain such as caused by neuropathic pain conditions, diabetic peripheral neuropathy, post-herpetic neuralgia, trigeminal neuralgia, post-stroke pain syndromes or cluster or migraine headaches. Also, certain compounds of the present invention are bradykinin receptor agonists useful in the treatment or amelioration of conditions such hypertension. The utility of the instant compounds as bradykinin receptor modulators, antagonists or agonists can be determined according to the procedures described herein.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating pain, inflammatory joint disease, inflammatory bowel disease, allergy, asthma, rhinitis, brain edema and trauma, tissue injury, septic shock, acute pancreatitis, post-operative pain and migraine described in the present invention may also be carried out using a pharmaceutical composition comprising any of the compounds as defined herein and a pharmaceutically acceptable carrier. The pharmaceutical composition may contain between about 5 mg and 1000 mg, preferably about 10 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

The present invention includes a method for treating a disorder modulated by the bradykinin receptor. An embodiment of the present invention is a method for treating pain, inflammatory joint disease, inflammatory bowel disease, allergy, asthma, rhinitis, brain edema and trauma, tissue injury, septic shock, acute pancreatitis, or any other disorder modulated by the bradykinin receptor.

The present invention therefore provides a method for the use of the instant heteroaryl alkylamide compounds as bradykinin receptor modulators comprising administering to a subject any of the compounds as defined herein in a therapeutically effective amount. A compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

A therapeutically effective amount for use of the instant compounds or a pharmaceutical composition thereof comprises a dose range of from about 0.001 mg to about 1,000 mg, in particular from about 0.1 mg to about 500 mg or, more particularly from about 1 mg to about 250 mg of active ingredient per day for an average (70 kg) human.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. Advantageously, compounds of the present invention may be administered in a single daily dose or the total daily dosage may be administered in divided doses of two, three or four times daily.

It is apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Compounds of this invention may be administered in any of the foregoing compositions and dosage regimens or by means of those compositions and dosage regimens established in the art whenever use of the compounds of the invention as bradykinin receptor modulators is required for a subject in need thereof.

The terms used in describing the invention are commonly used and known to those skilled in the art. As used herein, the following abbreviations have the indicated meanings:

DMF=N,N-Dimethylformamide
DMAP=Dimethylaminopyridine
EtOAc=Ethyl acetate
HATU=O-7-azabenzotriazol-1-yl),N,N,N',N'-tetramethyluronium hexafluorophosphate
HBTU=O-benzotriazol-1-yl),N,N,N',N'-tetramethyluronium hexafluorophosphate
NBS=N-bromosuccinimide
THF=Tetrahydrofuran General Synthetic Methods Representative compounds of the present invention can be synthesized in accordance with the general synthetic methods described below and are illustrated in the schemes that follows. Since the schemes are an illustration, the invention should not be construed as being limited by the chemical reactions and conditions expressed. The preparation of the various starting materials used in the schemes is well within the skill of persons versed in the art.

Scheme A

Certain target compounds of the present invention may be prepared according to the process outlined in Scheme A below.

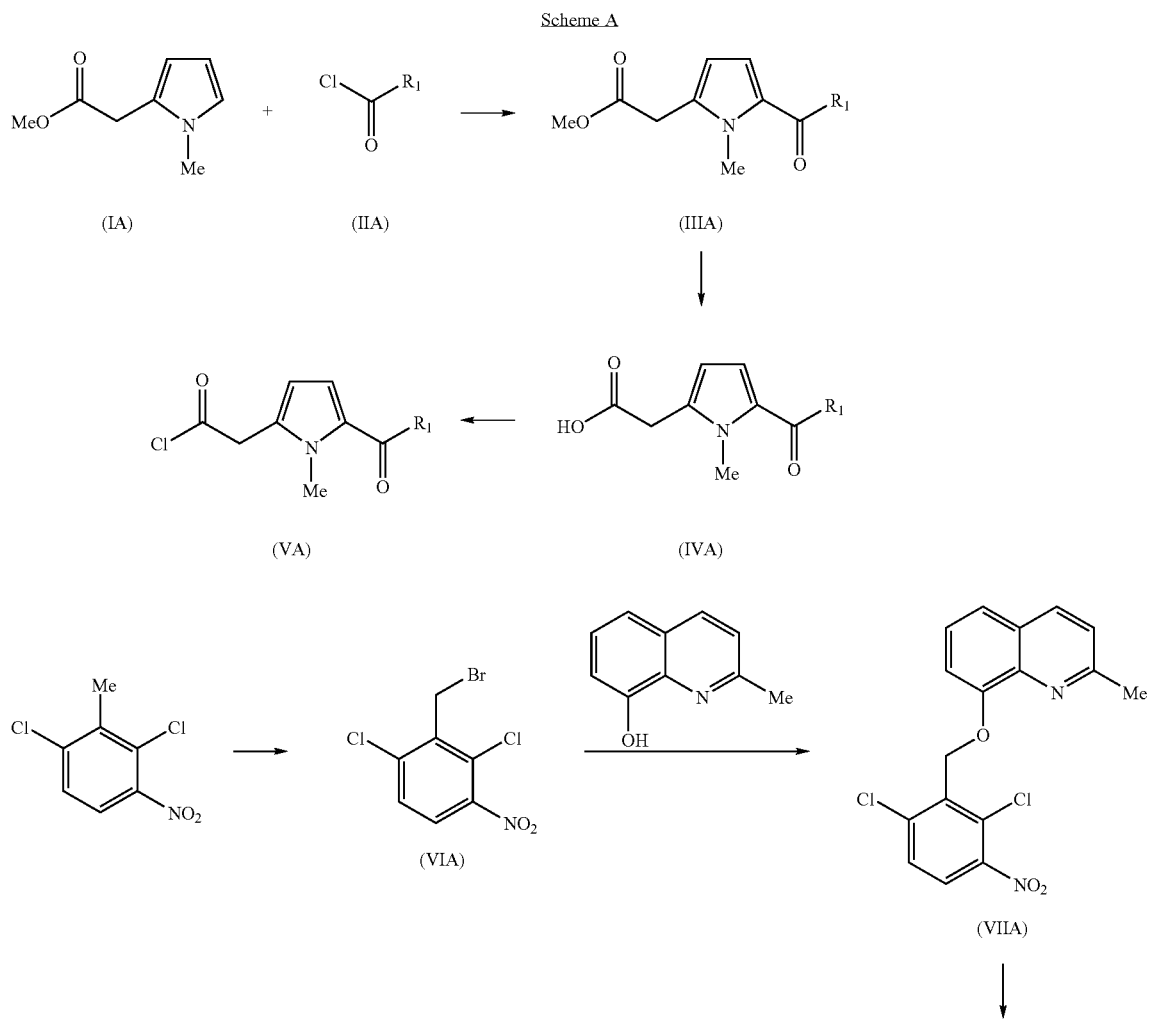

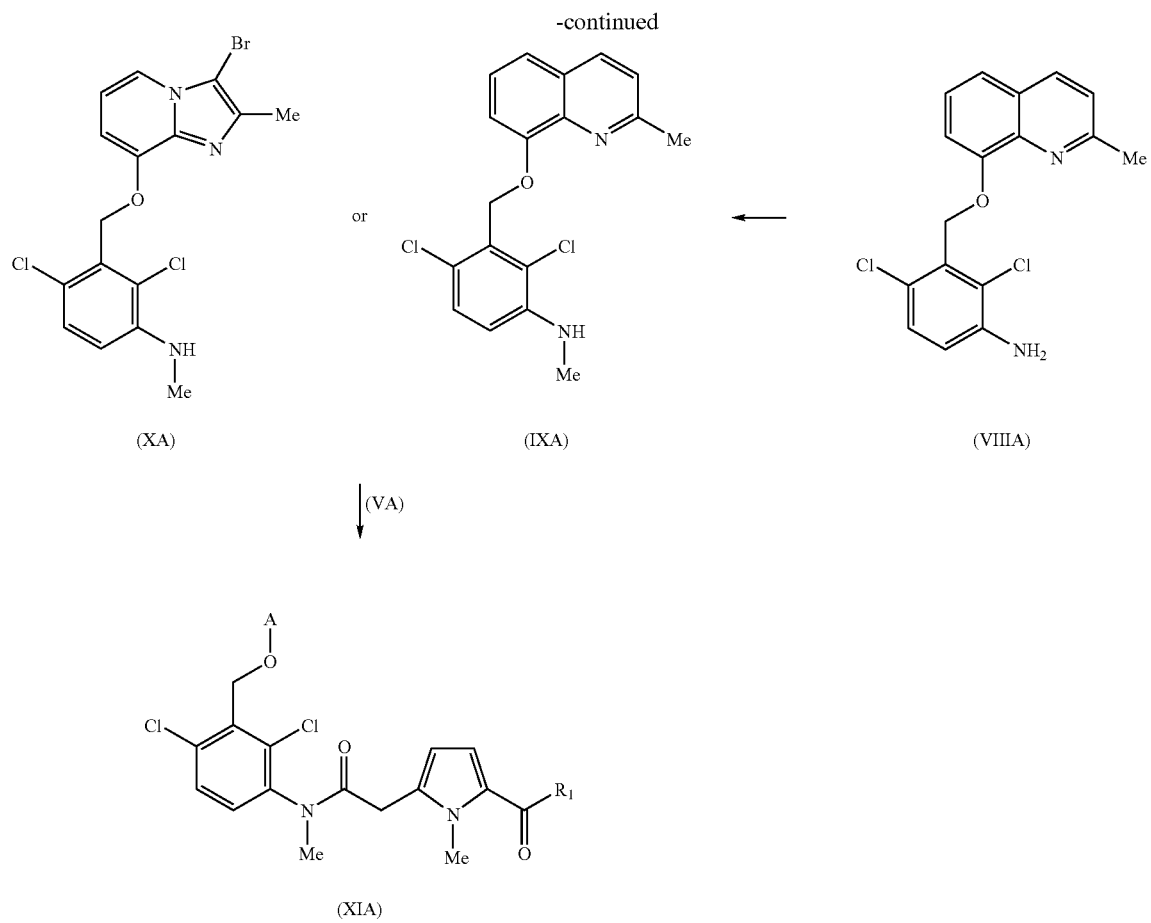

More specifically, 1-methyl-pyrroleacetate (purchased from Aldrich Chemicals) (IA) was reacted with a suitably substituted acid chloride of formula (IIA) in the presence of a suitable solvent such as toluene, benzene and the like, at an elevated temperature, preferably at a temperature in the range of 80-100° C., to yield the corresponding compound of formula (IIIA).

The compound of formula (IIIA) was saponified by reaction with a suitable base such as sodium hydroxide, lithium hydroxide, potassium hydroxide, sodium carbonate or potassium carbonate and the like in a suitable solvent such as aqueous THF, water, ethanol, methanol and the like, at a temperature in the range of ambient temp to 100° C. to yield the corresponding compound of formula (IVA).

The compound of formula (IVA) was reacted with a chlorinating agent such as oxalyl chloride or thionyl chloride in the presence of an acylation catalyst such as DMF in a suitable solvent such as methylene chloride or dichloroethane and the like at a temperature of about 0° C. to yield the corresponding compound of formula (VA).

2,6-Dichloro-3-nitro-toluene (purchased from Lancaster Synthesis) was reacted with a brominating agent such as N-bromosuccinimide and a radical initiator such as benzoyl peroxide in a suitable solvent such as carbon tetrachloride in the presence of a source of illumination such as a 150 Watt lamp at an elevated temperature, preferably at a temperature in the range of 70-100° C., to yield the corresponding compound of formula (VIA).

8-Hydroxyquinaldine (purchased from Aldrich Chemicals) was reacted with sodium hydride in a suitable solvent such as DMF or THF and the like at a temperature about 0° C. The compound of formula (VIA) was added to this reaction mixture and reacted at a temperature of about 0° C. to yield the corresponding compound of formula (VIIA).

The compound of formula (VIIA) was reduced with a suitable reducing agent such as stannous(II) chloride or ferrous(II) chloride in the presence of an acid such as HCl or acetic acid at room temperature to yield the corresponding compound of formula (VIIIA).

The compound of formula (VIIIA) was reacted with triethylorthoformate and an acid such as trifluoracetic acid and a reducing agent such as sodium borohydride in a suitable solvent such as ethanol or methanol and the like at an elevated temperature, preferably a temperature in the range of 70-100° C. to yield the corresponding compound of formula (IXA).

The compound of formula (IXA) was reacted with the compound of formula (VA) in the presence of an organic base such as diisopropylethylamine or triethylamine and the like, in a suitable solvent such as methylene chloride, dichloroethane, DMF and the like, to yield the corresponding compound of formula (XIA).

Alternatively, the compound of formula (XA), as prepared by literature methods (Kayakiri et al. *J. Med. Chem.* 1998, 41, 564-78), was reacted with the compound of formula (VA) in the presence of an organic base such as diisopropylethylamine or triethylamine and the like, in a suitable solvent such as methylene chloride, dichloroethane, DMF and the like, to yield the corresponding compound of formula (XIA).

Scheme B

Certain target compounds of the present invention may be prepared according to the process outlined in Scheme B below.

More specifically, 2,6 dimethylbenzoic acid (purchased from Aldrich Chemicals) was nitrated with a mixture of sulfuric acid, acetic acid and nitric acid at a temperature of about 0° C. to yield the corresponding compound of formula (IB).

The compound of formula (IB) was reduced with a reducing agent such as benzyltriethylammonium borohydride/trimethylsilylchloride in a suitable halogenated sol-

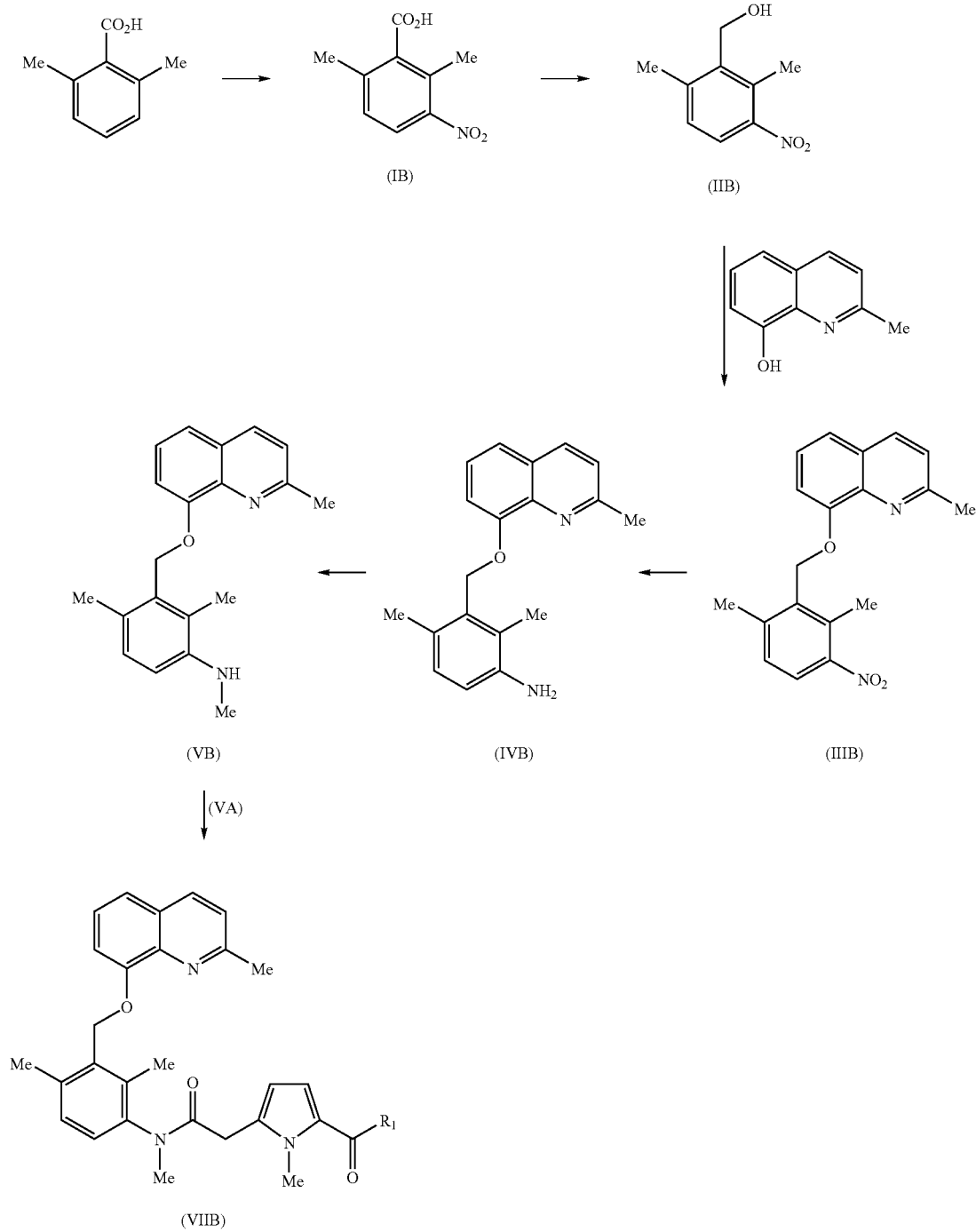

vent such as methylene chloride or dichloromethane and the like, at a temperature range of about 0° C. to room temperature to yield the corresponding compound of formula (IIB).

The compound of formula (IIB) was reacted with 8-hydroxyquinaldine (purchased from Aldrich Chemicals), an alkylphosphine such as tributylphosphine and an additive such as 1,1'-(azidodicarbonyl)dipiperidine (ADDP, purchased from Aldrich Chemicals) in a suitable solvent such as benzene toluene and the like, at a temperature from about 0° C. to room temperature to yield the corresponding compound of formula (IIIB).

The compound of formula (IIIB) was reduced by reaction with a suitable reducing agent such as stannous(II) chloride or ferrous chloride in the presence of an acid such as HCl or acetic acid at room temperature to yield the corresponding compound of formula (IVB).

The compound of formula (IVB) was reacted with sodium methoxide and paraformaldehyde in a suitable solvent such as methanol at an elevated temperature, preferably at a temperature in the range of 70-90° C., to yield the compound of formula (VB).

The compound of formula (VB) was reacted with a suitably substituted pyrroleacetyl chloride compound of formula (VA), the synthesis of which is described in Scheme A, in the presence of an organic base such as diisopropylethylamine or triethylamine and the like, in a suitable solvent such as methylene chloride, dichloroethane, DMF and the like, to yield the corresponding compound of formula (VIIB).

Scheme C

Certain target compounds of the present invention may be prepared according to the process outlined in Scheme C below.

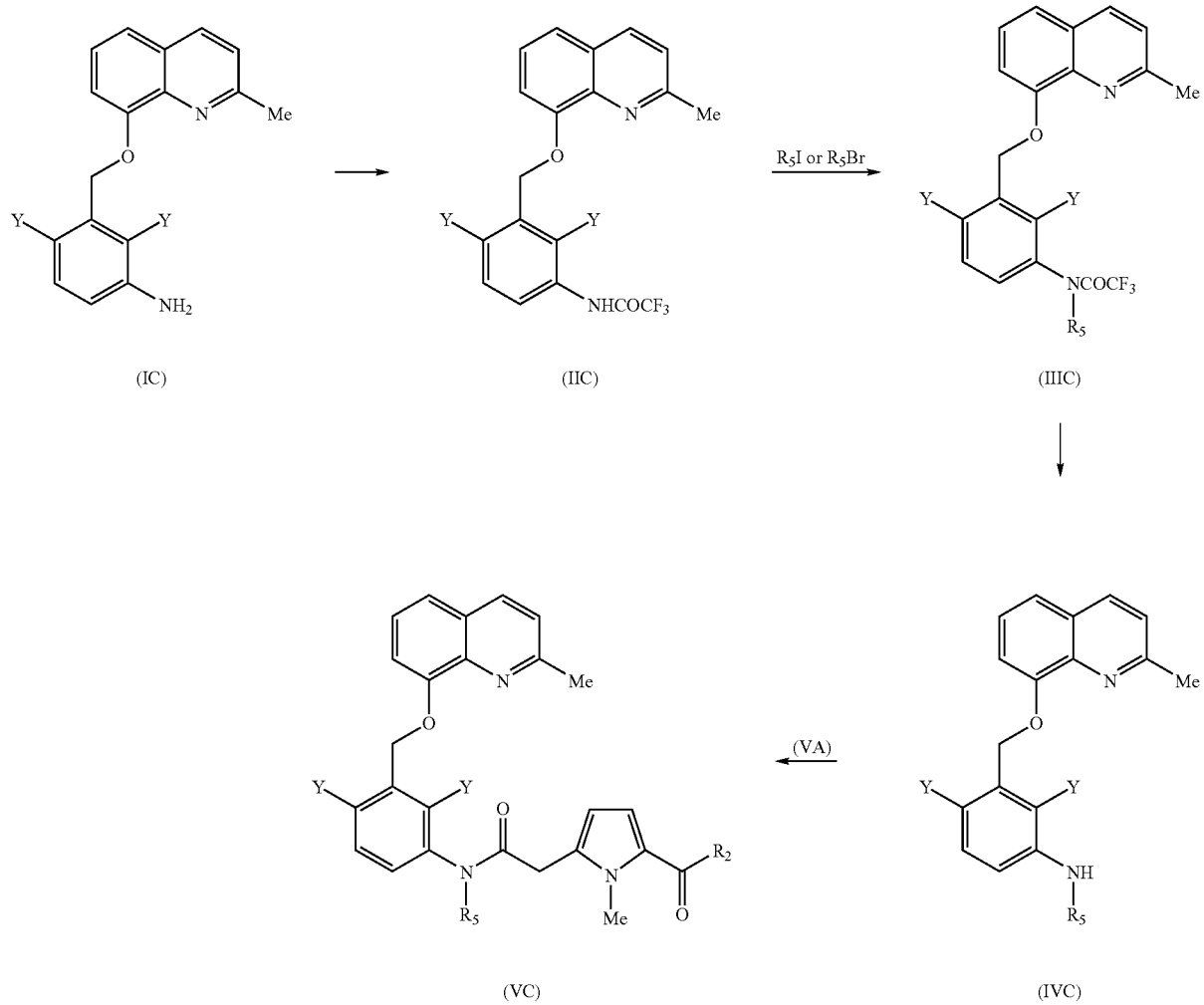

More specifically, a compound of formula (IC), the synthesis of which is described in Schemes A and B, was reacted with a trifluoroacetylating agent such as trifluoroacetic anhydride in a solvent such as chloroform, methylene chloride, dichloroethane and the like at room temperature to 60° C. to yield the corresponding compound of formula (IIC).

The compound of formula (IIC) was reacted with a strong base such as sodium hydride, potassium hydride, sodium hydroxide, potassium hydroxide and the like in a solvent such as ether, THF, DMF and the like followed by reaction with an alkylating agent such as an alkyl, allyl or benzyl halide (iodide or bromide), alkyl, allyl or benzylsulfonate and the like to yield the corresponding compound of formula (IIIC).

The compound of formula (IIIC) was reacted with a reducing agent such as sodium borohydride, sodium triacetoxyborohydride, or sodium cyanoborohydride in a solvent such as methanol, ethanol, THF and the like to yield the corresponding compound of formula (IVC).

The compound of formula (IVC) was reacted with a suitably substituted pyrroleacetyl chloride compound of formula (VA), the synthesis of which is described in Scheme A, in the presence of an organic base such as diisopropylethylamine or triethylamine and the like, in a suitable solvent such as methylene chloride, dichloroethane, DMF and the like, to yield the corresponding compound of formula (VC).

Scheme D

Certain target compounds of the present invention may be prepared according to the process outlined in Scheme D below.

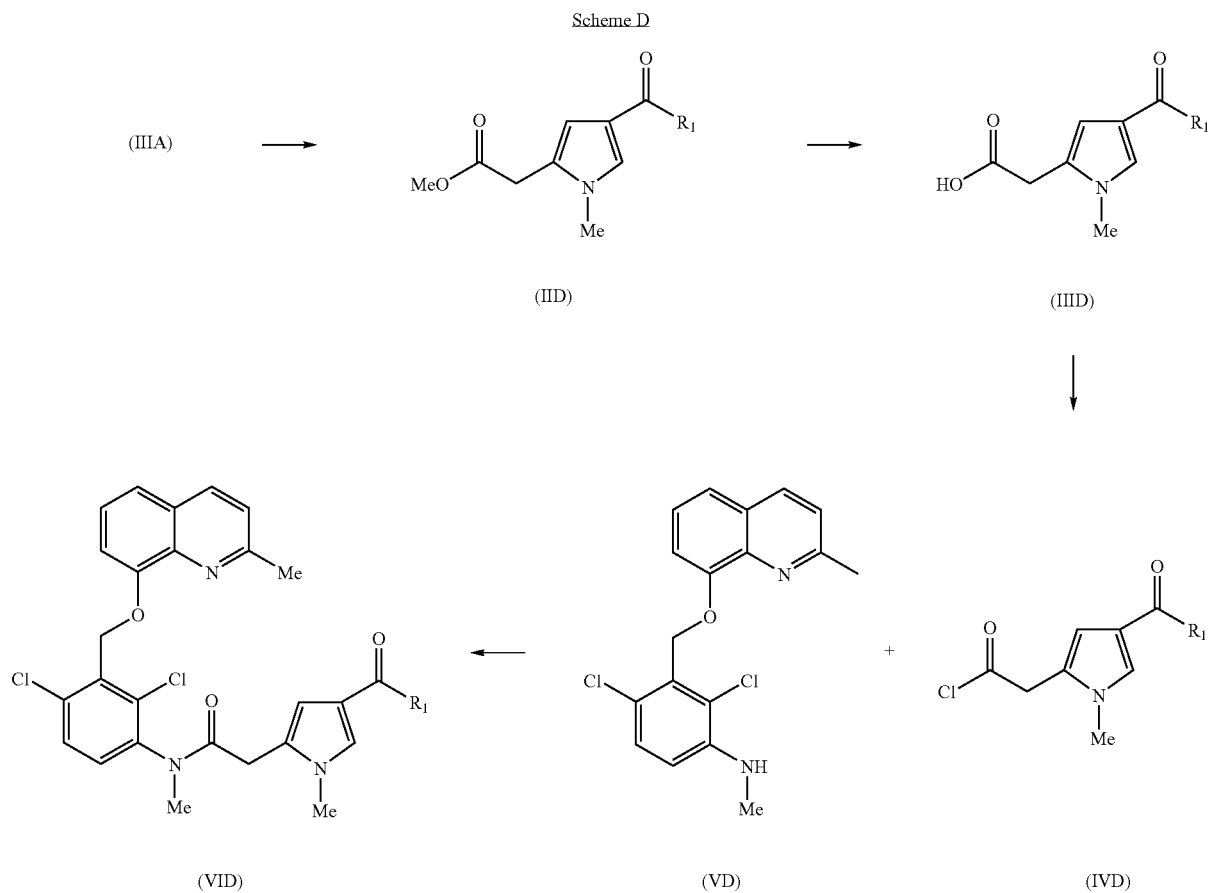

More specifically, a suitably substituted 2,5 pyrroleacetic ester of formula (IIIA), the synthesis of which is described in Scheme A, was dissolved in an acid such as trifluoroacetic acid or polyphosphoric acid (PPA) and heated to an elevated temperature, preferably a temperature in the range of 70-120° C., to yield the corresponding compound of formula (IID).

The compound of formula (IID) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (IIID).

The compound of formula (IIID) was reacted with a chlorinating agent such as oxalyl chloride or thionyl chloride in the presence of an acylation catalyst such as DMF in a suitable solvent such as methylene chloride or dichloroethane and the like at a temperature of about 0° C. to yield the corresponding compound of formula (IVD).

The compound of formula (IVD) was reacted with the compound of formula (VD), the synthesis of which is described in Scheme A, in the presence of an organic base such as diisopropylethylamine or triethylamine and the like, in a suitable solvent such as methylene chloride, dichloroethane, DMF and the like, to yield the corresponding compound of formula (VID).

Scheme E

Certain target compounds of the present invention may be prepared according to the process outlined in Scheme E below.

chloride or thionyl chloride in an ethereal solvent such as ether or THF. The compound of formula (IE) was then reacted with t-butyl-2-pyrroleacetate, which was prepared according to literature procedures (*J. Org. Chem.* 1994, 59, 5230-34), in the presence of an aqueous buffer such as sodium acetate in a suitable solvent such as methylene chloride, chloroform or dichloroethane at ambient temperature to yield the compound of formula (IIE).

The compound of formula (IIE) was hydrolyzed with an acid such as trifluoroacetic acid in a suitable solvent such as methylene chloride or dichloroethane to yield the compound of formula (IIIE).

The compound of formula (IIIE) was reacted with a chlorinating agent such as oxalyl chloride or thionyl chloride in the presence of an acylation catalyst such as DMF in a suitable solvent such as methylene chloride, chloroform or dichloroethane and the like at a temperature of about 0° C. to yield the corresponding compound of formula (IVE).

The compound of formula (IVE) was reacted with the compound of formula (IVC), the synthesis of which is described in Schemes A and B, in the presence of an organic base such as diisopropylethylamine or triethylamine and the like, in a suitable solvent such as methylene chloride,

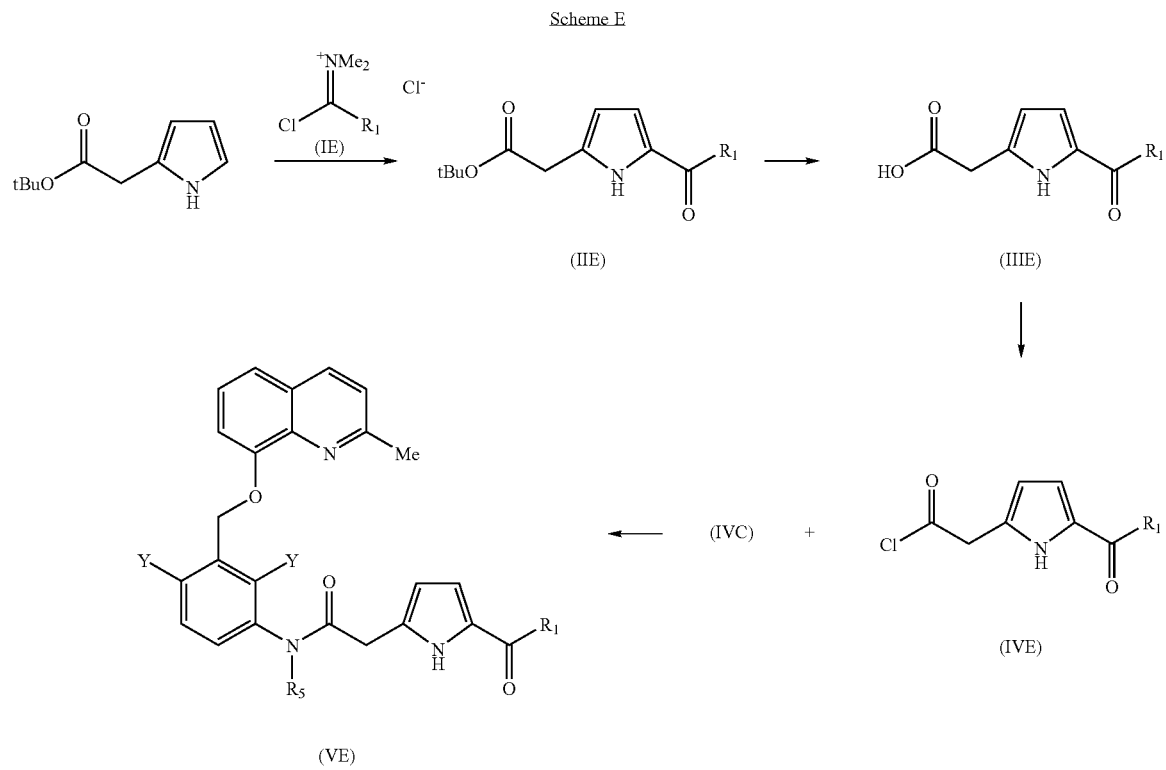

More specifically, compounds of formula (IE) were synthesized by reaction of a suitably substituted acid chloride with dimethylamine in the presence of an aqueous base such as sodium hydroxide or potassium hydroxide in a suitable solvent such as chloroform, methylene chloride or dichloroethane at ambient temperature followed by reaction of the resulting amide with a chlorinating agent such as oxalyl chloride, dichloroethane, DMF and the like, to yield the corresponding compound of formula (VE).

Scheme F

Certain target compounds of the present invention may be prepared according to the process outlined in Scheme F below.

Scheme F

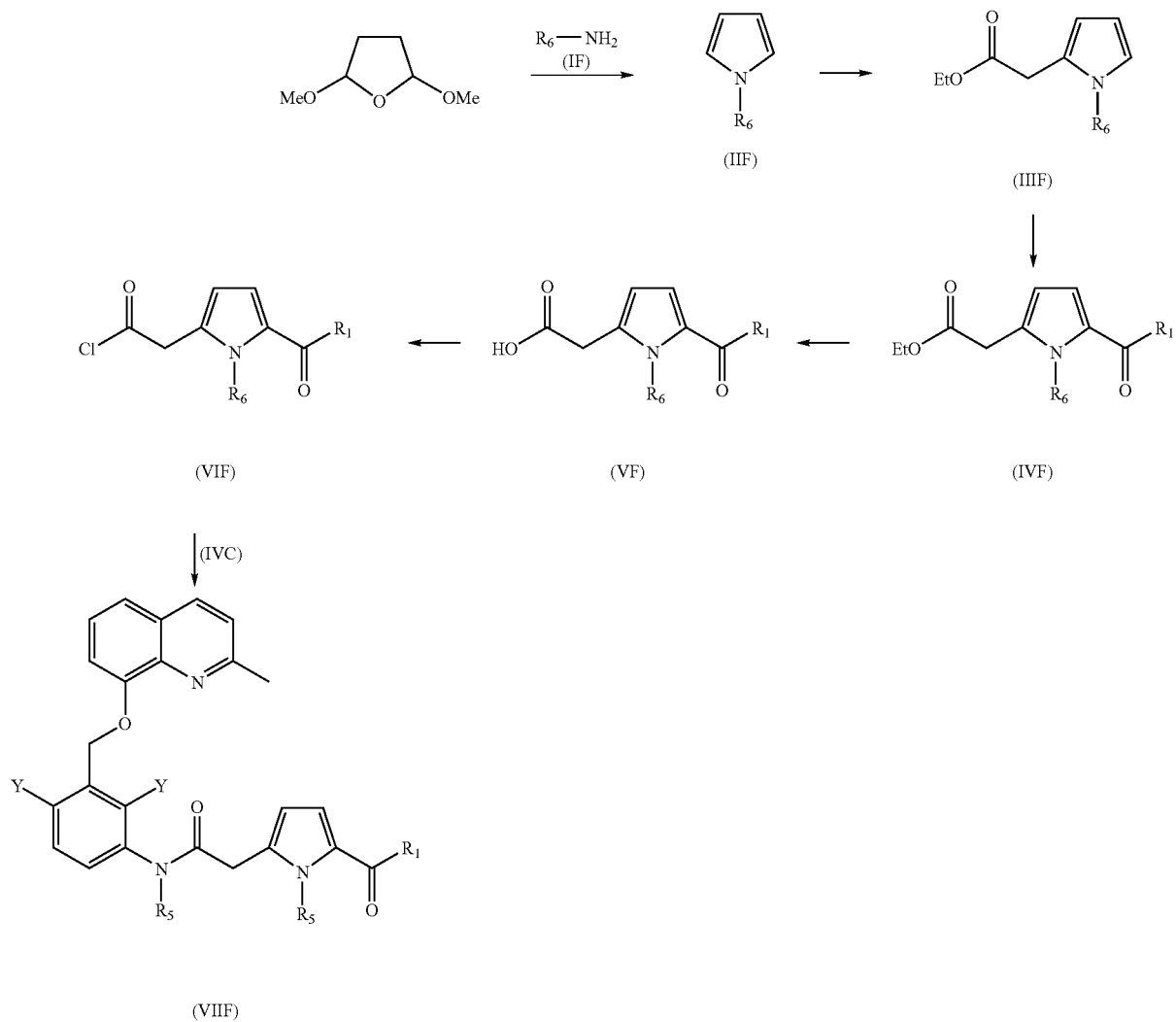

More specifically, dimethoxytetrahydrofuran (purchased from Aldrich Chemicals) was reacted with a suitably substituted amine of formula (IF) in an acid such as acetic acid at an elevated temperature, preferably a temperature in a range of 70-120° C., to yield the corresponding compound of formula (IIF).

The compound of formula (IIF) was reacted with ethyldiazoacetate in the presence of a copper compound such as copper bronze at an elevated temperature, preferably at a temperature in a range of 50-100° C. to yield the corresponding compound of formula (IIIF).

The compound of formula (IIIF) was reacted with a suitably substituted acid chloride. in the presence of a suitable solvent such as toluene, benzene and the like, at an elevated temperature, preferably at a temperature in the range of 80-100° C., to yield the corresponding compound of formula (IVF).

The compound of formula (IVF) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (VF).

The compound of formula (VF) was reacted with a chlorinating agent such as oxalyl chloride or thionyl chloride in the presence of an acylation catalyst such as DMF in a suitable solvent such as methylene chloride, chloroform or dichloroethane and the like at a temperature of about 0° C. to yield the corresponding compound of formula (VIF).

The compound of formula (VIF) was reacted with the compound of formula (IVC), the synthesis of which is described in Scheme A and Scheme B, in the presence of an organic base such as diisopropylethylamine or triethylamine and the like, in a suitable solvent such as methylene chloride, dichloroethane, DMF and the like, to yield the corresponding compound of formula (VIIF).

Scheme G

Certain target compounds of the present invention may be prepared according to the process outlined in Scheme G below.

Scheme G

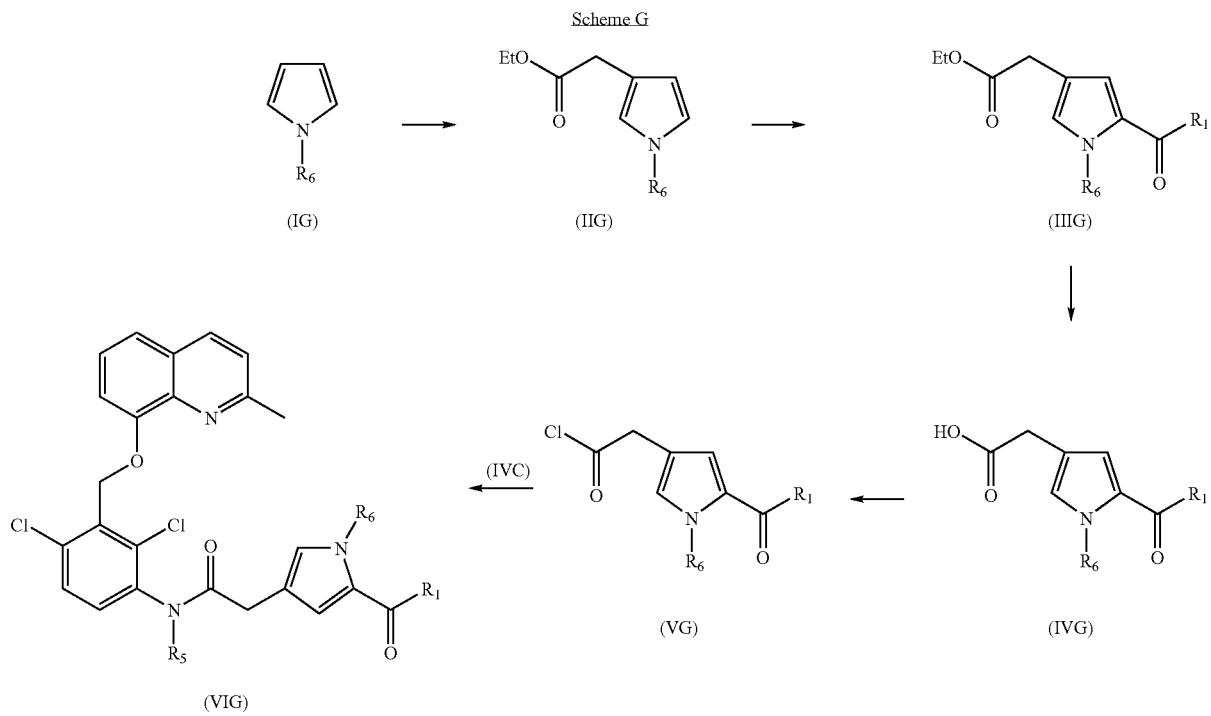

More specifically, a compound of formula (IG) (purchased from Aldrich Chemicals) was reacted with ethyldiazoacetate in the presence of a copper compound such as copper(II) triflate or copper bronze at an elevated temperature, preferably at a temperature in a range of 50-90° C. to yield the corresponding compound of formula (IIG).

The compound of formula (IIG) was reacted with a suitably substituted acid chloride in the presence of a suitable solvent such as toluene, benzene and the like, at an elevated temperature, preferably at a temperature in the range of 80-100° C., to yield the corresponding compound of formula (IIIG).

The compound of formula (IIIG) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (IVG).

The compound of formula (IVG) was reacted with a chlorinating agent such as oxalyl chloride or thionyl chloride in the presence of an acylation catalyst such as DMF in a suitable solvent such as methylene chloride or dichloroethane and the like at a temperature of about 0° C. to yield the corresponding compound of formula (VG).

The compound of formula (VG) was reacted with the compound of formula (IVC), the synthesis of which is described in Scheme A and Scheme B, in the presence of an organic base such as diisopropylethylamine or triethylamine and the like, in a suitable solvent such as methylene chloride, dichloroethane, DMF and the like, to yield the corresponding compound of formula (VIG).

Scheme H

Certain target compounds of the present invention may be prepared according to the process outlined in Scheme H below.

Scheme H

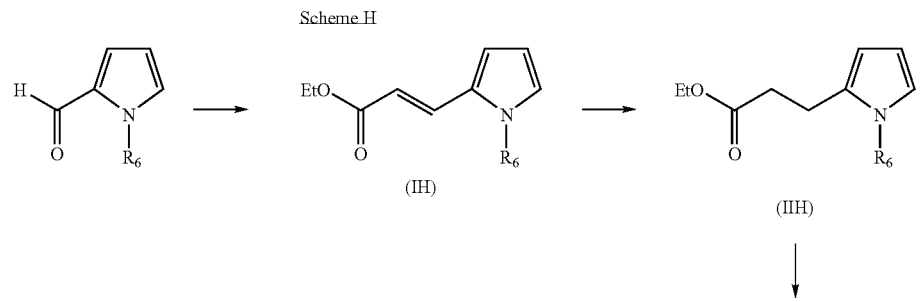

-continued

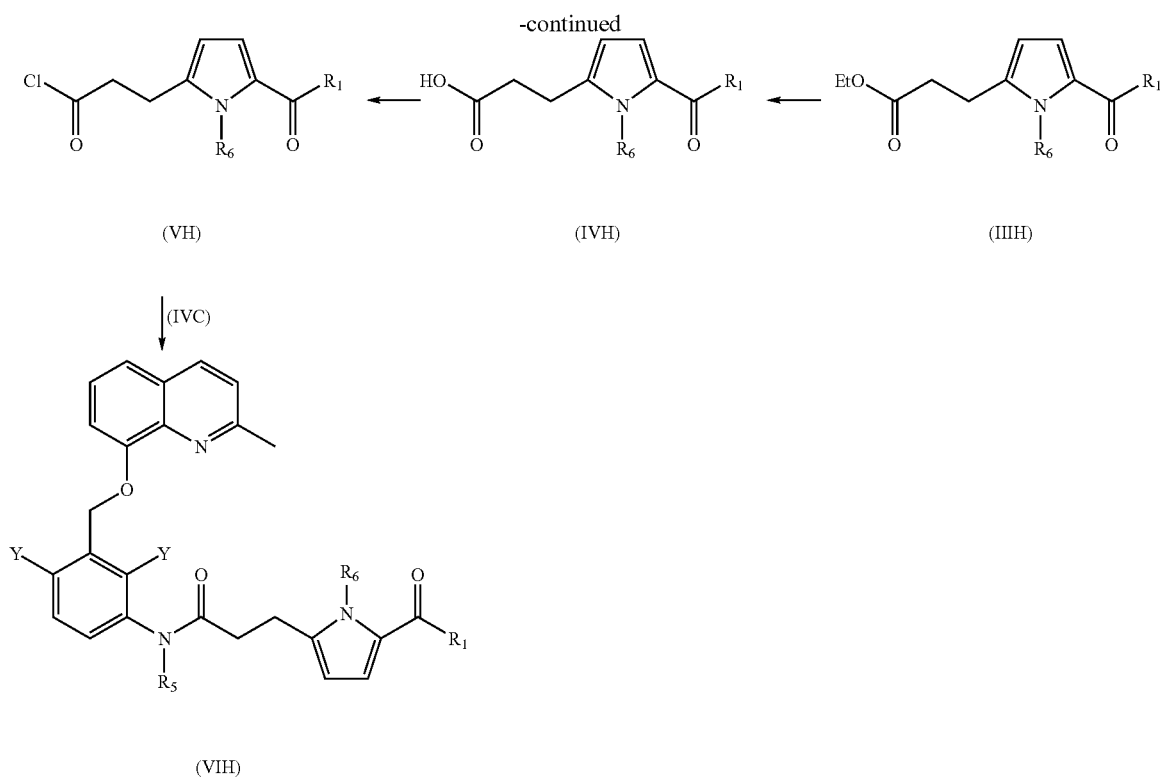

More specifically, N-methyl-2-carboxaldehyde (purchased from Aldrich Chemicals) was reacted with a Wittig reagent such as ethyl(triphenylphosphoranylidene)acetate (purchased from Aldrich Chemicals) in a suitable solvent such a benzene or toluene at an elevated temperature, preferably at a temperature in a range of 80-100° C. to yield the compound of formula (IH).

The compound of formula (IH) was reduced by treating with hydrogen gas at an elevated pressure in the range of about 40-50 psi in a suitable solvent such as ethanol or methanol and the like, in the presence of a catalyst such as 10% palladium on carbon at ambient temperature to yield the corresponding compound of formula (IIH).

The compound of formula (IIH) was reacted with a suitably substituted acid chloride in the presence of a suitable solvent such as toluene, benzene and the like, at an elevated temperature, preferably at a temperature in the range of 80-100° C., to yield the corresponding compound of formula (IIIH).

The compound of formula (IIIH) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (IVH).

The compound of formula (IVH) was reacted with a chlorinating agent such as oxalyl chloride or thionyl chloride in the presence of an acylation catalyst such as DMF in a suitable solvent such as methylene chloride, chloroform or dichloroethane and the like at a temperature of about 0° C. to yield the corresponding compound of formula (VH).

The compound of formula (VH) was reacted with the compound of formula (IVC), the synthesis of which is described in Scheme A and Scheme B, in the presence of an organic base such as diisopropylethylamine or triethylamine and the like, in a suitable solvent such as methylene chloride, dichloroethane, DMF and the like, to yield the corresponding compound of formula (VIH).

Scheme I

Certain target compounds of the present invention may be prepared according to the process outlined in Scheme I below.

Scheme I

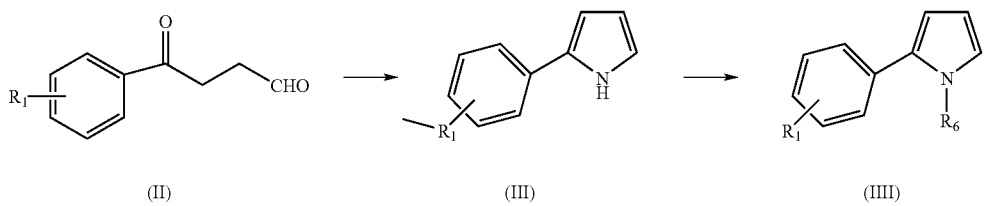

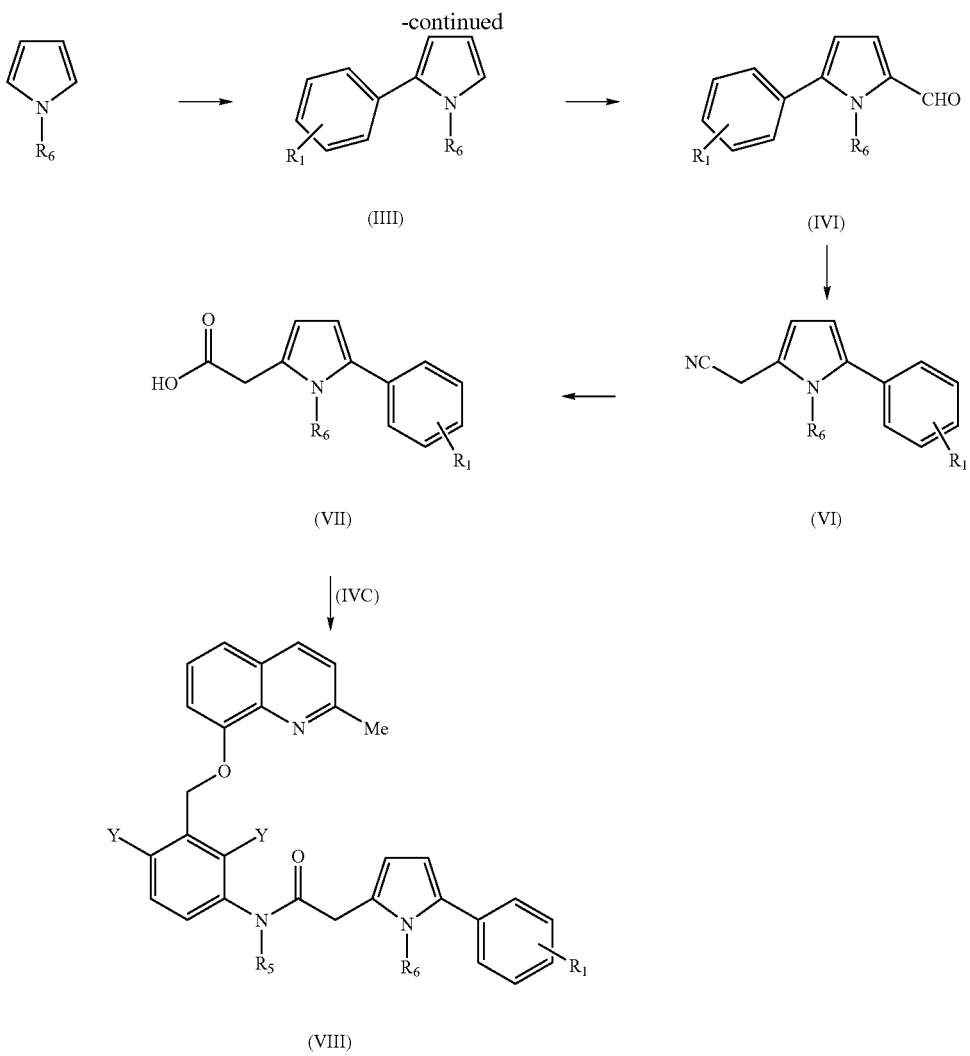

More specifically, the compound of formula (II), prepared by literature methods (Kruse et al *Heterocycles* 1987, 26, 3141-3151), was reacted with an ammonia salt such as ammonium acetate in a solvent such as ethanol or methanol or the like at an elevated temperature, preferably at a temperature in the range of 70-100° C. to yield the corresponding compound of formula (III).

The compound of formula (III) was reacted with a strong base such as sodium hydride, potassium hydride, sodium hydroxide, potassium hydroxide and the like in a solvent such as ether, THF, DMF and the like followed by reaction with an alkylating agent such as an alkyl, allyl or benzyl halide, or alkyl, allyl or benzylsulfonate and the like to yield the corresponding compound of formula (IIII).

Alternatively, 1-methyl(alkyl)pyrrole (purchased from Aldrich Chemicals), was reacted with a bromo- or iodo-substituted aryl or heteroaryl substrate in the presence of a strong base such as t-butyl lithium and a palladium catalyst such as dichloropalladium(1,1'-bis(diphenylphosphine)ferrocene ($PdCl_2$(dppf)) or dichloropalladium(1,4-bis(diphenylphosphine)butane (PdCl2(dppb)) in a solvent such as THF, ether and the like at a temperature from −78° C. to room temperature to yield the corresponding compound of formula (IIII).

The reagent formed by the reaction of dimethylformamide and a chlorinating agent such as oxalyl chloride or phosphorous oxychloride in a solvent such as ether or THF and the like at a temperature of 0° C. to room temperature was reacted with the compound of formula (IIII), prepared by either of the above methods to yield the compound of formula (IVI).

The compound of formula (IVI) was reacted with the reagent tosylmethylisocyanide (TosMIC) in the presence of a strong base such as potassium t-butoxide or sodium t-butoxide in a solvent such as dimethoxyethane or THF and the like at a temperature in the range of −45° C. to 100° C. to yield the corresponding compound of formula (VI).

The compound of formula (VI) was hydrolyzed by reaction with suitable base such as sodium hydroxide, potassium hydroxide and the like in a solvent such as ethanol, methanol, aqueous tetrahydrofuran and the like, at an elevated temperature, preferably a temperature in the range of about 70-100° C. to yield the corresponding compound of formula (VII).

The compound of formula (VII) was reacted with the compound of formula (IVC), the synthesis of which is described in Scheme A and Scheme B, with a suitable coupling agent such as HATU, HBTU, 1,1'-carbonyl diimidazole and the like in the presence of an organic base such as diisopropylethylamine or triethylamine and the like, in a suitable solvent such as methylene chloride, dichloroethane, DMF and the like, to yield the corresponding compound of formula (VIII).

Scheme J

Certain target compounds of the present invention may be prepared according to the process outlined in Scheme J below.

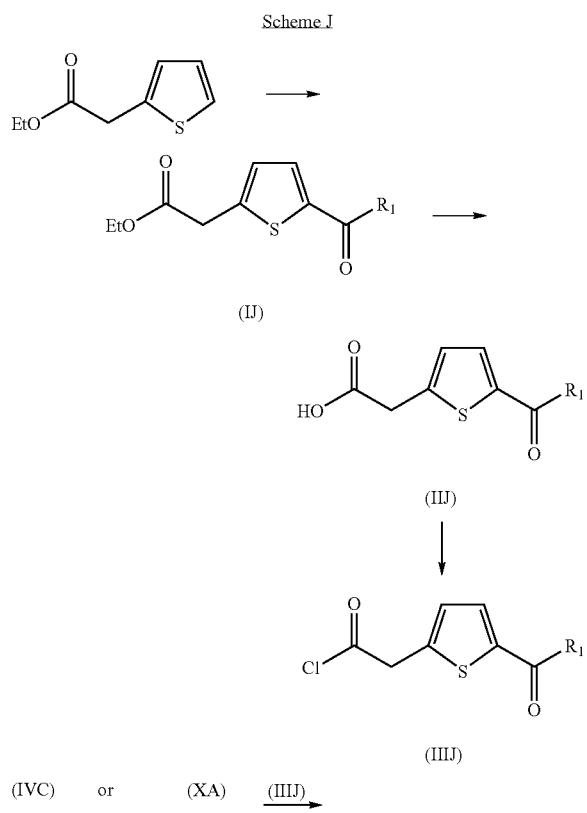

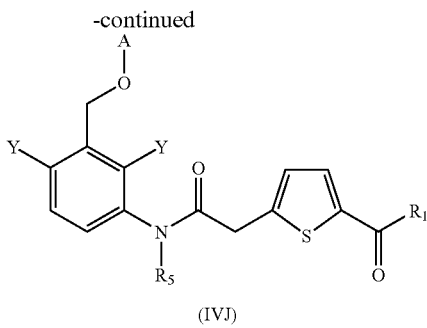

More specifically, ethyl-2-thiopheneacetate (purchased from Aldrich Chemicals) was reacted in the presence of an appropriately substituted acid chloride in the presence of a Lewis acid catalyst such as tin (IV) chloride, aluminum chloride, boron trifluoride-etherate and the like in a solvent such as benzene, toluene and the like at ambient temperature to yield the corresponding compound of formula (IJ).

The compound of formula (IJ) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (IIJ).

The compound of formula (IIJ) was reacted with a chlorinating agent such as oxalyl chloride or thionyl chloride in the presence of an acylation catalyst such as DMF in a suitable solvent such as methylene chloride, chloroform or dichloroethane and the like at a temperature of about 0° C. to yield the corresponding compound of formula (IIIJ).

The compound of formula (IIIJ) was reacted with the compound of formula (IVC) or (XA), the synthesis of which is described in Scheme A and C, in the presence of an organic base such as diisopropylethylamine or triethylamine and the like, in a suitable solvent such as methylene chloride, dichloroethane, DMF and the like, to yield the corresponding compound of formula (IVJ).

Scheme K

Certain target compounds of the present invention may be prepared according to the process outlined in Scheme K below.

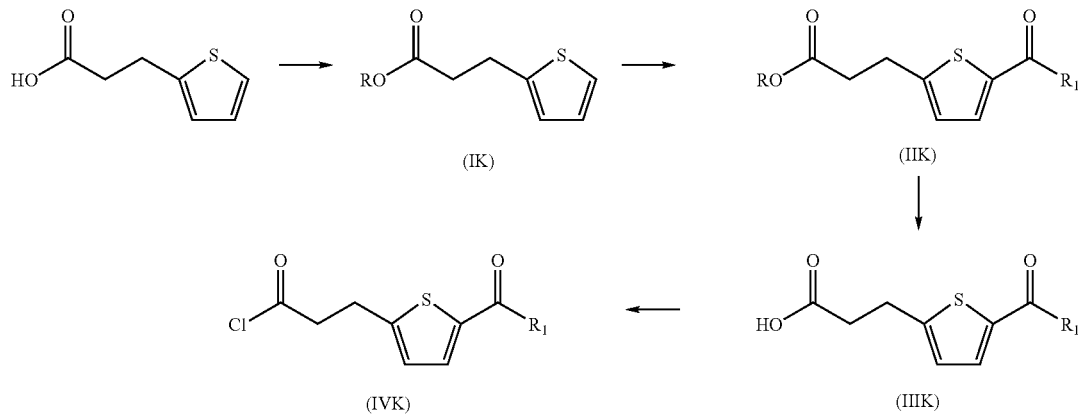

(IVC) or (XA) →(IVK)

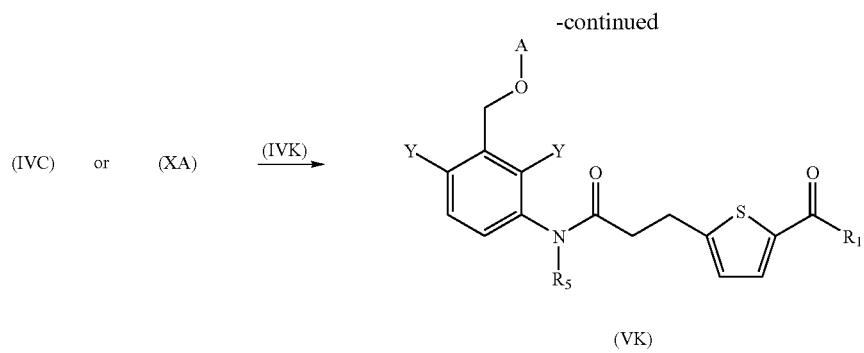

(VK)

More specifically, 2-thiophenepropionic acid (purchased from Aldrich Chemicals) was reacted with an acid such as sulfuric acid in a solvent such as ethanol, methanol and the like to yield the corresponding compound of formula (IK).

The compound of formula (IK) was reacted with an appropriately substituted acid chloride in the presence of a Lewis acid catalyst such as tin (IV) chloride, aluminum chloride, boron trifluoride-etherate and the like in a solvent such as benzene, toluene and the like at ambient temperature to yield the corresponding compound of formula (IIK).

The compound of formula (IIK) was saponified by reaction with suitable base such as sodium hydroxide, potassium hydroxide, lithium hydroxide, sodium carbonate, potassium carbonate and the like in a solvent such as ethanol, methanol, aqueous tetrahydrofuran and the like, at a temperature from ambient temperature to a temperature of about 70-100° C. to yield the corresponding compound of formula (IIIK).

The compound of formula (IIIK) was reacted with a chlorinating agent such as oxalyl chloride or thionyl chloride in the presence of an acylation catalyst such as DMF in a suitable solvent such as methylene chloride, chloroform or dichloroethane and the like at a temperature of about 0° C. to yield the corresponding compound of formula (IVK).

The compound of formula (IVK) was reacted with the compound of formula (IVC) or (XA), the synthesis of which is described in Scheme A and Scheme C, in the presence of an organic base such as diisopropylethylamine or triethylamine and the like, in a suitable solvent such as methylene chloride, dichloroethane, DMF and the like, to yield the corresponding compound of formula (VK).

Scheme L

Certain target compounds of the present invention may be prepared according to the process outlined in Scheme L below.

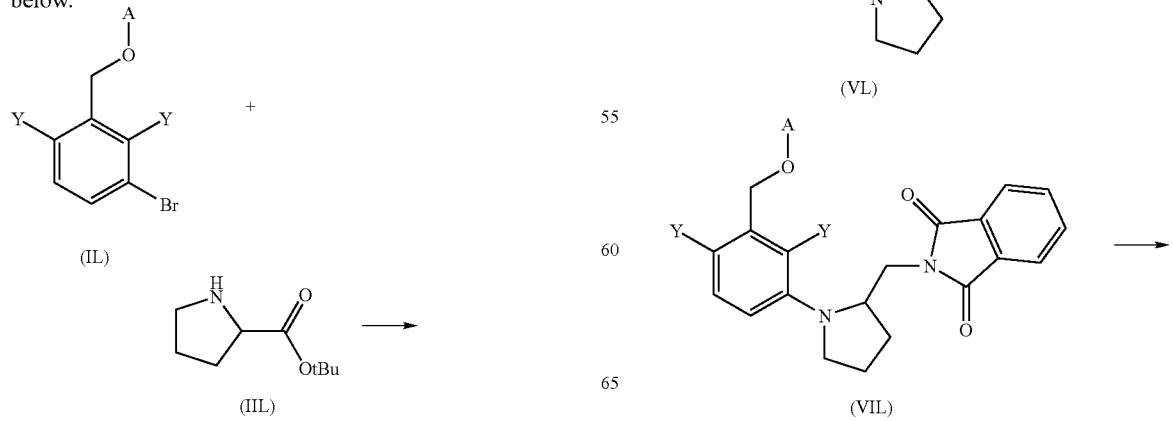

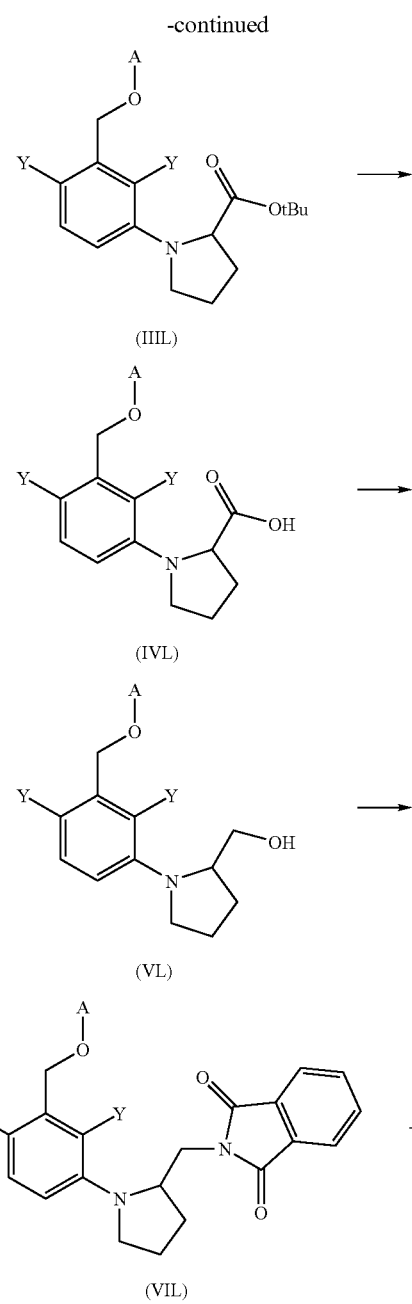

-continued

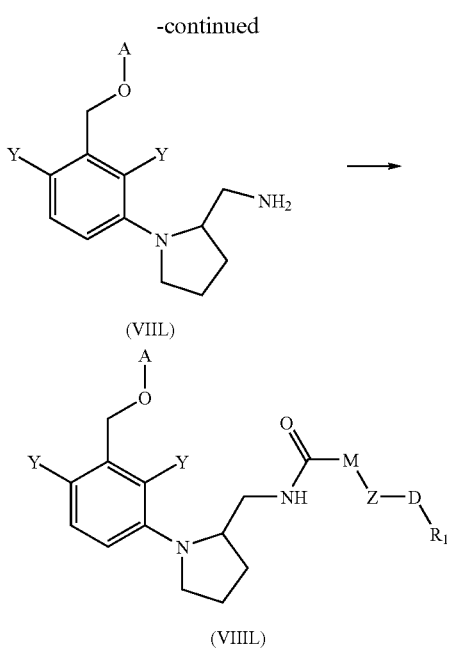

More specifically, the compound of formula (IL), prepared as outlined in previous schemes, underwent a Buchwald amination reaction with a compound of formula (IIL) in the presence of a base such as NaOtBu and the like, with a phosphine additive such as tBu₃P and the like, in the presence of a palladium catalyst such as Pd₂(dba)₃ and the like, to give a compound of formula (IIIL).

A compound of formula (IIIL) was then treated with a strong acid such as trfifluoroacetic acid and the like, in the presence of a chlorinated solvent such as methylene chloride and the like to give a compound of formula (IVL).

A compound of formula (IVL) was then reduced by first reaction with a chlorofomate such as isobutylchloroformate and the like, in the presence of an amine such as triethylamine and the like, followed by addition of a reducing agent such as NaBH₄ and the like to give a compound of formula (VL).

A compound of formula (VL) then underwent a Mitsunobu reaction with phthalimide in the presence of a phosphine additive such as nBu₃P and the like, also in the presence of an azodicarboxamide such as N,N,N',N'-tetramethylazodicarboxamide and the like to give a compound of formula (VIL).

A compound of formula (VIL) was then deprotected to the primary amine by reaction with hydrazine to give a compound of formula (VIIL).

A compound of formula (VIIL) was then acylated with a compound of formula R₁-D-Z-M-CO₂H, prepared as described in the schemes above, using peptide coupling methods known to those skilled in the art to provide a compound of formula (VIIIL).

SPECIFIC SYNTHETIC EXAMPLES

Specific compounds which are representative of the invention may be prepared as per the following examples offered by way of illustration and not by way of limitation. No attempt has been made to optimize the yields obtained in any of the reactions. One skilled in the art would know how to increase such yields through routine variations in reaction times, temperatures, solvents and/or reagents.

Unless otherwise indicated, ¹H NMR's were run on a Bruker AC-300 instrument. Mass spectral analyses were performed on a Fisons instrument (Hewlett-Packard HPLC driven electrospray MS instrument).

Preparation of A Piece Intermediates

8-[(3-N-methylamino-2,6-dichlorobenzyl)oxy]-2-methyl quinoline

A. 2,6-Dichloro-3-nitrotoluene (53.13 g, 257.9 mmol) was dissolved in 400 mL carbon tetrachloride. A reflux condenser was installed and the mixture was illuminated with a 150 W lamp which warmed the solution to reflux. NBS (120.64 g, 677.8 mmol) and 70% benzoyl peroxide (1.021 g, 2.95 mmol) were added to the reaction in 4 portions over the next 7 days. After cooling the reaction mixture was filtered off and the filtrate was washed 4 times with 100 mL brine, dried with Na₂SO₄, filtered, and concentrated to yield the corresponding bromide (74.132 g) as a yellow waxy solid. ¹H NMR (CDCl₃) δ 7.74 (d, 1H), 7.50 (d, 1H), 4.81 (s, 2H).

B. Ether washed 60% sodium hydride (2.54 g, 63.5 mmol) was suspended in 40 mL anhydrous DMF. The mixture was cooled on an ice bath and 8-hydroxy quinaldine (8.00 g, 50.3 mmol) was carefully added and the yellow mixture was allowed to stir for 10 minutes. The product prepared in step A (15.12 g, 53.1 mmol) was added to the reaction and was allowed to stir for 1.5 hours. The reaction was then diluted with 1.8 L water and the resulting solid was filtered off, rinsed twice with 50 mL ether, four times with 15 mL methanol, and air dried to yield the quinolinyl ether (15.271 g, 42.0 mmol) as a tan powder. ¹H NMR (CDCl₃) δ 8.03 (d, 1H), 7.77 (d, 1H), 7.55-7.36 (m, 3H), 7.35-7.21 (m, 2H), 5.69 (s, 2H), 2.76 (s, 3H); MS: M+1=363.

C. The product prepared in step B (15.22 g, 41.9 mmol) was dissolved in 200 mL concentrated HCl. A solution of stannous chloride (40.07 g, 211.3 mmol) in 200 mL concentrated HCl was prepared and added dropwise into the reaction over a 25 minute period. After 15 hours the reaction was diluted with 400 mL water and the solid was filtered off. The solid was suspended in 300 mL water and treated with 1N NaOH until the solution is basic. The solid is then filtered off and rinsed with water and 50 mL methylene chloride and dried under vacuum at 50° C. to yield the aniline product (12.999 g, 39.0 mmol) as an off-white powder. ¹H NMR (d6-DMSO) δ 8.20 (d, 1H), 7.54-7.34 (m, 4H), 7.25 (d, 1H), 6.92 (d, 1H), 5.71 (s, 2H), 5.36 (s, 2H), 2.62 (s, 3H); MS: M+1=333.

D. The product prepared in step C (1.001 g, 3.00 mmol) was suspended in 20 mL triethyl orthoformate with 2 mL trifluoroacetic acid. The mixture was refluxed for 16 hours and was then diluted with 30 mL ethanol and while continuing refluxing was treated with 2~400 mg tablets of sodium borohydride over the next 9 hours. The mixture was then concentrated, triturated with 100 mL water, filtered, and rinsed with 5 mL methanol. The solid was dried under vacuum at 50° C. to yield the title product (0.996 g, 2.87 mmol) as a dark tan powder. ¹H NMR (CDCl₃) δ 7.99 (d, 1H), 7.43-7.31 (m, 2H), 7.30-7.16 (m, 3H), 6.62 (d, 1H), 5.60 (s, 2H), 4.52 (br d, 1H), 2.92 (d, 3H), 2.73 (s, 3H); MS: M+1=347.

8-[(3-N-methylamino-2,6-dimethylbenzyl)oxy]-2-methyl quinoline

A. 2,6-Dimethylbenzoic acid (41.48 g, 276.2 mmol) was suspended in an ice bath cooled mixture of 50 mL concentrated sulfuric acid and 125 mL glacial acetic acid. A solution of 25 mL concentrated sulfuric acid and 25 mL concentrated nitric acid was dripped into the reaction over 35 minutes. 40 minutes after the addition the ice bath was removed and the reaction was allowed to stir at ambient temperature for 19 hours. The reaction was diluted with ice water to bring the volume to 2 L and the resulting solid was filtered off and rinsed twice with water. The solid was dried under vacuum at 55° C. to yield the corresponding nitro product (50.42 g, 258.3 mmol) as an off-white powder.

B. A solution of benzyltriethylammonium borohydride (24.41 g, 117.8 mmol) in 150 mL methylene chloride cooled on an ice bath and was carefully treated with a solution of trimethylsilyl chloride, (15.0 mL, 118.2 mmol) in 40 mL methylene chloride. To the resulting solution was then added a suspension of the product obtained in step A, (11.56 g, 59.2 mmol), in 100 mL methylene chloride. After the addition the ice bath was removed and the solution stirred for 9 hours and was then diluted with 50 mL methylene chloride and washed three times with 100 mL saturated $NaHCO_3$ and once with 100 mL brine. The organics were dried with $MgSO_4$, filtered, concentrated, and triturated with 100 mL hexanes. The solid was filtered off and dried under vacuum to yield the alcohol product (9.319 g, 51.4 mmol) as a white powder.

C. The product obtained in step B (4.56 g, 25.2 mmol) was suspended in 75 mL benzene. The 8-hydroxy quinaldine (4.94 g, 31.0 mmol) was added to the reaction and cooled on an ice bath. Tributylphosphine ($Bu_3P$), (7.6 mL, 30.4 mmol) and ADDP (7.79 g, 30.9 mmol) were then added to the reaction and the ice bath was removed after 15 minutes. The reaction was stirred for 14 hours and was then concentrated. The residue was taken up in 500 mL methylene chloride and washed four times with 100 mL 1N NaOH and once with 150 mL brine. The organics were dried with $MgSO_4$, concentrated, and purified via silica gel chromatography eluting with methylene chloride. The proper fractions were concentrated and the residue triturated with 10 mL methanol, filtered, rinsed with a little more methanol, and dried under vacuum to yield the coupled product (5.934 g, 18.4 mmol) as a cream-colored powder.

D. The product obtained in step C (4.89 g, 15.2 mmol) was dissolved in 50 mL concentrated HCl. A solution of stannous chloride (14.57 g, 76.8 mmol) in 25 mL concentrated HCl was prepared and added to the reaction dropwise over ~2 minutes. After 18 hours the reaction was diluted with 800 mL ice water and basified with 100 mL 50% NaOH. The resulting solid is then filtered off, rinsed once with 1N NaOH and twice with water, triturated with 20 mL EtOAc and dried under vacuum at 50° C. to yield the corresponding amino compound (4.088 g, 14.0 mmol) as an off-white powder.

E. The product obtained in step D (1.49 g, 5.13 mmol) was suspended in 15 mL methanol along with sodium methoxide (1.398 g, 25.9 mmol) and paraformaldehyde (1.54 g, 51.5 mmol). The mixture was heated at reflux for 19 hours. Then over the next 26 hours 5~400 mg tablets of $NaBH_4$ were added to the refluxing reaction. The reaction was then concentrated and the residue triturated with water and dried under vacuum at 40° C. to yield the methylamino product (1.471 g, 4.80 mmol) as a tan powder.

F. Alternatively, the product obtained in step B (5.44 g, 30.0 mmol) was dissolved in 100 mL methylene chloride. Triethylamine (6.68 g, 9.2 mL, 66.0 mmol) was added followed by the dropwise addition of methanesulfonyl chloride (3.78 g, 2.55 mL, 33.0 mmol). The reaction mixture was stirred at room temperature for 2 hours. The reaction mixture was washed with 75 mL $NaHCO_3$, then with 75 mL brine, dried over $Na_2SO_4$ and evaporated in vacuo. The residue was not further purified. The mesylate was obtained as a dark oil (7.0 g, 27.0 mmol).

G. The 8-hydroxyquinaidine (4.35 g, 30.0 mmol) was added to a slurry of hexane-washed 60% sodium hydride (1.32 g, 33.0 mmol) in 50 mL THF. The reaction mixture was stirred at room temperature for 45 minutes. The product obtained in step F (7.0 g, 27.0 mmol) was added to the reaction mixture and it was stirred at room temperature for 2 hours. The reaction mixture was evaporated in vacuo. The residue was dissolved in 50 mL of methylene chloride, washed with 50 mL $NaHCO_3$, then with 50 mL brine, dried over $Na_2SO_4$ and evaporated in vacuo. The product was purified by chromatography on silica gel eluting with 50:50 EtOAc:hexanes. The coupled product was obtained as a light yellow powder (6.4 g, 20.0 mmol). MS: M+1=323

H. The product obtained in step G (6.1 g, 19.0 mmol) was reduced as described in step D above. The amino was obtained as an off-white powder (4.1 g, 14.0 mmol). MS: M+1=293.

I. The product obtained in step H (2.92 g, 10.0 mmol) was dissolved in 30 mL chloroform. Trifluoroacetic anhydride (2.31 g, 1.55 mL, 11.0 mmol) was added to the solution dropwise and the reaction mixture was stirred at room temperature for 1 hour. The reaction mixture was washed with 30 mL $NaHCO_3$, 30 mL brine, dried over $Na_2SO_4$ and evaporated in vacuo. The trifluoroacetamide was obtained as a light yellow powder (3.69 g, 9.5 mmol). MS: M+1=389.

J. The product obtained in step I (3.5 g, 9.0 mmol) was added to a slurry of hexane-washed 60% sodium hydride in 15 mL DMF. Methyl iodide (1.41 g, 0.62 mL, 9.9 mmol) was added and the reaction mixture was stirred at room temperature for 2 hours. The reaction mixture was poured into100 mL water and the product was collected by filtration. The product was then washed twice with 20 mL water and obtained as light yellow powder (3.26 g, 8.1 mmol). MS: M+1=403.

K. The product obtained in step J (3.22 g, 8.0 mmol) was dissolved in 20 mL methanol and sodium borohydride (8.9 mmol, ~0.4 g) was carefully added. The reaction mixture was stirred at room temperature for 2 hours. The reaction mixture was concentrated in vacuo to approximately half its original volume. The product precipitated and was collected by filtration. The title product was obtained as a cream-colored powder (1.96 g, 6.4 mmol). $^1H$ NMR ($CDCl_3$) δ 8.0 (d, 1H), 7.1-7.4 (m, 5H), 6.6 (d, 1H), 5.3 (s, 2H), 2.9 (s, 3H), 2.7 (s, 3H), 2.4 (s, 3H), 2.1 (s, 3H); MS: M+1=306.

8-[(3-N-ethylamino-2,6-dimethylbenzyl)oxy]-2-methyl quinoline

The title compound was synthesized in a manner analogous to that described above for 8-[(3-N-methylamino-2,6-dimethylbenzyl)oxy]-2-methyl quinoline except that ethyl iodide was used instead of methyl iodide in step J. $^1H$ NMR ($CDCl_3$): δ 8.0 (d, 1H), 7.1-7.4 (m, 5H), 6.6 (d, 1H), 5.3 (s, 2H), 3.2 (q, 2H), 2.8 (s, 3H), 2.3 (s, 3H), 2.1 (s, 3H), 1.3 (t, 3H); MS: M+1=307.

8-[(3-N-ethylamino-2,6-dichlorobenzyl)oxy]-2-methyl quinoline

The title compound was synthesized in a manner analogous to that described above for 8-[(3-N-methylamino-2,6- dimethylbenzyl)oxy]-2-methyl quinoline except that the 2,6-dichloro quinoline intermediate was used instead of the 2,6-dimethyl quinoline intermediate. Also ethyl iodide was used in place of methyl iodide in step J. $^1$H NMR (CDCl$_3$): δ 8.2 (d, 1H), 7.5 (m, 6H), 5.4 (s, 2H), 3.7 (m, 2H), 2.7 (s, 3H), 1.25 (t, 3H); MS: M+1=361.

8-[(3-N-propylamino-2,6-dichlorobenzyl)oxy]-2-methyl quinoline

The title compound was synthesized in a manner analogous to that described above for 8-[(3-N-methylamino-2,6-dimethylbenzyl)oxy]-2-methyl quinoline except that the 2,6-dichloro quinoline intermediate was used instead of the 2,6-dimethyl quinoline intermediate. Also n-propyl iodide was used in place of methyl iodide in step J. $^1$H NMR (CDCl$_3$): δ 8.1 (d, 1H), 7.2-7.6 (m, 5H), 6.6 (d, 2H), 5.6 (s, 2H), 4.4 (t, 1H), 3.2 (q, 2H), 2.8 (s, 3H), 1.7 (m, 2H), 1.0 (t, 3H); MS: M+1=335.

8-[(3-N-allylamino-2,6-dichlorobenzyl)oxy]-2-methyl quinoline

The title compound was synthesized in a manner analogous to that described above for 8-[(3-N-methylamino-2,6-dimethylbenzyl)oxy]-2-methyl quinoline except that the 2,6-dichloro quinoline intermediate was used instead of the 2,6-dimethyl quinoline intermediate. Also allyl iodide was used in place of methyl iodide in step J. MS: M+1=333.

8-[(3-N-methyl-2,6-dichlorobenzyl)oxy]-3-bromo-2-methylimidazo[1,2-a]pyridine 8-[(3-amino-2,6-dichlorobenzyl)oxy]-3-bromo-2-methylimidazo[1,2-a]pyridine, prepared by literature methods, (Kayakiri et al, *J. Med. Chem.* 1998, 41, 564-78). 1.213 g, 3.02 mmol, was suspended in 20 mL triethyl orthoformate with ~2 ml trifluoroacetic acid. The mixture was refluxed for 13.5 hours and was then diluted with 30 mL ethanol. While continuing to heat at reflux, the reaction mixture was treated with 2~400 mg tablets of sodium borohydride over the next 2.5 hours. The mixture was then concentrated, triturated with 100 mL water, filtered, and rinsed three times with 2 mL methanol. The solid was dried under vacuum to yield the title product (1.130 g, 2.72 mmol) as a tan powder. $^1$H NMR (CDCl$_3$): δ 7.72 (d, 1H), 7.24 (d, 1H), 6.82 (t, 1H), 6.71 (d, 1H), 6.63 (d, 1H), 5.45 (s, 2H), 4.47 (br m, 1H), 2.93 (d, 3H), 2.48 (s, 3H); MS: M+1=414.

Example 1

N-[2,4-Dichloro-3-(2-methyl-quinolin-8-yloxymethyl)-phenyl]-N-methyl-2-[1-methyl-5-(3-methyl-4-nitro-benzoyl)-1H-pyrrol-2-yl]-acetamide
(Compound 65)

A. 3-Methyl-4-nitrobenzoic acid (5.436 g, 30.0 mmol) was suspended in thionyl chloride (30 mL, 411 mmol). The flask was equipped with a reflux condenser and a drying tube. The mixture was heated at reflux for 15 hours. The excess thionyl chloride was removed in vacuo. The residue was taken up in toluene and again the solvents were removed in vacuo to yield the corresponding acid chloride as a yellow oil, contaminated with 9% toluene (6.261 g).
B. The acid chloride prepared in step A (5.70 g, 28.6 mmol) was dissolved in 35 mL toluene and put into a 3-neck flask. Methyl-N-methyl-2-pyrroleacetate (3.5 mL, 24.3 mmol) was added to the reaction. The flask was equipped with a reflux condenser and a nitrogen bubbler. Nitrogen was gently bubbled through the reaction as it was heated at reflux for 18 hours. The reaction was then diluted with 30 mL toluene and poured into a solution of 20 mL 3-(diethylamino)propylamine in 200 mL water. This was shaken then extracted with 200 mL chloroform. The organics were washed 3 times with 100 mL 1N HCl. The organics were dried with MgSO$_4$, treated with charcoal then filtered and the solvents removed in vacuo. The residue was triturated with 25 mL methanol, filtered, and rinsed once with 10 mL methanol. The solid was dried under vacuum to yield the pyrrolyl ester (5.740 g, 18.1 mmol) as a yellow-brown powder.
C. The pyrrolyl ester prepared in step B (1.579 g, 4.99 mmol) was suspended in 25 mL ethanol and then heated to reflux. When refluxing, 1N NaOH solution (5.0 mL, 5.0 mmol) was added to the reaction over 6 minutes. The reaction was allowed to continue refluxing for an additional 30 minutes. After cooling the solvents were removed in vacuo. The residue was then dissolved in 50 mL water and acidified with excess 1N HCl. The resulting solid was filtered off and rinsed with water and then dried under vacuum at 50° C. to yield the corresponding carboxylic acid (1.407 g, 4.65 mmol) as a tan powder.
D. The carboxylic acid prepared in step C (0.304 g, 1.01 mmol) was dissolved in 15 mL methylene chloride. One drop of DMF was added and the reaction was cooled on an ice bath under a nitrogen atmosphere. Oxalyl chloride (0.26 mL, 3.0 mmol) was added and the reaction was allowed to stir for 2.5 hours. The organics were then evaporated under a stream of nitrogen while still on the ice bath. The resulting residue was dried under vacuum and carried on as-is as soon as possible.
E. The product prepared in step D (assume 1.01 mmol) was dissolved in 15 mL methylene chloride. 8-[3-N-methylamino-2,6-dichlorobenzyl)oxy]-2-methyl quinoline, prepared as described above, (0.182 g, 0.524 mmol) was added to the reaction and the solution was allowed to stir under nitrogen for 15.5 hours. The reaction was then quenched by addition of a few drops of water. The solvents were then removed in vacuo and the residue dissolved in methylene chloride and treated with diisopropylethylamine followed by evaporation of the solvents in vacuo. The residue was purified via silica gel chromatography eluting with 60% EtOAc/40% hexanes. The proper fractions were isolated and the organics were removed in vacuo to yield the title product (0.185 g, 0.293 mmol) as a yellow powder. $^1$H NMR (CDCl$_3$): δ 7.99 (d, 1H), 7.91 (d, 1H), 7.65 (m, 2H), 7.52-7.34 (m, 3H), 7.33-7.17 (m, 3H), 6.62 (d, 1H), 5.84 (d, 1H), 5.67 (s, 2H), 3.88 (s, 3H), 3.43 (s, 2H), 3.23 (s, 3H), 2.68 (s, 3H), 2.60 (s, 3H); MS: M+1=631.

Example 2

N-[2,4-Dichloro-3-(2-methyl-quinolin-8-yloxymethyl)-phenyl]-N-methyl-2-[1-methyl-5-(pyridine-4-carbonyl)-1H-pyrrol-2-yl]-acetamide
(Compound 60)

A. 4-Isonicotinoyl chloride hydrochloride (6.43 g, 36.1 mmol) was suspended in 50 mL toluene in a 3-neck flask. Methyl-N-methyl-2-pyrroleacetate (4.3 mL, 29.9 mmol) was added to the reaction. The flask was equipped with a reflux condenser and a nitrogen bubbler. Nitrogen was gently bubbled through the reaction as it was heated at reflux for 14.5 hours. The reaction was then diluted with 200 mL chloroform and washed once with 200 mL 10% Na$_2$CO$_3$ solution. The organics were dried with MgSO$_4$ and treated with charcoal then filtered and the solvents removed in vacuo. The residue was triturated with 120 mL 5:1 hexanes:EtOAc. The solid was then filtered off and air-dried to yield the pyrrolyl ester (6.170 g, 23.9 mmol) as a brown powder.

B. The product prepared in step A (1.293 g, 5.01 mmol) was dissolved in 50 mL 1:1 THF:water. Lithium hydroxide monohydrate (0.210 g, 5.00 mmol) was then added to the reaction and was stirred for 2.5 hours. The reaction was then concentrated in vacuo until the organics have been removed. An additional 50 mL water was added to the reaction solution followed by 1N HCl (5.0 mL, 5.0 mmol). The resulting solid was filtered off and rinsed with water. It was then dried under vacuum at 50° C. to yield the corresponding carboxylic acid (0.897 g, 3.67 mmol) as a brown powder.

C. The product prepared in step B (0.148 g, 0.606 mmol) was suspended in 10 mL methylene chloride. One drop of DMF was added and the reaction was cooled on an ice bath under a nitrogen atmosphere. Oxalyl chloride (0.16 mL, 1.8 mmol) was added and the reaction was allowed to stir for 1.5 hours. The organics were then evaporated under a stream of nitrogen while still on the ice bath. The resulting residue was dried under vacuum and carried on as-is as soon as possible.

D. The product prepared in step C (assume 0.606 mmol) was dissolved in 10 mL methylene chloride. 8-[3-N-methylamino-2,6-dichlorobenzyl)oxy]-2-methyl quinoline, prepared as described above, (0.106 g, 0.305 mmol) was added to the reaction and the solution was allowed to stir under nitrogen for 2.5 hours. The reaction was then quenched by addition of a few drops of water. The solvents were then removed in vacuo and the residue dissolved in methylene chloride/methanol and treated with diisopropylethylamine followed by evaporation of the solvents in vacuo. The residue was purified via silica gel chromatography eluting with 90% EtOAc/10% acetone. The proper fractions were isolated and the organics were removed in vacuo to yield the title product (0.115 g, 0.201 mmol) as a yellow powder. $^1$H NMR (CDCl$_3$) δ 8.68 (d, 2H), 8.02 (d, 1H), 7.54 (d, 2H), 7.51-7.33 (m, 3H), 7.32-7.16 (m, 3H), 6.62 (d, 1H), 5.88 (d, 1H), 5.69 (s, 2H), 3.88 (s, 3H), 3.42 (d, 2H), 3.23 (s, 3H), 2.70 (s, 3H); MS M+1=573.

Example 3

2-[5-(6-Chloro-pyridine-3-carbonyl)-1-methyl-1H-pyrrol-2-yl]-N-[2,4-dichloro-3-(2-methyl-quinolin-8-yloxymethyl)-phenyl]-N-methyl-acetamide (Compound 67)

A. 6-Chloronicotinoyl chloride (21.14 g, 120.1 mmol) was suspended in 100 mL toluene in a 3-neck flask. Methyl-N-methyl-2-pyrroleacetate (15.0 mL, 104.2 mmol) was added to the reaction. The flask was equipped with a reflux condenser and a nitrogen bubbler. Nitrogen was gently bubbled through the reaction as it was heated at 105° C. for 19 hours. The reaction was then diluted with 400 mL chloroform and washed once with 400 mL 10% Na$_2$CO$_3$ solution and twice with 200 mL 10% Na$_2$CO$_3$ solution. The organics were dried with MgSO$_4$ and treated with charcoal then filtered and concentrated. The residue was triturated with 50 mL methanol, filtered, and rinsed twice more with 25 mL methanol. The solid was then dried under vacuum to yield the pyrrolyl ester (20.88 g, 71.3 mmol) as a tan powder.

B. The product prepared in step A (20.88 g, 71.3 mmol) was suspended in 300 mL 5:1 THF:water. Lithium hydroxide monohydrate (3.148 g, 75.0 mmol) was then added to the reaction and was stirred over the weekend. The reaction was then concentrated in vacuo until the organics have been removed. Water was added to the residue to bring the volume to 400 mL followed by 1N HCl (75.0 mL, 75.0 mmol). The resulting solid was filtered off and dried under vacuum at 50° C. to yield the corresponding carboxylic acid (19.325 g, 69.3 mmol) as a light tan powder.

C. The product prepared in step B (2.789 g, 10.01 mmol) was dissolved in 100 mL methylene chloride. Five drops of DMF was added and the reaction was cooled on an ice bath under a nitrogen atmosphere. Oxalyl chloride (2.6 mL, 29.8 mmol) was added and the reaction was allowed to stir for 30 minutes. The organics were then evaporated under a stream of nitrogen while still on the ice bath. The resulting residue was dried under vacuum and carried on as-is as soon as possible.

D. The product prepared in step C (assume 10.01 mmol) was dissolved in 100 mL methylene chloride. The 8-[3-N-methylamino-2,6-dichlorobenzyl)oxy]-2-methyl quinoline, prepared as described above, (1.743 g, 5.02 mmol) and a little DMAP was added to the reaction and the solution was allowed to stir under nitrogen for 20 hours. The reaction was then quenched by addition of a few drops of water. The solvents were then removed in vacuo and the residue dissolved in methylene chloride/methanol and treated with diisopropylethylamine followed by concentration. The residue was purified via silica gel chromatography eluting with 75% EtOAc/25% hexanes. The proper fractions were isolated and concentrated and the material was dissolved in methylene chloride and treated with excess ethereal HCl. The solution was concentrated and dried under vacuum at 50° C. to yield the title product (2.41 g, 3.56 mmol) as a yellow powder. Elemental analysis calculated for C$_{31}$H$_{25}$Cl$_3$N$_4$O$_3$.1.6HCl.0.6H$_2$O: C, 55.00; H, 4.14; N, 8.28; Cl, 24.09; KF, 1.60. Found: C, 55.18; H, 4.08; N, 8.08; Cl, 24.15; KF, 1.63; $^1$H NMR (CDCl$_3$): δ 8.74 (s, 1H), 8.57 (br s, 1H), 8.02 (d, 1H), 7.77 (br t, 1H), 7.61 (t, 2H), 7.52 (m, 2H), 7.36 (dd, 2H), 6.59 (d, 1H), 6.06 (d, 1H), 5.66 (q, 2H), 3.97 (s, 3H), 3.79 (br q, 2H), 3.34 (s app, 6H); MS: M+1=607.

Example 4

N-[2,4-Dichloro-3-(2-methyl-quinolin-8-yloxymethyl)-phenyl]-2-(5-hexanoyl-1-methyl-1H-pyrrol-2-yl)-N-methyl-acetamide (Compound 23)

A. Hexanoyl chloride (6.4 mL, 45.8 mmol) and methyl-N-methyl-2-pyrroleacetate (4.4 mL, 30.6 mmol) were combined in 30 mL toluene in a 3-neck flask. The flask was equipped with a reflux condenser and a nitrogen bubbler. Nitrogen was gently bubbled through the reaction as it was heated at reflux for 17.5 hours. The reaction was then diluted with 20 mL toluene and poured into a solution of 20 mL 3-(diethylamino)propylamine in 200 mL water. This was shaken then extracted with 200 mL chloroform. The organics were washed 3 times with 100 mL 1N HCl. The organics were dried with MgSO$_4$, treated with charcoal then filtered and the solvents removed in vacuo. The residue was purified via silica gel chromatography eluting with 20% EtOAc/80% hexanes. The proper fractions were isolated and the organics were removed in vacuo to yield the pyrrolyl ester (5.999 g, 23.9 mmol) as an orange oil that slowly solidified.

B. The product prepared in step A (1.263 g, 5.03 mmol) was dissolved in 30 mL 5:1 THF:water. Lithium hydroxide monohydrate (0.213 g, 5.08 mmol) was then added to the reaction and was stirred for 16 hours. The solvents were then removed in vacuo and the residue dissolved in water. The solution was then acidified with excess 1N HCl. The resulting solid was filtered off and rinsed with water and then dried under vacuum at 50° C. to yield corresponding carboxylic acid (1.079 g, 4.55 mmol) as a pinkish powder.

C. The product prepared in step B (0.237 g, 1.00 mmol) was dissolved in 15 mL methylene chloride. One drop of DMF was added and the reaction was cooled on an ice bath under a nitrogen atmosphere. Oxalyl chloride (0.26 mL, 3.0 mmol) was added and the reaction was allowed to stir for 1 hour. The organics were then evaporated under a stream of nitrogen while still on the ice bath. The resulting residue was dried under vacuum and carried on as-is as soon as possible.

D. The product prepared in step C (assume 1.00 mmol) was dissolved in 15 mL methylene chloride. 8-[3-N-methylamino-2,6-dichlorobenzyl)oxy]-2-methyl quinoline, prepared as described above, (0.178 g, 0.513 mmol) was added to the reaction and the solution was allowed to stir under nitrogen for 1.5 hours. The reaction was then quenched by addition of a few drops of water. The solvents were then removed in vacuo and the residue dissolved in methylene chloride/methanol and treated with diisopropylethylamine followed by evaporation of the solvents in vacuo. The residue was purified via silica gel chromatography eluting with 60% EtOAc/40% hexanes. The proper fractions were isolated and the organics were removed in vacuo to yield the title product (0.172 g, 0.304 mmol) as an orange-yellow glassy solid. $^1$H NMR (CDCl$_3$): δ 8.00 (d, 1H), 7.48-7.31 (m, 4H), 7.30-7.12 (m, 2H), 6.88 (d, 1H), 5.78 (d, 1H), 5.67 (s, 2H), 3.76 (s, 3H), 3.34 (d, 2H), 3.21 (s, 3H), 2.78-2.61 (m, 5H), 1.67 (m, 2H), 1.32 (m, 4H), 0.90 (t, 3H); MS: M+1=566.

Example 5

N-[2,4-Dichloro-3-(2-methyl-quinolin-8-yloxymethyl)-phenyl]-2-[5-(4-methanesulfonyl-benzoyl)-1-methyl-1H-pyrrol-2-yl]-N-methyl-acetamide (Compound 75)

A. Compound 69 (1.388 g, 4.80 mmol) prepared by the general methods above was suspended in a slurry in 30 mL acetic acid. 30% Hydrogen peroxide (15 mL) was added and the reaction was allowed to stir for 18 hours. The now clear reaction mixture was diluted with 500 mL water and extracted three times with 150 mL chloroform. The combined organics were washed once with 150 mL brine then dried with MgSO$_4$ and filtered. The solvents were removed in vacuo to yield the methanesulfonyl product (1.325 g, 4.12 mmol) as an orange solid.

B. The product prepared in step A (1.285 g, 4.00 mmol) was dissolved in 50 mL methylene chloride. Two drops of DMF were added and the reaction was cooled in an ice bath under a nitrogen atmosphere. Oxalyl chloride (1.05 mL, 12.0 mmol) was added and the reaction was allowed to stir for 2.5 hours. The organics were then evaporated under a stream of nitrogen while still on the ice bath. The resulting residue was dried under vacuum and used immediately in the next step.

C. The product prepared in step B (assume 4.00 mmol) was dissolved in 50 mL methylene chloride. 8-[3-N-methylamino-2,6-dichlorobenzyl)oxy]-2-methyl quinoline, prepared as described above, (0.697 g, 2.01 mmol) was added to the reaction and the solution was allowed to stir under nitrogen for 40 minutes. The reaction was then quenched by addition of ~2 mL of isopropanol. The solvents were then removed in vacuo and the residue dissolved in methylene chloride and treated with trifluoroacetic acid followed by evaporation of the solvents in vacuo. The residue was purified first via reverse phase chromatography then by silica gel chromatography eluting with 90-100% EtOAc/hexanes. The proper fractions were isolated and the organics were removed in vacuo. The resulting residue was converted to its HCl salt by the addition of ethereal HCl followed by removal of the volatiles in vacuo to give the title product (0.830 g, 1.16 mmol) as a yellow powder. Elemental analysis calculated for $C_{33}H_{29}Cl_2N_3O_5S \cdot 1.0HCl \cdot 1.5H_2O$: C, 55.51; H, 4.66; N, 5.89. Found: C, 55.53; H, 4.31; N, 5.78; $^1$H NMR (CDCl$_3$): δ 8.63 (d, 1H), 8.00 (d, 2H), 7.91 (d, 2H), 7.80 (t, 1H), 7.64 (m, 2H), 7.53 (d, 2H), 7.37 (d, 1H), 6.54 (d, 1H), 6.08 (d, 1H), 5.68 (q, 2H), 4.01 (s, 3H), 3.87 (br q, 2H), 3.38 (s, 3H), 3.32 (s, 3H), 3.10 (s, 3H); MS: M+1=650.

Example 6

N-[2,4-Dichloro-3-(2-methyl-quinolin-8-yloxymethyl)-phenyl]-2-[5-(4-methanesulfinyl-benzoyl)-1-methyl-1H-pyrrol-2-yl]-N-methyl-acetamide (Compound 73)

Compound 69 (0.013 g, 0.018 mmol), prepared in the manner of compound 1, except that 4-thiomethylbenzoic acid was used instead of 3-methyl-4-nitrobenzoic acid, was dissolved in 2 mL acetic acid. Sodium perborate tetrahydrate (0.0043 g, 0.028 mmol) was added and the reaction was stirred for 6 hours. The entire reaction mixture was subjected to purification by reverse phase column chromatography eluting with a gradient of acetonitrile:water 10-90%. The proper fractions were isolated and the solvents were removed in vacuo to yield the title product (0.006 g, 0.008 mmol) as a yellow solid. $^1$H NMR (CDCl$_3$): δ 8.61 (d, 1H), 7.91 (d, 2H), 7.78 (t, 1H), 7.74-7.60 (m, 4H), 7.54 (t, 2H), 7.40 (d, 1H), 6.59 (d, 1H), 5.95 (d, 1H), 5.62 (s, 2H), 3.92 (s, 3H), 3.57 (d, 2H), 3.31 (s, 3H), 2.96 (s, 3H), 2.80 (s, 3H); MS: M+1=634.

Example 7

2-[5-(4-Amino-benzoyl)-1-methyl-1H-pyrrol-2-yl]-N-[2,4-dichloro-3-(2-methyl-quinolin-8-yloxymethyl)-phenyl]-N-methyl-acetamide (Compound 56)

Compound 63 (0.148 g, 0.202 mmol), prepared in the manner of compound 1, except that 4-nitrobenzoic acid was used instead of 3-methyl-4-nitrobenzoic acid, was dissolved in 5 mL concentrated HCl. A solution of stannous chloride (0.192 g, 1.01 mmol) in 5 mL concentrated HCl was added to the reaction dropwise over 3 minutes. The reaction was allowed to stir for 1.5 hours then was diluted with 90 mL water. This solution was treated with 10 mL 50% NaOH and the very finely divided product was extracted three times with 50 mL methylene chloride. The combined organics were dried with MgSO4, filtered, and the organics evaporated in vacuo. The residue was converted to the bis HCl salt by treatment with ethanolic HCl followed my removal of the organics in vacuo. This was then dried under vacuum at 50° C. to yield the product (0.082 g, 0.124 mmol) as a yellow powder. MS: M+1=587.

Example 8

2-[5-(4-Acetylamino-benzoyl)-1-methyl-1H-pyrrol-2-yl]-N-[2,4-dichloro-3-(2-methyl-quinolin-8-yloxymethyl)-phenyl]-N-methyl-acetamide (Compound 74)

Compound 56 (0.033 g, 0.056 mmol) was dissolved in 5 mL acetonitrile. To this was added diisopropylethylamine (0.032 mL, 0.184 mmol) and acetyl chloride (0.05 mL, 0.703 mmol). The reaction was allowed to stir for 2 hours then was quenched with the addition of ~2 ml of methanol. The solvents were evaporated and the residue purified via reverse phase chromatography eluting with a gradient of acetonitrile:water 10-90%.The proper fractions were isolated and the solvents were lyophilized to yield the product (0.021 g, 0.028 mmol) as an off-white powder. $^1$H NMR (CDCl$_3$): δ 8.61 (d, 1H), 7.84-7.47 (m, 9H), 7.37 (d, 1H), 6.55 (d, 1H), 5.86 (d, 1H), 5.60 (s, 2H), 3.84 (s, 3H), 3.53 (m, 2H), 3.28 (s, 3H), 2.93 (s, 3H), 2.21 (s, 3H); MS: M+1=629.

Example 9

N-[2,4-Dichloro-3-(2-methyl-quinolin-8-yloxymethyl)-phenyl]-2-[5-(4-dimethylamino-benzoyl)-1-methyl-1H-pyrrol-2-yl]-N-methyl-acetamide (Compound 115)

Compound 56 (0.035 g, 0.053 mmol) was dissolved in 5 mL methanol. The solution was refluxed and an excess of paraformaldehyde and sodium cyanoborohydride was added periodically over 4.5 hours. The reaction was evaporated in vacuo and the residue taken up in methylene chloride/methanol and acidified with concentrated HCl. The solvents were evaporated in vacuo and the residue purified via reverse phase chromatography eluting with a gradient of acetonitrile:water 10-90%.The proper fractions were isolated and the solvents were lyophilized to yield the title product (0.004 g, 0.005 mmol) as a yellow powder. MS: M+1=615

Example 10

4-[5-({[2,4-Dichloro-3-(2-methyl-quinolin-8-yloxymethyl)-phenyl]-methyl-carbamoyl}-methyl)-1-methyl-1H-pyrrole-2-carbonyl]-N,N-dimethyl-benzamide (Compound 62)

A. Compound 64 (0.315 g, 0.500 mmol), prepared in the manner of compound 1, except that terephthalic acid mono methyl ester was used instead of 3-methyl-4-nitrobenzoic acid, was dissolved in 5 mL ethanol and was heated to reflux. While refluxing 1N NaOH (0.60 mL, 0.60 mmol) was added dropwise over 2.5 minutes. This was then allowed to reflux for 1.5 hours. The reaction mixture was then concentrated in vacuo and carried on as-is.

B. The carboxylic acid prepared in step A (assume 0.500 mmol) was dissolved in 10 mL dimethylformamide, followed by the addition of dimethylamine hydrochloride (0.082 g, 1.01 mmol), diisopropylethylamine (0.261 mL, 1.50 mmol), and HBTU (0.194 g, 0.51 mmol). The reaction was stirred for 15 hours and was then quenched with the addition of ~2 ml of water. The solvents were then removed in vacuo and the residue dissolved in methylene chloride and treated with diisopropylethylamine followed by evaporation of the solvents in vacuo. The residue was purified via silica gel chromatography eluting with 90% EtOAc/10% acetone. The proper fractions were isolated and the organics were removed in vacuo to yield the title product (0.271 g, 0.421 mmol) as a light yellow powder. $^1$H NMR (CDCl$_3$): δ 8.01 (d, 1H), 7.78 (d, 2H), 7.52-7.09 (m, 8H), 6.58 (d, 1H), 5.86 (d, 1H), 5.68 (s, 2H), 3.87 (s, 3H), 3.40 (s, 2H), 3.21 (s, 3H), 3.12 (s, 3H), 3.01 (s, 3H), 2.71 (s, 3H); MS: M+1=643.

Example 11

N-[2,4-Dichloro-3-(2-methyl-quinolin-8-yloxymethyl)-phenyl]-N-methyl-2-[1-methyl-5-(4-pyrrolidin-1-ylmethyl-benzoyl)-1H-pyrrol-2-yl]-acetamide (Compound 46)

A. 4-Chloromethyl benzoyl chloride (5.78 g, 30.6 mmol) was dissolved in 30 mL toluene and put into a 3-neck flask. Methyl-N-methyl-2-pyrroleacetate (4.4 mL, 30.6 mmol) was added to the reaction. The flask was equipped with a reflux condenser and a nitrogen bubbler. Nitrogen was gently bubbled through the reaction as it was heated at reflux for 14 hours. The reaction was evaporated in vacuo and the residue was purified via silica gel chromatography eluting with 30% EtOAc/70% hexanes. The proper fractions were isolated and the organics were removed in vacuo to yield the pyrrolyl ester (1.366 g, 4.47 mmol) as a yellow solid.

B. The product prepared in step A (0.613 g, 2.00 mmol) was suspended in a mixture of 10 mL acetonitrile and 2 mL methylene chloride. Triethylamine (0.279 mL, 2.00 mmol) and pyrrolidine (0.167 mL, 2.00 mmol) was added to the reaction and allowed to stir for 7 hours at which time an additional amount of pyrrolidine was added (0.167 mL, 2.00 mmol). After stirring for an additional 16 hours the reaction was evaporated in vacuo. The residue was dissolved in 75 mL methylene chloride and washed three times with 25 mL saturated NaHCO$_3$ then dried with MgSO$_4$ and filtered. Evaporation of the solvents in vacuo yielded the corresponding pyrrolidinyl product (0.654 g, 1.92 mmol) as a yellow oil.

C. The product prepared in step B (0.618 g, 1.82 mmol) was dissolved in 30 mL 5:1 THF:water. Lithium hydroxide monohydrate (0.084 g, 2.00 mmol) was then added to the reaction and was stirred for 15 hours. 1N HCl (2.0 mL, 2.0 mmol) was then added to the reaction and the solvents were evaporated in vacuo. The residue was dissolved in water and washed three times with 50 mL methylene chloride. The aqueous layer was evaporated in vacuo and the solid dried under vacuum at 50° C. to yield the corresponding carboxylic acid as a yellow powder contaminated with 12% LiCl (0.603 g).

D. The product prepared in step C (assume 1.0 mmol) was dissolved in 15 mL methylene chloride and 2 mL acetonitrile. One drop of DMF was added and the reaction was cooled on an ice bath under a nitrogen atmosphere. Oxalyl chloride (0.26 mL, 3.0 mmol) was added and the reaction was allowed to stir for 4 hours. The organics were then evaporated under a stream of nitrogen while still on the ice bath. The resulting residue was dried under vacuum and carried on as-is as soon as possible.

E. The product prepared in step D (assume 1.0 mmol) was dissolved in 15 mL methylene chloride. 8-[3-N-methylamino-2,6-dichlorobenzyl)oxy]-2-methyl quinoline (0.176 g, 0.507 mmol), prepared as described above, was added to the reaction and the solution was allowed to stir under nitrogen for 16 hours. The reaction was then quenched by addition of ~2 mL of water. The solvents were then removed in vacuo and the residue dissolved in methylene chloride and treated with diisopropylethylamine followed by evaporation of the solvents in vacuo. The residue was purified via silica gel chromatography eluting with 10% MeOH/90% methylene chloride. The proper fractions were isolated and the organics were removed in vacuo to yield the title product (0.344 g) as an orange-yellow powder. MS: M+1=655.

Following the procedures described above and the appropriate reagents, starting materials and purification methods known to those skilled in the art, other compounds of the present invention may be prepared but not limited to:

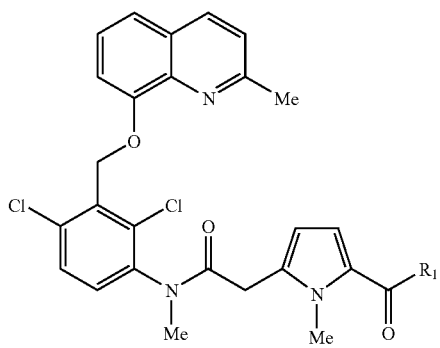

| Compound | $R_1$ | MS: (M + 1) | MW |
|---|---|---|---|
| 24 | —$CH_2N(Me)Ph$ | 615 | 615.55 |
| 25 | (5-Cl)2-Thienyl | 612 | 612.96 |
| 26 | 2-Naphthyl | 622 | 622.54 |
| 27 | —CH=CHPh | 598 | 598.52 |
| 28 | —$CH_2Ph$ | 586 | 586.51 |
| 29 | Ph | 572 | 572.48 |
| 30 | Cyclohexyl | 578 | 578.53 |
| 31 | —$C(CH_3)_3$ | 552 | 552.49 |
| 32 | Cyclopropyl | 536 | 536.45 |
| 33 | 3-Pyridyl | 573 | 573.47 |
| 34 | (4-F)Ph | 590 | 590.47 |
| 35 | (4-Br)Ph | 651 | 651.38 |
| 36 | (2-NHAc)Ph | 629 | 629.54 |
| 37 | —$CH_2$Pyrrolidine | 579 | 579.52 |
| 38 | 1-Naphthyl | 622 | 622.54 |
| 39 | —CH=$C(CH_3)_2$ | 550 | 550.48 |
| 40 | (4-Cl)Ph | 606 | 606.93 |
| 41 | (5-Me)2-Thienyl | 592 | 592.54 |
| 42 | (3-$NO_2$)Ph | 617 | 617.48 |
| 43 | (5-SMe)2-Thienyl | 624 | 624.61 |
| 44 | (3-CN)Ph | 597 | 597.49 |
| 45 | 2-Pyridyl | 573 | 573.47 |
| 47 | (4-$CH_2NMe_2$)Ph | 629 | 629.58 |
| 48 | —$CH_2NEt_2$ | 581 | 581.54 |
| 49 | $CH_2N(Me)$2-Pyridyl | 616 | 616.54 |
| 50 | (3,4-$O_2CH_2$)Ph | 616 | 616.49 |
| 51 | (4-$CF_3$)Ph | 640 | 640.48 |
| 115 | (4-$NMe_2$)Ph | 615 | 615.55 |
| 52 | (5,6-Cl)3-Pyridyl | 642 | 642.36 |
| 53 | (2-$NH_2$)Phg | 587 | 587.50 |
| 54 | (4-Me)Ph | 586 | 586.51 |
| 55 | 3-Thienyl | 578 | 578.51 |
| 57 | (3-$NH_2$)Ph | 587 | 587.50 |
| 58 | —$CH_2$((4-Ph)Piperidine) | 669 | 669.64 |
| 59 | —$CH_2$((4-Bn)Piperidine) | 683 | 683.67 |

-continued

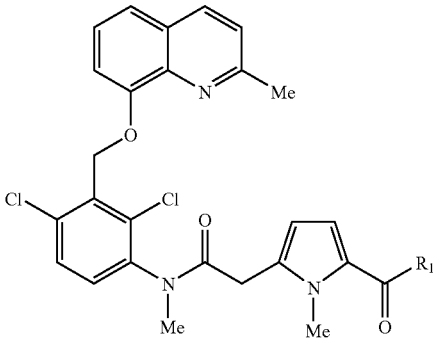

| Compound | $R_1$ | MS: (M + 1) | MW |
|---|---|---|---|
| 61 | 2-Thienyl | 578 | 578.51 |
| 63 | (4-$NO_2$)Ph | 617 | 617.48 |
| 64 | (4-$CO_2Me$)Ph | 630 | 630.52 |
| 66 | (2-$NO_2$)Ph | 617 | 617.4 |
| 68 | (4-OMe)Ph | 602 | 602.51 |
| 69 | (4-SMe)Ph | 618 | 618.58 |
| 70 | (4-$SO_2NH_2$)Ph | 651 | 651.56 |
| 71 | (6-CN)3-Pyridyl | 598 | 598.48 |
| 72 | (3-NHAc)Ph | 629 | 629.54 |
| 76 | (4-CN)Ph | 597 | 597.49 |

Example 12

N-[2,4-Dichloro-3-(2-methyl-quinolin-8-yloxymethyl)-phenyl]-2-[4-(4-methoxy-benzoyl)-1-methyl-1H-pyrrol-2-yl]-N-methyl-acetamide (Compound 2)

A. [5-(4-Methoxy-benzoyl)-1-methyl-1H-pyrrol-2-yl]-acetic acid methyl ester (0.720 g, 2.51 mmol), prepared as described in Example 1 and using 4-methoxy benzoic acid instead of 3-methyl-4-nitro benzoic acid in step A, was dissolved in 10 mL trifluoroacetic acid and was refluxed for two hours. The solvents were then removed in vacuo and the residue dissolved in methylene chloride and treated with diisopropylethylamine followed by evaporation of the solvents in vacuo. The residue was purified via silica gel chromatography eluting with a gradient of 35-50% EtOAc/hexanes. The proper fractions were isolated and the organics were removed in vacuo to yield the rearranged pyrrolyl ester (0.612 g, 2.13 mmol) as a yellow oil.

B. The product prepared in step A (0.604 g, 2.10 mmol) was suspended in 10 mL ethanol and then heated to reflux. When refluxing, 1N NaOH solution (2.10 mL, 2.10 mmol) was added to the reaction over 13 minutes. The reaction was allowed to continue refluxing for an additional hour. After cooling the solvents were removed in vacuo. The residue was then dissolved in 20 mL water and filtered to remove turbidity. The filtrate was acidified with excess 2N HCl. The resulting suspension was centrifuged to separate the supernatant. The solid was then dried under vacuum to yield the corresponding carboxylic acid (0.557 g, 2.04 mmol) as a pale tan powder.

C. The product prepared in step B (0.027 g, 0.099 mmol) was dissolved in 5 mL methylene chloride. One drop of DMF was added and the reaction was cooled on an ice bath under a nitrogen atmosphere. Oxalyl chloride (0.026 mL, 0.30 mmol) was added and the reaction was allowed to stir for 30 minutes. The organics were then evaporated under a stream of nitrogen while still on the ice bath. The resulting residue was carried on as-is as soon as possible.

D. The product prepared in step C (assume 0.099 mmol) was dissolved in 5 mL methylene chloride. 8-[3-N-methylamino-2,6-dichlorobenzyl)oxy]-2-methyl quinoline (0.018 g, 0.052 mmol), prepared as described above, was added to the reaction along with a little DMAP and the. solution was allowed to stir under nitrogen for 16 hours. The reaction was then quenched by addition of ~2 ml of water. The solvents were then removed in vacuo and the residue dissolved in methylene chloride and treated with diisopropylethylamine followed by evaporation of the solvents in vacuo. The residue was purified via reverse phase chromatography eluting with a gradient of acetonitrile:water 10-90%. The proper fractions were isolated and lyophilized to yield the title product (0.011 g, 0.015 mmol) as a peach-colored powder. $^1$H NMR (CDCl$_3$): δ 8.60 (d, 1H), 7.78 (m, 3H), 7.64 (m, 2H), 7.52 (dd, 2H), 7.37 (d, 3.50 (br q, 2H), 3.29 (s, 3H), 2.93 (s, 3H); MS: M+1=602.

Example 13

N-[2,4-Dichloro-3-(2-methyl-quinolin-8-yloxymethyl)-phenyl]-2-[4-(4-methanesulfonyl-benzoyl)-1-methyl-1H-pyrrol-2-yl]-N-methyl-acetamide (Compound 1)

Using the same procedure as Example 12, but using [5-(4-methanesulfonyl-benzoyl)-1-methyl-1H-pyrrol-2-yl]-acetic acid methyl ester, prepared as described in Example 1 and using 4-methansulfonylbenzoic acid instead of 3-methyl-4-nitro benzoic acid in step A, Compound 1 was prepared. MS: M+1=650.

Example 14

2-[5-(4-Cyano-benzoyl)-1-methyl-1H-pyrrol-3-yl]-N-[2,4-dichloro-3-(2-methyl-quinolin-8-yloxymethyl)-phenyl]-N-methyl-acetamide (Compound 4)

A. N-methyl pyrrole (18 mL, 203 mmol) was added to a 3-neck flask. Copper(II) triflate (0.371 g, 1.03 mmol) was added and the mixture was heated to 40° C. Ethyl diazoacetate (7.4 mL, 70.4 mmol) was then carefully added to the reaction dropwise over 25 minutes. The temperature rose to over 90° C. during the addition. After the addition was complete the mixture was maintained at 50° C. for 1 hour. The reaction was then diluted with methylene chloride and the solids filtered off over a pad of celite. The filtrate was concentrated and purified via silica gel chromatography eluting with 15% EtOAc/85% hexanes. The proper fractions were isolated and concentrated to yield the pyrrolyl acetate ester (2.462 g, 14.7 mmol) as a yellow oil.

B. The product prepared in step A (2.467 g, 14.8 mmol) was dissolved in 30 mL toluene in a 3-neck flask. 4-Cyanobenzoyl chloride (3.685 g, 22.3 mmol) was added. The flask was equipped with a reflux condenser and a nitrogen bubbler. Nitrogen was gently bubbled through the reaction as it was heated at reflux for 16 hours. The reaction was then diluted with 20 mL toluene and poured into a solution of 20 mL 3-(diethylamino)propylamine in 200 mL water. This was shaken then extracted with 200 mL chloroform. The organics were washed 3 times with 100 mL 1N HCl. The organics were dried with MgSO$_4$, treated with charcoal then filtered and the solvents removed in vacuo. The residue was purified via reverse phase chromatography eluting with a gradient of acetonitrile:water 10-90%. The proper fractions were collected and concentrated to yield the acylated pyrrolyl acetate ester (0.746 g, 2.52 mmol) as a yellow oil.

C. The product prepared in step B (0.738 g, 2.49 mmol) was dissolved in 30 mL 5:1 THF:water. Lithium hydroxide monohydrate (0.107 g, 2.55 mmol) was then added to the reaction and was stirred for 16 hours. The solvents were then removed in vacuo and the residue dissolved in 50 mL water. The solution was filtered to remove turbidity then acidified with excess 1N HCl. The resulting solid was filtered off and rinsed with water and then dried under vacuum at 50° C. to yield the corresponding carboxylic acid (1.079 g, 4.55 mmol) as a cream-colored powder.

D. The product prepared in step C (0.162 g, 0.60 mmol) was dissolved in 10 mL methylene chloride. One drop of DMF was added and the reaction was cooled on an ice bath under a nitrogen atmosphere. Oxalyl chloride (0.16 mL, 1.83 mmol) was added and the reaction was allowed to stir for 1.5 hours. The organics were then evaporated under a stream of nitrogen while still on the ice bath. The resulting residue was dried under vacuum and carried on as-is as soon as possible.

E. The product prepared in step D (assume 0.60 mmol) was dissolved in 10 mL methylene chloride. 8-[3-N-methylamino-2,6-dichlorobenzyl)oxy]-2-methyl quinoline (0.111 g, 0.320 mmol), prepared as described above, was added to the reaction and the solution was allowed to stir under nitrogen for 18 hours. The reaction was then quenched by addition of ~2 mL of water. The solvents were then removed in vacuo and the residue dissolved in methylene chloride/methanol and treated with diisopropylethylamine followed by evaporation of the solvents in vacuo. The residue was purified via silica gel chromatography eluting with 75% EtOAc/25% hexanes. The proper fractions were isolated and the organics were removed in vacuo to yield the title product (0.126 g, 0.211 mmol) as a yellow-orange powder. $^1$H NMR (CDCl$_3$): δ 8.01 (s, 1H), 7.79 (d, 2H), 7.68 (d, 2H), 7.48-7.11 (m, 6H), 6.86 (d, H), 6.46 (d, 1H), 5.65 (s, 2H), 3.93 (s, 3H), 3.21 (s app, 5H), 2.68 (s, 3H); MS: M+1=597.

Example 15

2-[5-(4-Cyano-benzoyl)-1-ethyl-1H-pyrrol-3-yl]-N-[2,4-dichloro-3-(2-methyl-quinolin-8-yloxymethyl)-phenyl]-N-methyl-acetamide (Compound 3)

Using the same procedure as described in Example 14, except N-ethyl pyrrole was used instead of N-methyl pyrrole, Compound 3 was prepared. MS: M+1=611

Example 16

2-[5-(4-Cyano-benzoyl)-1H-pyrrol-2-yl]-N-[2,4-dichloro-3-(2-methyl-quinolin-8-yloxymethyl)-phenyl]-N-methyl-acetamide (Compound 6)

t-Butyl-2-pyrroleacetate and the Vilsmeier-Haack reagent were prepared according to literature procedure: *J. Org. Chem.* 1994, 59, 5230-34.

A. The 4-cyanophenyl Vilsmeier-Haack reagent (1.683 g, 7.35 mmol) was dissolved in 10 mL methylene chloride. The t-butyl-2-pyrroleacetate (1.182 g, 6.52 mmol) was dissolved separately in 5 mL methylene chloride. The pyrrole solution was pipefted into the Vilsmeier-Haack reagent solution and the reaction was stirred for 1 hour. A solution of 2.5 g sodium acetate trihydrate in 10 mL water was then added to the reaction and the biphasic mixture was vigorously stirred for 16 hours. The reaction was then diluted with 25 mL water and extracted with 50 mL methylene chloride. The organics were dried with MgSO$_4$ and concentrated. The residue was purified via silica gel chromatography eluting with 20% EtOAc/80% hexanes. The proper fractions were isolated and concentrated, triturated with hexanes, filtered and dried under vacuum to yield the acylated pyrrolyl acetate (1.345 g, 4.33 mmol) as a tan powder.

B. The product prepared in step A (0.466 g, 1.50 mmol) was dissolved in 25 mL methylene chloride and treated with 5 mL trifluoroacetic acid. The reaction stirred for 4.5 hours and then concentrated, triturated with a little ether, and filtered to yield the corresponding carboxylic acid (0.361 g, 1.42 mmol) as a grey-tan powder.

C. The product prepared in step B (0.027 g, 0.106 mmol) was suspended in 5 mL methylene chloride. One drop of DMF was added and the reaction was cooled on an ice bath under a nitrogen atmosphere. Oxalyl chloride (0.030 mL, 0.34 mmol) was added and the reaction was allowed to stir for 1 hour. The organics were then evaporated under a stream of nitrogen while still on the ice bath. The resulting residue was carried on as-is as soon as possible.

D. The product prepared in step C (assume 0.106 mmol) was dissolved in 5 mL methylene chloride. 8-[3-N-methylamino-2,6-dichlorobenzyl)oxy]-2-methyl quinoline (0.031 g, 0.089 mmol), prepared as described above, was added to the reaction along with a small quantity of DMAP and the solution was allowed to stir under nitrogen for 19 hours. The reaction was then quenched by addition of ~2 mL of isopropanol. The solvents were then removed in vacuo and the residue was purified via reverse phase chromatography eluting with a gradient of acetonitrile: water 10-90%. The proper fractions were isolated and lyophilized to yield the title product (0.007 g, 0.010 mmol) as a light yellow powder. $^1$H NMR (CDCl$_3$): δ 8.62 (d, 1H), 7.85-7.58 (m, 6H), 7.52 (d, 2H), 7.38-7.16 (m, 2H), 6.65 (t, 1H) 6.29 (t, 1H), 5.60 (d, 2H), 3.74 (br q, 2H), 3.27 (s, 3H), 3.02 (s, 3H); MS: M+1=583.

Following the procedure described above for Example 16 and the appropriate reagents, starting materials and purification methods known to those skilled in the art, other compounds of the present invention may be prepared but not limited to:

| Cmpd | Y | R$_5$ | R$_6$ | R$_{12}$ | R$_1$ | MS: (M + 1) |
|---|---|---|---|---|---|---|
| 5 | Cl | Me | H | H | (4-OMe)Ph | 588 |
| 120 | Cl | H | Me | Me | (4-OMe)Ph | 602 |

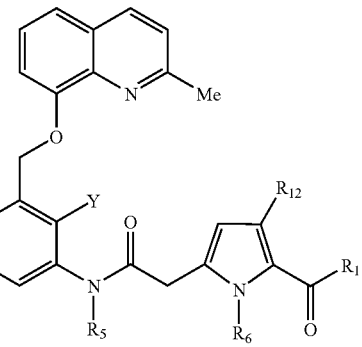

| Cmpd | Y | R$_5$ | R$_6$ | R$_{12}$ | R$_1$ | MS: (M + 1) |
|---|---|---|---|---|---|---|
| 119 | Cl | H | Me | H | (4-OMe)Ph | 588 |
| 121 | Cl | H | Me | Me | (4-NNH$_2$)Ph | 587 |

Example 17

N-[2,4-Dichloro-3-(2-methyl-quinolin-8-yloxymethyl)-phenyl]-N-methyl-2-{1-methyl-5-[2-(4-phenyl-piperidin-1-yl)-acetyl]-1H-pyrrol-2-yl}-acetamide (Compound 58)

A. Chloroacetyl chloride (4.2 mL, 52.7 mmol) and methyl-N-methyl-2-pyrroleacetate (5.0 mL, 34.7 mmol) were combined in 35 mL toluene in a 3-neck flask. The flask was equipped with a reflux condenser and a nitrogen bubbler. Nitrogen was gently bubbled through the reaction as it was heated at 100° C. for 15.5 hours. The reaction was then concentrated and the residue purified via silica gel chromatography eluting with 30% EtOAc/70% hexanes. The proper fractions were isolated and concentrated to yield the acylated pyrrolyl acetate (5.629 g, 24.5 mmol) as an orange oil that solidified after standing.

B. The product prepared in step A (1.150 g, 5.01 mmol) was dissolved in 25 mL acetonitrile. Triethylamine (0.70 mL, 5.02 mmol) and 4-phenyl piperidine (0.822 g, 5.10 mmol) was added along with a small quantity of KI. The reaction was refluxed for 19 hours then concentrated. The residue was taken up in 75 mL methylene chloride, washed three times with saturated NaHCO$_3$, and dried with Na$_2$SO$_4$. Concentration of the organics and drying under vacuum at 50° C. yielded the corresponding 4-phenyl piperidinyl intermediate (1.727 g, 4.87 mmol) as a dark oil.

C. The product prepared in step B (assume 4.87 mmol) was dissolved in 10 mL concentrated HCl. The reaction mixture was stirred for 17 hours then concentrated. The residue was dissolved in acetone and again concentrated. The residue was triturated with THF containing a little acetone. The solid was filtered off, rinsed with ether and dried at 50° C. under vacuum to yield the corresponding carboxylic acid (1.540 g, 4.09 mmol) as a light brown powder.

D. The product prepared in step C (0.377 g, 1.00 mmol) was dissolved in 15 mL methylene chloride. One drop of DMF was added and the reaction was cooled on an ice bath under a nitrogen atmosphere. Oxalyl chloride (0.26 mL, 3.0 mmol) was added and the reaction was allowed to stir for 2.5 hours. The organics were then evaporated under a stream of nitrogen while still on the ice bath. The resulting residue was dried under vacuum and carried on as-is as soon as possible.

E. The product prepared in step D (assume 1.00 mmol) was dissolved in 15 mL methylene chloride. 8-[3-N-methylamino-2,6-dichlorobenzyl)oxy]-2-methyl quinoline (0.180 g, 0.518 mmol), prepared as described above, was added to the reaction and the solution was allowed to stir under nitrogen for 15 hours. The reaction was then quenched by addition of ~2 mL of water. The solvents were then removed in vacuo and the residue dissolved in methylene chloride/methanol and treated with diisopropylethylamine followed by concentration. The residue was purified via silica gel chromatography eluting with 3% ammonical MeOH/97% methylene chloride. The proper fractions were isolated and the organics were removed in vacuo to yield the product (0.308 g, 0.460 mmol) as a yellow powder. $^1$H NMR (CDCl$_3$): δ 7.99 (d, 1H), 7.48-7.13 (m, 11H), 7.01 (d, 1H), 5.81 (d, 1H), 5.66 (s, 2H), 3.77 (s, 3H), 3.61 (s, 2H), 3.35 (d, 2H), 3.21 (s, 3H), 3.08 (br t, 2H), 2.71 (s, 3H), 2.48 (m, 1H), 2.21 (br t, 2H), 1.92 (dq, 2H), 1.82 (br t, 2H); MS: M+1=669.

Following the procedure of Example 17 and using the appropriate reagents, starting materials and purification methods known to those skilled in the art, other compounds of the present invention may be prepared but not limited to:

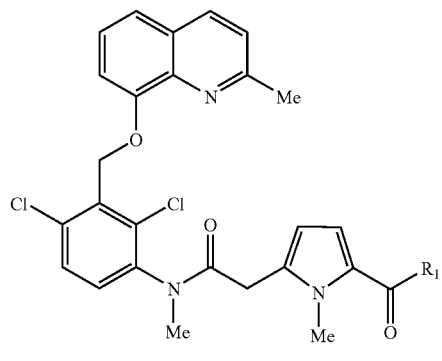

| Compound | RWJ | R$_1$ | MS: (M + 1) |
|---|---|---|---|
| 59 | 397413 | —CH$_2$(4-Bn)piperidine | 683 |
| 48 | 353520 | —CH$_2$NEt$_2$ | 581 |
| 49 | 411568 | —CH$_2$N(Me)(2-pyridyl) | 616 |
| 37 | 353521 | —CH$_2$-1-pyrrolidine | 579 |
| 23 | 391024 | —(CH$_2$)$_4$CH$_3$ | 566 |

Example 18

2-[5-(4-Cyano-benzoyl)-1-cyclopropylmethyl-1H-pyrrol-2-yl]-N-[2,4-dichloro-3-(2-methyl-quinolin-8-yloxymethyl)-phenyl]-N-methyl-acetamide (Compound 11)

A. 2,5-Dimethoxytetrahydrofuran (65 mL, 502 mmol) was dissolved in 100 mL acetic acid in a 3-neck flask. (Aminomethyl)cyclopropane (42 mL, 484 mmol) was added dropwise to the reaction over a 10 minute period. The temperature rose to over 75° C. during the addition. After the addition was complete the solution was refluxed for 5 hours. The reaction was then diluted with 750 mL brine and extracted with 375 mL ether. The organics were washed once with 375 mL brine, twice with 375 mL saturated NaHCO$_3$, then once more with 375 mL brine. The organics were dried with Na$_2$SO$_4$, filtered, and concentrated carefully in vacuo. The residue was subjected to vacuum distillation. The product distilled at 128-130° C. under 150-155 mmHg. The cyclopropyl methyl pyrrole was isolated as a colorless liquid (23.01 g, 190 mmol). $^1$H NMR (CDCl$_3$ δ 6.74 (t, 2H), 6.17 (t, 2H), 3.74 (d, 2H), 1.19 (m, 1H), 0.63 (m, 2H), 0.32 (m, 2H).

B. The product prepared in step A (22.58 g, 186.3 mmol) was added to a 3-neck flask. Copper bronze (0.398 g, 6.26 mmol) was added and the mixture was heated to 100° C. Ethyl diazoacetate (7.0 mL, 66.6 mmol) was then carefully added to the reaction dropwise over 20 minutes. The temperature rose during the addition. After the addition is complete the mixture was maintained at 100° C. for 1 hour. The reaction was then diluted with methylene chloride and the solids filtered off over a pad of celite. The filtrate was concentrated and purified via silica gel chromatography eluting with 7.5% EtOAc/92.5% hexanes. The proper fractions were isolated and concentrated to yield the cyclopropyl pyrrolyl acetate (2.207 g, 10.6 mmol) as a light yellow liquid. $^1$H NMR (CDCl$_3$): δ 6.78 (m, 1H), 6.12 (m, 1H), 6.05 (m, 1H), 4.15 (q, 2H), 3.73 (d, 2H), 3.65 (s, 2H), 1.28 (t, 3H), 1.17 (m, 1H), 0.62 (m, 2H), 0.32 (m, 2H); MS: M+1=208.

C. The product prepared in step B (2.20 g, 10.63 mmol) was dissolved in 40 mL toluene in a 3-neck flask. 4-Cyanobenzoyl chloride (2.64 g, 15.99 mmol) was added. The flask was equipped with a reflux condenser and a nitrogen bubbler. Nitrogen was gently bubbled through the reaction as it was heated at 100° C. for 42 hours. The reaction was then diluted with 20 mL toluene and poured into a solution of 20 mL 3-(diethylamino)propylamine in 200 mL water. This was shaken then extracted with 200 mL chloroform. The organics were washed 3 times with 100 mL 1N HCl. The organics were dried with MgSO$_4$, treated with charcoal then filtered and the solvents removed in vacuo. The residue was triturated with 10 mL hexanes, filtered, rinsed twice with 5 mL hexanes, and air dried to give the acylated pyrrolyl acetate (2.724 g, 8.10 mmol) as a pink-tan powder. $^1$H NMR (CDCl$_3$): δ 7.85 (d, 2H), 7.76 (d, 2H), 6.64 (d, 1H), 6.18 (d, 1H), 4.43 (d, 2H), 4.22 (q, 2H), 3.74 (s, 2H), 1.30 (t, 3H), 1.22 (m, 1H), 0.53 (m, 2H), 0.39 (m, 2H); MS: M+1=337.

D. The product prepared in step C (1.685 g, 5.01 mmol) was dissolved in 30 mL 5:1 THF:water. Lithium hydroxide monohydrate (0.216 g, 5.15 mmol) was then added to the reaction and was stirred for 7.5 hours. The solvents were then removed in vacuo and the residue dissolved in 50 mL water. The turbid solution was filtered over a pad of celite and the filtrate was then acidified with excess 1N HCl. The resulting solid was filtered off and rinsed with water and then dried under vacuum at 50° C. to yield the corresponding carboxylic acid (1.331 g, 4.32 mmol) as a tan powder. $^1$H NMR (d$_6$-DMSO): δ 12.68 (s, 1H), 7.98 (d, 2H), 7.83 (d, 2H), 6.62 (d, 1H), 6.19 (d, 1H), 4.33 (d, 2H), 3.82 (s, 2H), 1.20 (m, 1H), 0.44 (m, 2H), 0.34 (m, 2H); MS: M-CO$_2$-1=263.

E. The product prepared in step D (0.309 g, 1.00 mmol) was dissolved in 15 mL methylene chloride. One drop of DMF was added and the reaction was cooled on an ice bath under an argon atmosphere. Oxalyl chloride (0.26 mL, 3.0 mmol) was added and the reaction was allowed to stir for 2 hours. The organics were then evaporated under a stream of argon while still on the ice bath. The resulting residue was dried under vacuum and carried on as-is as soon as possible.

F. The product prepared in step E (assume 1.00 mmol) was dissolved in 15 mL methylene chloride. 8-[3-N-methylamino-2,6-dichlorobenzyl)oxy]-2-methyl quinoline (0.175 g, 0.504 mmol), prepared as described above, and a small quantity of DMAP was added to the reaction and the solution was allowed to stir under nitrogen for 20 hours. The reaction was then quenched by addition of ~2 mL of water. The solvents were then removed in vacuo and the residue dissolved in methylene chloride and treated with diisopropylethylamine followed by evaporation of the solvents in vacuo. The residue was purified via silica gel chromatography eluting with 50% EtOAc/50% hexanes. The proper fractions were isolated and the organics were removed in vacuo to yield the product (0.244 g, 0.383 mmol) as a yellow-orange powder. $^1$H NMR (CDCl$_3$): δ 8.03 (d, 1H), 7.78 (d, 2H), 7.60 (d, 2H), 7.51-7.36 (m, 3H), 7.35-7.17 (m, 3H), 6.68 (d, 1H), 5.86 (d, 1H), 5.68 (s, 2H), 4.32 (m, 2H), 3.52 (s, 2H), 3.24 (s, 3H), 2.68 (s, 3H), 1.10 (m, 1H), 0.44 (m, 2H), 0.29 (m, 2H); MS: M+1=637.

Following the procedure described above for Example 18 and the appropriate reagents, starting materials and purification methods known to those skilled in the art, other compounds of the present invention may be prepared but not limited to:

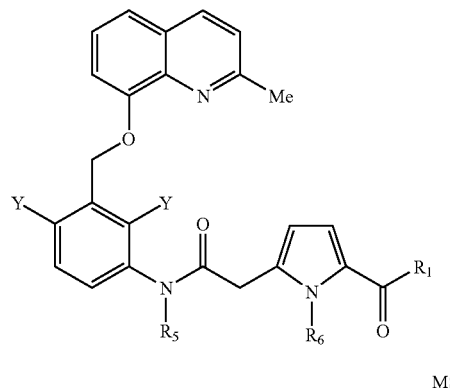

| Cmpd | Y  | R$_5$ | R$_6$ | R$_1$    | MS: (M + 1) |
|------|----|-------|-------|----------|-------------|
| 8    | Cl | Me    | Et    | (4-CN)Ph | 611         |
| 7    | Me | Me    | Et    | (4-CN)Ph | 571         |
| 9    | Cl | Me    | nPr   | (4-CN)Ph | 625         |
| 10   | Cl | Me    | nBu   | (4-CN)Ph | 639         |
| 12   | Cl | Me    | iBu   | (4-CN)Ph | 639         |
| 13   | Cl | Me    | iAm   | (4-CN)Ph | 653         |

Example 19

2-[5-(4-Cyano-benzoyl)-1-methyl-1H-pyrrol-2-yl]-N-[2,4-dimethyl-3-(2-methyl-quinolin-8-yloxymethyl)-phenyl]-N-methyl-acetamide (Compound 79)

A. 4-Cyanobenzoyl chloride (14.61 g, 88.2 mmol) was suspended in 75 mL in a 3-neck flask. Methyl-N-methyl-2-pyrroleacetate (11.0 mL, 76.4 mmol) was added to the reaction. The flask was equipped with a reflux condenser and a nitrogen bubbler. Nitrogen was gently bubbled through the reaction as it was heated at 105° C. for 22.5 hours. The reaction was then diluted with 50 mL toluene and poured into a solution of 50 mL 3-(diethylamino) propylamine in 500 mL water. This was shaken then extracted once with 300 mL chloroform and once with 200 mL chloroform. The combined organics were washed 4 times with 200 mL 1N HCl then once with 200 mL brine. The organics were dried with MgSO$_4$, treated with charcoal then filtered and the solvents removed in vacuo. The residue was triturated with 100 mL methanol, filtered, and rinsed twice with 25 mL methanol. The solid was dried under vacuum to yield the pyrrolyl acetate (13.58 g, 48.1 mmol) as a tan powder.

B. The product prepared in step A (13.58 g, 48.1 mmol) was suspended in 300 mL 5:1 THF:water. Lithium hydroxide monohydrate (2.037 g, 48.5 mmol) was then added to the reaction and was stirred for 1 hour. The reaction was then concentrated in vacuo until the organics were removed. Water was added to the residue to bring the volume to 1 L and the solution was filtered over a pad of celite. The filtrate was treated with excess 2N HCl. The resulting solid was filtered off, rinsed twice with water, and dried under vacuum at 50° C. to yield the corresponding carboxylic acid (11.778 g, 43.9 mmol) as a tan powder.

C. The product prepared in step B (4.839 g, 18.04 mmol) was dissolved in 150 mL methylene chloride. Five drops of DMF was added and the reaction was cooled on an ice bath under a nitrogen atmosphere. Oxalyl chloride (4.7 mL, 53.9 mmol) was added and the reaction was allowed to stir for 4 hours. The organics were then evaporated under a stream of nitrogen while still on the ice bath. The resulting residue was dried under vacuum and carried on as-is as soon as possible.

D. The product prepared in step C (assume 18.04 mmol) was dissolved in 150 mL methylene chloride. 8-[(3-N-methylamino-2,6-dimethylbenzyl)oxy]-2-methyl quinoline (2.826 g, 9.22 mmol), prepared as described above, was added to the reaction and the solution was allowed to stir under nitrogen for 15 hours. The reaction was then quenched by addition of ~2 mL of water. The solvents were then removed in vacuo and the residue dissolved in methylene chloride/methanol and treated with diisopropylethylamine followed by concentration. The residue was purified via silica gel chromatography eluting with 65% EtOAc/35% hexanes. The proper fractions were isolated and concentrated and the material was dissolved in methylene chloride and treated with excess ethereal HCl. The solution was concentrated and dried under vacuum at 50° C. to yield the title product (4.00 g, 6.45 mmol) as a yellow-tan powder. Elemental analysis calculated for C$_{35}$H$_{32}$N$_4$O$_3$.1.35HCl.0.8H$_2$O: C, 67.78; H, 5.68; N, 9.04; KF, 2.33. Found: C, 67.79; H, 5.60; N, 8.87; KF, 2.31; $^1$H NMR (CDCl$_3$): δ 8.61 (d, 1H), 7.81 (m, 2H), 7.72 (t app, 3H), 7.63 (dd, 2H), 7.48 (d, 1H), 7.21 (d, 1H), 7.13 (d, 1H), 6.55 (d, 1H), 6.03 (d, 1H), 5.50 (s, 2H), 3.92 (s, 3H), 3.72 (m, 2H), 3.42 (s, 3H), 3.27 (s, 3H), 2.50 (d, 6H); MS: M+1=557.

Example 20

2-[5-(4-Chloro-pyridine-3-carbonyl)-1-methyl-1H-pyrrol-2-yl]-N-[2,4-dimethyl-3-(2-methyl-quinolin-8-yloxymethyl)-phenyl]-N-methyl-acetamide (Compound 77)

A. 6-Chloronicotinoyl chloride (21.14 g, 120.1 mmol) was suspended in 100 mL toluene in a 3-neck flask. Methyl-N-methyl-2-pyrroleacetate (15.0 mL, 104.2 mmol) was added to the reaction. The flask was equipped with a reflux condenser and a nitrogen bubbler. Nitrogen was gently bubbled through the reaction as it was heated at 105° C. for 19 hours. The reaction was then diluted with 400 mL chloroform and washed once with 400 mL 10% $Na_2CO_3$ solution and twice with 200 mL 10% $Na_2CO_3$ solution. The organics were dried with $MgSO_4$ and treated with charcoal then filtered and concentrated. The residue was triturated with 50 mL methanol, filtered, and rinsed twice more with 25 mL methanol. The solid was then dried under vacuum to yield the pyrrolyl acetate (20.88 g, 71.3 mmol) as a tan powder.

B. The product prepared in step A (20.88 g, 71.3 mmol) was suspended in 300 mL 5:1 THF:water. Lithium hydroxide monohydrate (3.148 g, 75.0 mmol) was then added to the reaction and was stirred for 48 hours. The reaction was then concentrated in vacuo until the organics have been removed. Water was added to the residue to bring the volume to 400 mL followed by 1N HCl (75.0 mL, 75.0 mmol). The resulting solid was filtered off and dried under vacuum at 50° C. to yield the corresponding carboxylic acid (19.325 g, 69.3 mmol) as a light tan powder.

C. The product prepared in step B (4.188 g, 15.03 mmol) was dissolved in 150 mL methylene chloride. Five drops of DMF was added and the reaction was cooled on an ice bath under a nitrogen atmosphere. Oxalyl chloride (3.9 mL, 44.7 mmol) was added and the reaction was allowed to stir for 1 hour. The organics were then evaporated under a stream of nitrogen while still on the ice bath. The resulting residue was dried under vacuum and carried on as-is as soon as possible.

D. The product prepared in step C (assume 15.03 mmol) was dissolved in 150 mL methylene chloride. 8-[(3-N-methylamino-2,6-dimethylbenzyl)oxy]-2-methyl quinoline (2.311 g, 7.54 mmol), prepared as described above, and 100 mgs of DMAP was added to the reaction and the solution was allowed to stir under nitrogen for 48 hours. The reaction was then quenched by addition of a ~2 mL of water. The solvents were then removed in vacuo and the residue dissolved in methylene chloride/methanol and treated with diisopropylethylamine followed by concentration. The residue was purified via silica gel chromatography eluting with 65% EtOAc/35% hexanes. The proper fractions were isolated and concentrated and the material was dissolved in methylene chloride and treated with excess ethereal HCl. The solution was concentrated and dried under vacuum at 50° C. to yield the title product (2.30 g, 3.68 mmol) as a yellow powder. Elemental analysis calculated for $C_{33}H_{31}ClN_4O_3 \cdot 1.25HCl \cdot 0.65H_2O$: C, 63.49; H, 5.42; N, 8.98; Cl, 12.78; KF, 1.88. Found: C, 63.57; H, 5.19; N, 8.82; Cl, 12.83; KF, 1.88; $^1$H NMR ($CDCl_3$): δ 8.72 (s, 1H), 8.53 (br s, 1H), 8.00 (d, 1H), 7.72 (br t, 1H), 7.58 (d, 2H), 7.44 (d, 1H), 7.37 (m, 1H), 7.18 (d, 1H), 7.10 (d, 1H), 6.59 (d, 1H), 6.02 (d, 1H), 5.46 (q, 2H), 3.90 (s, 3H), 3.69 (m, 2H), 3.36 (br s, 3H), 3.27 (s, 3H), 2.51 (s, 3H), 2.44 (s, 3H); MS: M+1=567.

Example 21

2-[5-(4-Cyano-pyridine-3-carbonyl)-1-methyl-1H-pyrrol-2-yl]-N-[2,4-dimethyl-3-(2-methyl-quinolin-8-yloxymethyl)-phenyl]-N-methyl-acetamide (Compound 78)

A. 6-Cyanonicotinic acid (9.547 g, 64.45 mmol) was suspended in thionyl chloride (40 mL, 548 mmol). The flask was equipped with a reflux condenser and a drying tube. The reaction mixture was heated at reflux for 17 hours. The excess thionyl chloride was removed in vacuo. The residue was taken up in toluene and concentrated to yield the corresponding acid chloride (10.879 g) as an orange-brown solid.

B. The product prepared in step A (10.87 g, 65.3 mmol) was susp ended in 60 mL toluene in a 3-neck flask. Methyl-N-methyl-2-pyrroleacetate (8.0 mL, 55.6 mmol) was added to the reaction. The flask was equipped with a reflux condenser and an argon bubbler. Argon was gently bubbled through the reaction as it was heated at 105° C. for 16 hours. The reaction was then diluted with 400 mL chloroform and washed four times with 200 mL 10% $Na_2CO_3$ solution. The organics were dried with $MgSO_4$ and treated with charcoal then filtered and concentrated. The residue was triturated with 70 mL methanol, filtered, and rinsed twice more with 25 mL methanol. The solid was then dried under vacuum to yield the acylated pyrrolyl acetate (12.126 g, 42.8 mmol) as a tan-brown powder.

C. The product prepared in step B (12.124 g, 42.8 mmol) was suspended in 300 mL 5:1 THF:water. Lithium hydroxide monohydrate (1.804 g, 43.0 mmol) was then added to the reaction and was stirred for 14.5 hours. The reaction was then concentrated in vacuo until the organics have been removed. Water (200 mL) was added to the residue followed by 1N HCl (43.0 mL, 43.0 mmol). The resulting solid was filtered off, rinsed twice with water, and dried under vacuum at 50° C. to yield the corresponding acid chloride (11.300 g, 42.0 mmol) as a light tan powder.

D. The product prepared in step C (4.044 g, 15.02 mmol) was dissolved in 150 mL methylene chloride. Five drops of DMF was added and the reaction was cooled on an ice bath under a nitrogen atmosphere. Oxalyl chloride (3.9 mL, 44.7 mmol) was added and the reaction was allowed to stir for 5 hours. The organics were then evaporated under a stream of nitrogen while still on the ice bath. The resulting residue was dried under vacuum and carried on as-is as soon as possible.

E. The product prepared in step D (assume 15.02 mmol) was dissolved in 150 mL methylene chloride. 8-[(3-N-methylamino-2,6-dimethylbenzyl)oxy]-2-methyl quinoline (2.307 g, 7.53 mmol), prepared as described above, was added to the reaction and the solution was allowed to stir under nitrogen for 14 hours. The reaction was then quenched by addition of ~2 mL of water. The solvents were then removed in vacuo, the residue dissolved in methylene chloride/methanol, treated with diisopropylethylamine followed by concentration. The residue was purified via silica gel chromatography eluting with 70% EtOAc/30% hexanes. The proper fractions were isolated and concentrated and the material was dissolved in methylene chloride and treated with excess ethereal HCl. The solution was concentrated and dried under vacuum at 50° C. to yield the title product (1.75 g, 2.86 mmol) as a yellow-orange powder. Elemental analysis calculated for $C_{34}H_{31}N_5O_3 \cdot 1.2HCl \cdot 0.6H_2O$: C, 66.71; H, 5.50; N, 11.44; Cl, 6.95; KF, 1.77. Found: C, 66.65; H, 5.43; N, 11.33; Cl, 6.78; KF, 1.68; $^1$H NMR ($CDCl_3$): δ 8.97 (s, 1H), 8.53 (br s, 1H), 8.12 (d, 1H), 7.74 (d, 1H), 7.71 (br t, 1H), 7.59 (d, 2H), 7.47 (d, 1H), 7.20 (d, 1H), 7.12 (d, 1H), 6.55 (d, 1H), 6.04 (s, 1H), 5.45 (s, 2H), 3.97 (s, 3H), 3.74 (m, 2H), 3.32 (br s, 3H), 3.23 (s, 3H), 2.49 (d, 6H); MS: M+1=558.

Example 22

3-[5-(4-Chloro-pyridine-3-carbonyl)-1-methyl-1H-pyrrol-2-yl]-N-[2,4-dichloro-3-(2-methyl-quinolin-8-yloxymethyl)-phenyl]-N-methyl-propionamide (Compound 89)

A. N-Methyl-2-pyrrolecarboxaldehyde (50.27 g, 460.6 mmol) was dissolved in 700 mL benzene. Ethyl(triphenylphosphoranylidene)acetate (160.49 g, 460.7 mmol) was added to the reaction. The mixture was heated at reflux under nitrogen for 17.5 hours. The solvents were then removed in vacuo and the residue taken up in 500 mL diethyl ether. The precipitated triphenylphosphine oxide was filtered off and the ether extracts were evaporated in vacuo. The resulting residue was subjected to vacuum distillation. The product distilled at 117-122° C. under 0.46-0.47 mmHg. The alkenyl pyrrolyl ester was isolated as a light yellow oil (65.18 g, 364 mmol).

B. The product prepared in step A (17.93 g, 100.0 mmol) was dissolved in 100 mL ethanol in a hydrogenation bottle. 10% Palladium on carbon (0.899 g) was added and the mixture was hydrogenated at 40-50 psi for 17.5 hours. The catalyst was then filtered off over a pad of celite and the organics were concentrated in vacuo to yield ethyl-N-methyl-2-pyrrolepropionate (18.10 g, 99.9 mmol) as a colorless oil.

C. 6-Chloronicotinoyl chloride (9.25 g, 52.6 mmol) was suspended in 40 mL toluene in a 3-neck flask. Ethyl-N-methyl-2-pyrrolepropionate (6.342 g, 35.0 mmol) was added to the reaction. The flask was equipped with a reflux condenser and a nitrogen bubbler. Nitrogen was gently bubbled through the reaction as it was heated at 105° C. for 18 hours. The reaction was then diluted with 20 mL toluene and poured into a solution of 20 mL 3-(diethylamino)propylamine in 200 mL water. This was shaken then extracted once with 200 mL chloroform. The organics were washed 3 times with 100 mL 1N HCl then once with 100 mL saturated NaHCO₃. The organics were dried with MgSO₄, treated with charcoal then filtered and the solvents removed in vacuo. The residue was triturated with 10 mL methanol, filtered, and rinsed twice more with 10 mL methanol. The solid was dried under vacuum to yield the acylated pyrrolyl propionate (9.199 g, 28.7 mmol) as a greenish-grey powder.

D. The product prepared in step C (1.603 g, 5.00 mmol) was suspended in 30 mL 5:1 THF:water. Lithium hydroxide monohydrate (0.210 g, 5.00 mmol) was then added to the reaction and was stirred for 17.5 hours. The reaction was then concentrated in vacuo until the organics have been removed. Water (50 mL) was added to the residue and the solution was filtered over a nylon disk. The filtrate was treated with 1N HCl (5.0 mL, 5.0 mmol). The resulting solid was filtered off, rinsed twice with water, and dried under vacuum at 50° C. to yield the corresponding acid chloride (1.363 g, 4.66 mmol) as a light tan powder.

E. The product prepared in step D (0.758 g, 2.59 mmol) was dissolved in 40 mL methylene chloride. Two drops of DMF were added and the reaction was cooled on an ice bath under a nitrogen atmosphere. Oxalyl chloride (0.68 mL, 7.79 mmol) was added and the reaction was allowed to stir for 1.5 hours. The organics were then evaporated under a stream of nitrogen while still on the ice bath. The resulting residue was dried under vacuum and carried on as-is as soon as possible.

F. The product prepared in step E (assume 2.59 mmol) was dissolved in 40 mL methylene chloride. The 8-[(3-N-methylamino-2,6-chlorobenzyl)oxy]-2-methyl quinoline (0.692 g, 1.99 mmol), prepared as described above, was added to the reaction in two portions and the solution was allowed to stir under nitrogen for 16.5 hours. The reaction was then quenched by addition of ~2 mL of water. The solvents were then removed in vacuo and the residue dissolved in methylene chloride/methanol and treated with diisopropylethylamine followed by concentration. The residue was purified via silica gel chromatography eluting with 80% EtOAc/20% hexanes. The proper fractions were isolated and concentrated to yield the free base. The free base was dissolved in methylene chloride and treated with excess ethereal HCl. The solution was concentrated and dried under vacuum at 50° C. to yield the title product (0.971 g, 1.48 mmol) as a tan powder. ¹H NMR (CDCl₃): δ 8.74 (d, 1H), 8.02 (m, 2H), 7.48-7.12 (m, 7H), 6.60 (d, 1H), 5.91 (d, 1H), 5.68 (s, 2H), 3.88 (s, 3H), 3.22 (s, 3H), 2.98 (m, 2H), 2.73 (s, 3H), 2.33 (dt, 2H); Free Base: MS: M+1=621; Salt: Elemental analysis calculated for C₃₂H₂₇Cl₃N₄O₃.0.75HCl.0.5H₂O: C, 58.39; H, 4.41; N, 8.52; Cl, 20.20; KF, 1.37. Found: C, 58.45; H, 4.32; N, 8.42; Cl, 20.40; KF, 1.35.

Following the procedure described above for Example 22 and the appropriate reagents, starting materials and purification methods known to those skilled in the art, other compounds of the present invention may be prepared but not limited to:

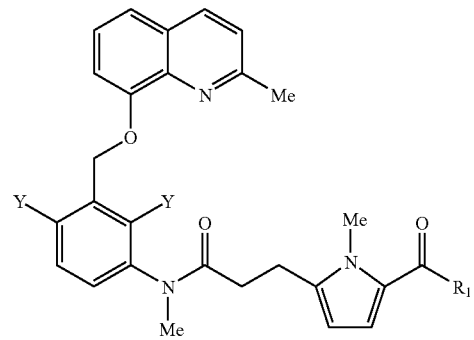

| Compound | Y  | R₁              | MS (M + 1) |
|----------|----|-----------------|------------|
| 80       | Me | 2-Thienyl       | 552        |
| 81       | Cl | 2-Thienyl       | 593        |
| 82       | Me | 4-Pyridyl       | 547        |
| 83       | Cl | 4-Pyridyl       | 588        |
| 84       | Me | 3-Pyridyl       | 547        |
| 85       | Cl | 3-Pyridyl       | 588        |
| 86       | Me | (6-OEt)-3-Pyridyl | 591      |
| 87       | Cl | (6-OEt)-3-Pyridyl | 632      |
| 88       | Me | (6-Cl)-3-Pyridyl  | 582      |
| 90       | Me | (4-CN) Ph       | 571        |
| 91       | Cl | (4-CN) Ph       | 612        |

Example 23

N-[2-Chloro-3-(2-methyl-quinolin-8-yloxymethyl)-phenyl]-2-[5-(3-cyano-benzoyl)-1-methyl-1H-pyrrol-2-yl]-N-methyl-acetamide (Compound 116)

Compound 44 (0.149 g, 0.249 mmol), prepared in the manner of compound 1, except that 3-cyanobenzoic acid was used instead of 3-methyl-4-nitrobenzoic acid, was dissolved in 10 mL ethanol. Palladium on carbon (10% w/w, 0.015 g) was added along with cyclohexene (0.252 mL, 2.49 mmol). The mixture was refluxed for one hour then fresh palladium on carbon and 1,3-cyclohexadiene (0.237 mL, 2.49 mmol) and was refluxed for an additional 6 hours at which time additional palladium on carbon and 1,3-cyclohexadiene were added. After 15 more hours at reflux, the reaction was cooled and filtered over a pad of celite. The solvents were concentrated and the residue purified via silica gel chromatography eluting with 75:25 EtOAc/hexanes. The proper fractions were isolated and concentrated to yield the title product (0.037 g, 0.066 mmol) as a light yellow powder. ¹H NMR (CDCl₃): δ 8.04 (d, 2H), 7.98 (d, 1H), 7.88 (d, 1H), 7.78 (d, 1H), 7.54 (t, 1H), 7.46-7.18 (m, 5H), 7.04 (d, 1H), 6.57 (d, 1H), 5.88 (d, 1H), 5.58 (s, 2H), 3.91 (s, 3H), 3.48 (s, 2H), 3.31 (s, 3H), 2.84 (s, 3H); MS: M+1=563.

Example 24

2-[5-(6-Chloro-pyridine-3-carbonyl)-1-methyl-1H-pyrrol-2-yl]-N-methyl-N-[2,4,6-trichloro-3-(2-methyl-quinolin-8-yloxymethyl)-phenyl]-acetamide (Compound 117)

A. 8-(2,6-Dichloro-3-nitro-benzyloxy)-2-methyl-quinoline (12.72 g, 35.0 mmol), prepared as described above, was suspended in 100 mL concentrated HCl. A solution of stannous chloride (19.98 g, 105.4 mmol) in 50 mL concentrated HCl was prepared and added dropwise into the reaction over a period of 20 minutes. The reaction was stirred for 17 hours then diluted with 1.5 L ice water. This mixture was then basified with 150 mL 50% NaOH. The resulting solid was isolated by filtration, rinsed twice with 50 mL water then once with 50 mL methanol. The solid was air-dried then purified via silica gel chromatography eluting with a gradient of 0-25% EtOAc/methylene chloride. The proper fractions were isolated and concentrated, triturated with 10 mL EtOAc, filtered and dried under vacuum to yield the trichloroaniline (1.236 g, 3.36 mmol) as a tan powder.

B. The product prepared in step A (1.105 g, 3.01 mmol) was suspended in 20 mL triethyl orthoformate with 5 drops trifluoroacetic acid. The mixture was refluxed for 16 hours and was then diluted with 30 mL ethanol and while continuing refluxing was periodically treated with 9~400 mg tablets of sodium borohydride over the next 4 days. The mixture was then concentrated, triturated with water, filtered, and purified via silica gel chromatography eluting with 25% EtOAc/75% hexanes. The proper fractions were concentrated to yield methylated trichloroaniline (0.252 g, 0.660 mmol) as a peach colored powder.

C. 6-Chloronicotinic acid chloride (assume 1.00 mmol) prepared by the methods described above was dissolved in 15 mL methylene chloride. The trichloroaniline prepared in step B (0.191 g, 0.500 mmol) was added to the reaction and the solution was allowed to stir under nitrogen for 3 hours. The reaction was then quenched by addition of ~2 mL of water. The solvents were then removed in vacuo and the residue dissolved in methylene chloride and treated with diisopropylethylamine followed by concentration in vacuo. The residue was purified via silica gel chromatography eluting with 50% EtOAc/50% hexanes. The proper fractions were isolated and concentrated to yield the title product (0.228 g, 0.355 mmol) as a yellow powder. $^1$H NMR (CDCl$_3$): δ 8.73 (d, 1H), 7.99 (m, 2H), 7.62 (s, 1H), 7.48-7.19 (m, 5H), 6.67 (d, 1H), 5.85 (d, 1H), 5.62 (s, 2H), 3.91 (s, 3H), 3.40 (d, 2H), 3.18 (s, 3H), 2.68 (s, 3H); MS: M+1=641.

Example 25

N-[3-(3-Bromo-2-methyl-imidazo[1,2-a]pyridin-8-yloxymethyl)-2,4-dichloro-phenyl]-2-[5-(4-cyano-benzoyl)-1-methyl-1H-pyrrol-2-yl]-N-methyl-acetamide (Compound 102)

[5-(4-Cyano-benzoyl)-1-methyl-1H-pyrrol-2-yl]-acetyl chloride (assume 0.104 mmol), prepared as described above, was dissolved in 5 mL methylene chloride. 8-[(3-N-methylamino-2,6-dichlorobenzyl)oxy]-3-bromo-2-methylimidazo[1,2-a]pyridine (0.024 g, 0.058 mmol), prepared as described above, was added to the reaction mixture along with a small amount of DMAP and the solution was allowed to stir under nitrogen for 18.5 hours. The reaction was then quenched by addition of a ~2 mL of ethanol. The entire crude reaction mixture was subjected to purification by reverse phase column chromatography eluting with a gradient of acetonitrile:water 10-90%. The proper fractions were isolated and the solvents were lyophilized to yield the title product (TFA salt, 0.029 g, 0.037 mmol) as a yellow powder. $^1$H NMR (CDCl$_3$): δ 7.98 (d, 1H), 7.84 (m, 2H), 7.74 (m, 2H), 7.57 (d, 1H), 7.42 (d, 1H), 7.31 (d, 1H), 7.17 (d, 1H), 6.58 (d, 1H), 5.95 (d, 1H), 5.57 (q, 2H), 3.91 (s, 3H), 3.52 (s, 2H), 3.29 (s, 3H), 2.55 (s, 3H); MS: M+1=664.

Example 26

N-[3-(3-Bromo-2-methyl-imidazo[1,2-a]pyridin-8-yloxymethyl)-2,4-dichlorophenyl]-2-[5-(4-methanesulfonyl-benzoyl)-1-methyl-1H-pyrrol-2-yl]-N-methyl-acetamide (Compound 103)

Using the method described above in Example 25, and [5-(4-methanesulfonyl-benzoyl)-1-methyl-1H-pyrrol-2-yl]-acetyl chloride instead of [5-(4-cyano-benzoyl)-1-methyl-1H-pyrrol-2-yl]-acetyl chloride Compound 103 was prepared. M+1=717

Example 27

2-[5-(4-Cyano-benzoyl)-1-methyl-1H-pyrrol-2-yl]-N-[2,4-dichloro-3-(2-methyl-quinolin-8-yloxymethyl)-phenyl]-N-propyl-acetamide (Compound 19)

The [5-(4-cyano-benzoyl)-1-methyl-1H-pyrrol-2-yl]-acetyl chloride, prepared as described above (assume 1.01 mmol), was dissolved in 5 mL methylene chloride. 8-[(3-N-propylamino-2,6-dichlorobenzyl)oxy]-2-methyl quinoline (0.191 g, 0.509 mmol), prepared as described above, was dissolved in 10 mL methylene chloride and then added to the solution of the acid chloride. The reaction mixture was allowed to stir under nitrogen for one hour. The reaction was then quenched by addition of ~2 mL of water. The solvents were evaporated in vacuo and the residue was purified via silica gel chromatography eluting with 50% EtOAc/50% hexanes. The proper fractions were isolated and the organics were removed in vacuo to yield the title product (183 g, 0.293 mmol) as a yellow powder. $^1$H NMR (CDCl$_3$): δ 8.04 (d, 1H), 7.82 (d, 2H), 7.65 (d, 2H), 7.52-7.31 (m, 4H), 7.23 (m, 2H), 6.64 (d, 1H), 5.88 (d, 1H), 5.69 (m, 2H), 4.03 (m, 1H), 3.88 (s, 3H), 3.42 (s, 2H), 3.23 (m, 1H), 2.69 (s, 3H), 1.58 (br m, 2H), 0.92 (t, 3H); MS: M+1=625.

Following the procedure described above for Example 27 and the appropriate reagents, starting materials and purification methods known to those skilled in the art, other compounds of the present invention may be prepared but not limited to:

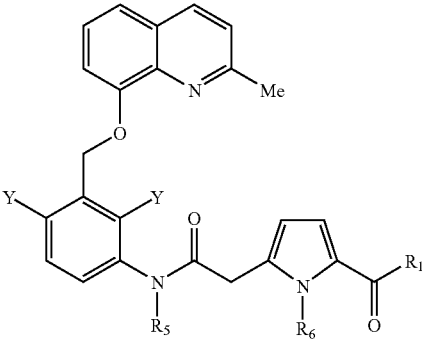

| Cmpd | Y  | R$_5$  | R$_6$ | R$_1$        | MS: (M + 1) |
|------|----|--------|-------|--------------|-------------|
| 17   | Cl | Et     | Me    | (6-Cl)3-pyridyl | 621      |
| 18   | Cl | Et     | Me    | (4-CN)Ph     | 611         |
| 16   | Me | Et     | Me    | (4-CN)Ph     | 571         |
| 21   | Cl | Allyl  | Me    | (4-CN)Ph     | 623         |

Example 28

N-[2,4-Dimethyl-3-(2-methyl-quinolin-8-yloxymethyl)-phenyl]-N-methyl-2-(1-methyl-5-phenyl-1H-pyrrol-2-yl)-acetamide (Compound 97)

A. 4-Oxo-4-phenyl-butyraldehyde (3.24 g, 0.02 mol), prepared by literature methods (Kruse et al (*Heterocycles* 1987, 26, 3141-3151) was dissolved in 20 mL methanol. Ammonium acetate (12.3 g, 0.16 mol) was added and the reaction mixture was heated at reflux for 2 hours. The reaction mixture was evaporated in vacuo and the residue was dissolved in 20 mL of methylene chloride, washed with 30 mL brine, dried over $Na_2SO_4$ and evaporated in vacuo. The product was purified by silica gel chromatography eluting with 10:90 EtOAc:hexanes. The phenyl pyrrolyl product was obtained as a pale pink fluffy solid (2.06 g, 14.4 mmol). $^1$H NMR ($CDCl_3$): δ 7.6 (m, 2H), 7.4 (m, 2H), 7.2 (m, 2H), 6.9 (m, 1H), 6.5 (m, 1H), 6.2 (m, 1H); MS: M+1=144.

B. The product obtained in step A (1.43 g, 10.0 mmol) was added to a slurry of hexane-washed 60% sodium hydride (0.264 g, 11.0 mmol) in 10 mL DMF. The reaction mixture was stirred at room temperature for 45 minutes. Methyl iodide (1.56 g, 11.0 mmol) was added and the reaction mixture was stirred at room temperature for 4 hours. The reaction mixture was poured into 50 mL water and the N-methyl phenyl pyrrolyl was collected by filtration (1.26 g, 8.0 mmol). $^1$H NMR ($CDCl_3$): δ 7.3-7.5 (m, 5H), 6.8 (m, 1H), 6.2 (m, 2H), 3.6 (s, 3H); MS: M+1=158.

C. N,N-Dimethylformamide (0.562 g, 7.7 mmol) was dissolved in 30 mL diethylether and then cooled to 0° C. with an ice-bath. To this solution was added oxalyl chloride (2.93 g, 23.1 mmol) dropwise and the reaction mixture was stirred for 3 hours while letting the temperature of the reaction mixture rise to room temperature. The reaction mixture was decanted and the solid was washed twice with 30 mL diethylether. This intermediate was dried under a stream of nitrogen and immediately carried on to the next reaction.

D. The product obtained in step B (6.5 mmol) was dissolved in 20 mL methylene chloride and the product obtained in step C was added. The reaction mixture was stirred at room temperature for 2 hours. The reaction mixture was washed with 30 mL $NaHCO_3$, then with 30 mL brine, dried over $Na_2SO_4$ and evaporated in vacuo. The pyrrolyl aldehyde was triturated twice with 25 mL hexanes and obtained as an off-white solid (0.96 g, 5.2 mmol). $^1$H NMR ($CDCl_3$): δ 9.6 (s, 1H), 7.3-7.5 (m, 5H), 7.0 (d, 1H), 6.2 (d, 1H), 4.0 (s, 3H); MS: M+1=186.

E. A solution of tosylmethylisocyanide (TosMIC) (1.03 g, 5.3 mmol) in 10 mL dimethoxyethane was added to a well-stirred suspension of 97% potassium t-butoxide (1.16 g, 10.3 mmol) in 20 mL dimethoxyethane cooled to −30° C. After the addition was complete, the temperature was lowered to −45° C. and a solution of the product obtained in step C (0.926 g, 5.0 mmol) was added dropwise to the reaction mixture. The reaction mixture was stirred at −45° C. for 30 minutes, 10 mL of methanol was added and the reaction mixture was heated to reflux for 15 minutes. The solvent was evaporated in vacuo and the residue was treated with 20 mL of water and a few drops of glacial acetic acid and extracted twice with 30 mL of chloroform. The organic extracts were washed with 30 mL $NaHCO_3$, then 30 mL brine, dried over $Na_2SO_4$ and evaporated in vacuo. The resulting cyanomethylpyrrole was purified by silica gel chromatography eluting with 50:50 EtOAc:hexanes (0.687 g, 3.5 mmol). $^1$H NMR ($CDCl_3$): δ 7.3-7.5 (m, 5H), 6.2 (d, 1H), 6.1 (d, 1H), 3.8 (s, 2H), 3.55 (s, 3H); MS: M+1=197.

F. The product obtained in step E (0.589 g, 3.0 mmol) was dissolved in 15 mL of ethanol. Sodium hydroxide (0.132 g, 3.3 mmol) was added and the reaction mixture was heated at reflux for 3 hours. The reaction mixture was evaporated in vacuo and the resulting solid was triturated with water and dried to yield the corresponding carboxylic acid as a white solid (0.610 g, 2.85 mmol).

G. The product obtained in step F (0.215 g, 1.0 mmol) was suspended in 20 mL of methylene chloride. Diisopropylethylamine (0.20 mL, 1.2 mmol) was added and the reaction mixture became homogeneous. HATU (0.53 g, 1.4 mmol) was then added to the reaction mixture followed by the addition of the 8-[3-N-methyl-2,6-dimethylbenzyl)oxy]-2-methyl quinoline (0.306 g, 1.0 mmol) prepared as described above. The reaction was stirred for 16 hours and was then washed sequentially with 20 mL of $NaHCO_3$ and 20 mL of brine. The organic extract was dried over $Na_2SO_4$ and evaporated in vacuo. The product was purified by silica gel chromatography eluting with 50:50 EtOAc:hexanes followed by treatment with excess ethereal HCl to yield the product as the HCl salt, (0.281 g, 0.52 mmol). $^1$H NMR ($CDCl_3$): δ 8.0 (d, 1H), 7.2-7.6 (m, 10H), 6.1 (d, 1H), 5.8 (d, 1H), 5.3 (s, 2H), 3.6 (s, 2H), 3.1 (s, 3H), 2.9 (s, 3H), 2.7 (s, 3H), 2.5 (s, 3H), 2.2 (s, 3H); MS: M+1=504.

Example 29

N-[2,4-Dimethyl-3-(2-methyl-quinolin-8-yloxymethyl)-phenyl]-N-methyl-2-(1-methyl-5-p-tolyl-1H-pyrrol-2-yl)-acetamide (Compound 98)

A. N-methylpyrrole (1.21 g, 15.0 mmol), purchased from Aldrich Chemicals was dissolved in 25 mL THF and then was treated with t-butyl lithium (1.7 M in pentane, 0.96 g, 8.8 mL, 15.0 mmol) at −78° C. The reaction mixture was allowed to warm to room temperature and then was stirred for 30 minutes. The resulting solution was added to a slurry of zinc chloride (2.24 g, 16.5 mmol) in 25 mL THF at room temperature. After stirring for 1 hour, this solution was added with stirring to a mixture of 4-bromotoluene (1.39 g, 8.1 mmol) and 60 mg (0.09 mmol) of $PdCl_2$ (dppf) (dichloropalladium(1,1'-bis(diphenylphosphine) ferrocene) in 10 ml THF. The reaction mixture was stirred for an additional 20 hours at room temperature then quenched by the addition of 10 mL of water. The reaction mixture was made alkaline by the addition of 1 N NaOH and then the organic layer was separated. The organic layer was washed with 20 mL 1N HCl, 20 mL brine dried over $Na_2SO_4$ and evaporated in vacuo. The 2-tolyl pyrrole product was purified by silica gel chromatography eluting with 10:90 EtOAc:hexanes. $^1$H NMR ($CDCl_3$): δ 7.15 (d, 2H), 7.3 (d, 2H), 6.65 (d, 2H), 6.1 (d, 2H), 3.75 (s, 3H), 2.25 (s, 3H); MS: M+1=172.

B. N,N-Dimethylformamide (0.562 g, 7.7 mmol) was dissolved in 30 mL diethylether and then cooled to 0° C. with an ice-bath. To this solution was added oxalyl chloride (2.93 g, 23.1 mmol) dropwise and the reaction mixture was stirred for 3 hours while letting the temperature of the reaction mixture rise to room temperature. The reaction mixture was decanted and the solid was washed twice with 30 mL diethylether. The resulting reagent was dried under a stream of nitrogen and immediately carried on to the next reaction.

C. The product obtained in step B (6.5 mmol) was dissolved in 20 mL methylene chloride and the product obtained in step C was added. The reaction mixture was stirred at room temperature for 2 hours. The reaction mixture was washed with 30 mL NaHCO$_3$, then with 30 mL brine, dried over Na$_2$SO$_4$ and evaporated in vacuo. The pyrrolyl aldehyde product was triturated twice with 25 mL hexanes and obtained as an off-white solid (1.0 g, 4.6 mmol). $^1$H NMR (CDCl$_3$): δ 9.6 (s, 1H), 7.3-7.4 (m, 4H), 6.9 (d, 2H), 6.2 (d, 2H), 3.9 (s, 3H), 2.3 (s, 3H); MS: M+1=200.

D. A solution of tosylmethylisocyanide (TosMIC) (1.03 g, 5.3 mmol) in 10 mL dimethoxyethane was added to a well-stirred suspension of 97% potassium t-butoxide (1.16 g, 10.3 mmol) in 20 mL dimethoxyethane cooled to −30° C. After the addition was complete, the temperature was lowered to −45° C. and a solution of the product obtained in step C (0.996 g, 5.0 mmol) was added dropwise to the reaction mixture. The reaction mixture was stirred at −45° C. for 30 minutes, 10 mL of methanol was added and the reaction mixture was heated to reflux for 15 minutes. The solvent was evaporated in vacuo and the residue was treated with 20 mL of water and a few drops of glacial acetic acid and extracted twice with 30 mL of chloroform. The organic extracts were washed with 30 mL NaHCO$_3$, then 30 mL brine, dried over Na$_2$SO$_4$ and evaporated in vacuo. The cyanomethyl pyrrole product was purified by silica gel chromatography eluting with 50:50 EtOAc:hexanes (0.720 g, 3.4 mmol). $^1$H NMR (CDCl$_3$): δ 7.2-7.3 (m, 4H), 6.2 (d, 2H), 6.0 (d, 2H), 3.8 (s, 2H), 3.5 (s, 3H), 2.3 (s, 3H); MS: M+1=211.

E. The product obtained in step E (0.630 g, 3.0 mmol) was dissolved in 15 mL of ethanol. Sodium hydroxide (0.132 g, 3.3 mmol) was added and the reaction mixture was heated at reflux for 3 hours. The reaction mixture was evaporated in vacuo and the resulting solid was triturated with water and dried to yield the corresponding carboxylic acid as a white solid (0.653 g, 2.85 mmol).

F. The product obtained in step F (0.229 g, 1.0 mmol) was suspended in 20 mL of methylene chloride. Diisopropylethylamine (0.20 mL, 1.2 mmol) was added and the reaction mixture became homogeneous. HATU (0.53 g, 1.4 mmol) was then added to the reaction mixture followed by the addition of 8-[3-N-methylamino-2,6-dimethylbenzyl)oxy]-2-methyl quinoline (0.306 g, 1.0 mmol) prepared as described above. The reaction was stirred for 16 hours and was then washed sequentially with 20 mL of NaHCO$_3$ and 20 mL of brine. The organic extract was dried over Na$_2$SO$_4$ and evaporated in vacuo. The product was purified by silica gel chromatography eluting with 50:50 EtOAc:hexanes followed by treatment with excess ethereal HCl to yield the title product as an HCl salt, (0.264 g, 0.51 mmol). $^1$H NMR (CDCl$_3$): δ 8.05 (d, 1H), 7.0-7.4 (m, 10H), 6.1 (d, 2H), 5.8 (d, 2H), 5.3 (s, 2H), 3.4 (m, 5H), 3.1 (s, 3H), 2.7 (s, 3H), 2.55 (s, 3H), 2.4 (s, 3H), 2.3 (s, 3H); MS: M+1=518.

Example 30

N-[2,4-Dimethyl-3-(2-methyl-quinolin-8-yloxymethyl)-phenyl]-2-[5-(4-methoxy-phenyl)-1-methyl-1H-pyrrol-2-yl]-N-methyl-acetamide (Compound 96)

Using the procedure of Example 29 and 4-bromoanisole instead of 4-bromotoluene in step A, the title compound was prepared. $^1$H NMR (CDCl$_3$): δ 8.05 (d, 1H), 7.2-7.4 (m, 8H), 6.8 (d, 2H), 6.1 (d, 2H), 5.8 (d, 2H), 5.3 (s, 2H), 3.8 (s, 3H), 3.45 (m, 5H), 3.3 (s, 3H), 2.7 (s, 3H), 2.5 (s, 3H), 2.3 (s, 3H); MS: M+1=534.

Example 31

2-(5-Benzoyl-thiophen-2-yl)-N-[2,4-dichloro-3-(2-methyl-quinolin-8-yloxymethyl)-phenyl]-N-methyl-acetamide (Compound 109)

A. Ethyl-2-thiopheneacetate (3.8 mL, 25.3 mmol) and benzoyl chloride (3.0 mL, 25.8 mmol) were dissolved in 20 mL benzene and kept under nitrogen. A solution of tin(IV) chloride (3.0 mL, 25.6 mmol) in 5 mL benzene was prepared and dripped into the reaction over a period of 30 minutes. The reaction was allowed to stir for 16 hours and was then quenched by addition of ice. The reaction was diluted with 50 mL benzene and very carefully washed with 100 mL saturated NaHCO$_3$. The mixture was then filtered over a pad of celite and the organic filtrate was washed twice more with 100 mL saturated NaHCO$_3$, then once with 100 mL brine. The organics were dried with Na$_2$SO$_4$ and concentrated in vacuo. The residue was purified via silica gel chromatography eluting with 25% EtOAc/75% hexanes. The proper fractions were isolated and concentrated to yield the acylated thophene acetate product (5.70 g, 20.8 mmol) as a red oil.

B. The product obtained in step A (2.74 g, 9.99 mmol) was dissolved in 60 mL 5:1 THF:water. Lithium hydroxide monohydrate (0.420 g, 10.0 mmol) was then added to the reaction and was stirred for 18.5 hours. The reaction was then concentrated in vacuo to remove the organics. Water (100 mL) was added to the residue and the solution was filtered over a pad of celite. The filtrate was treated with excess 1N HCl. The resulting solid was filtered off, rinsed with water, and dried under vacuum at 50° C. to yield the corresponding carboxylic acid (2.022 g, 8.21 mmol) as a yellow-tan powder.

C. The product obtained in step B (0.246 g, 1.00 mmol) was dissolved in 15 mL methylene chloride. One drop of DMF was added and the reaction was cooled on an ice bath under an argon atmosphere. Oxalyl chloride (0.26 mL, 3.0 mmol) was added and the reaction was allowed to stir for 2 hours. The organics were then evaporated under a stream of argon while still on the ice bath. The resulting residue was dried under vacuum and carried on as-is as soon as possible.

D. The product obtained in step C (assume 1.00 mmol) was dissolved in 15 mL methylene chloride. 8-[3-N-methylamino-2,6-dichlorobenzyl)oxy]-2-methyl quinoline (0.182 g, 0.524 mmol), prepared as described above, was added to the reaction and the solution was allowed to stir under nitrogen for 2.5 hours. The reaction was then quenched by addition of ~2 mL of water. The solvents were then removed in vacuo and the residue dissolved in methylene chloride and treated with diisopropylethylamine followed by evaporation of the solvents in vacuo. The residue was purified via silica gel chromatography eluting with 70% EtOAc/30% hexanes. The proper fractions were isolated and the organics were removed in vacuo to yield the title product (0.231 g, 0.401 mmol) as a rust orange powder. $^1$H NMR (CDCl$_3$): δ 8.03 (d, 1H), 7.84 (d, 2H), 7.62-7.34 (m, 8H), 7.33-7.22 (m, 2H), 6.86 (d, 1H), 5.71 (s, 2H), 3.59 (s, 2H), 3.25 (s, 3H), 2.71 (s, 3H); MS: M+1=575.

Example 32

2-(5-Benzoyl-thiophen-2-yl)-N-[2,4-dimethyl-3-(2-methyl-quinolin-8-yloxymethyl)-phenyl]-N-methyl-acetamide (Compound 108)

Using the procedure of Example 31 and 8-[3-N-methylamino-2,6-dimethylbenzyl)oxy]-2-methyl quinoline instead of 8-[3-N-methylamino-2,6-dichlorobenzyl)oxy]-2-methyl quinoline in step D, the title compound was prepared. MS: M+1=436.

Example 33

N-[2,4-Dimethyl-3-(2-methyl-quinolin-8-yloxymethyl)-phenyl]-3-[5-(4-methoxy-benzoyl)-1-methyl-1H-pyrrol-2-yl]-N-methyl-propionamide (Compound 106)

A. 2-Thiophenepropionic acid (10 g, 64 mmol) was dissolved in 50 mL ethanol. Concentrated sulfuric acid (1 mL) was added and the solution was stirred for 66 hours. The solvents were then removed in vacuo and the residue dissolved in 100 mL ethyl ether. The organics were washed twice with 50 mL saturated $NaHCO_3$ and once with 50 mL brine then dried with $Na_2SO_4$. Concentration of the organics in vacuo yielded ethyl-2-thiophenepropionate (10.85 g, 58.9 mmol) as an orange oil.

B. Ethyl-2-thiophenepropionate (4.63 g, 25.1 mmol) and p-anisoyl chloride (3.5 mL, 25.8 mmol) were dissolved in 20 mL benzene and kept under nitrogen. A solution of tin(IV) chloride (3.0 mL, 25.6 mmol) in 5 mL benzene was prepared and dripped into the reaction over a period of 7 minutes. The reaction was allowed to stir for 18.5 hours and was then quenched by addition of ice. The reaction was diluted with 50 mL benzene and very carefully washed with 100 mL saturated $NaHCO_3$. The mixture was then filtered over a pad of celite and the organic filtrate was washed twice more with 100 mL saturated $NaHCO_3$. The organics were dried with $Na_2SO_4$ and concentrated in vacuo. The residue was purified via silica gel chromatography eluting with 25% EtOAc/75% hexanes. The proper fractions were isolated and concentrated to yield the acylated thophene propionate (6.66 g, 20.9 mmol) as a yellow oil.

C. The product obtained in step B (3.18 g, 10.0 mmol) was dissolved in 60 mL 5:1 THF:water. Lithium hydroxide monohydrate (0.426 g, 10.2 mmol) was then added to the reaction and was stirred for 17 hours. The reaction was then concentrated in vacuo until the organics have been removed. Water (100 mL) was added to the residue and the solution was filtered over a pad of celite. The filtrate was treated with excess 1N HCl. The resulting solid was filtered off, rinsed with water, and dried under vacuum at 50° C. to yield the corresponding carboxylic acid (2.695 g, 9.28 mmol) as an off-white powder.

D. The product obtained in step C (0.2.90 g, 1.00 mmol) was dissolved in 15 mL methylene chloride. One drop of DMF was added and the reaction was cooled on an ice bath under an argon atmosphere. Oxalyl chloride (0.26 mL, 3.0 mmol) was added and the reaction was allowed to stir for 30 minutes. The organics were then evaporated under a stream of argon while still on the ice bath. The resulting residue was dried under vacuum and carried on as-is as soon as possible.

E. The product obtained in step D (assume 1.00 mmol) was dissolved in 15 mL methylene chloride. 8-[3-N-methylamino-2,6-dimethylbenzyl)oxy]-2-methyl quinoline (0.161 g, 0.525 mmol), prepared as described above, was added to the reaction and the solution was allowed to stir under nitrogen for 19 hours. The reaction was then quenched by addition of ~2 mL of water. The solvents were then removed in vacuo and the residue dissolved in methylene chloride and treated with diisopropylethylamine followed by evaporation of the solvents in vacuo. The residue was purified via silica gel chromatography eluting with 70% EtOAc/30% hexanes. The proper fractions were isolated and the organics were removed in vacuo to yield the product (0.196 g, 0.339 mmol) as a yellow-orange solid. $^1$H NMR ($CDCl_3$): δ 8.03 (d, 1H), 7.86 (d, 2H), 7.48-7.34 (m, 3H), 7.33-7.18 (m, 2H), 7.14 (d, 1H), 6.98 (m, 3H), 6.83 (d, 1H), 5.38 (s, 2H), 3.88 (s, 3H), 3.23-3.12 (m, 5H), 2.72 (s, 3H), 2.52 (s, 3H), 2.48 (m, 1H), 2.30 (m, 4H); MS: M+1=579.

Following the procedure described above for Example 33 and the appropriate reagents, starting materials and purification methods known to those skilled in the art, other compounds of the present invention may be prepared but not limited to:

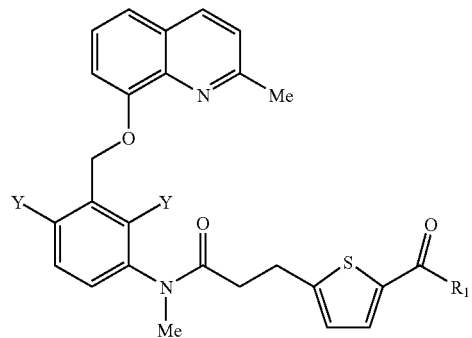

| Cmpd | Y | $R_1$ | MS: (M + 1) |
|---|---|---|---|
| 105 | Cl | Ph | 589 |
| 104 | Me | Ph | 549 |
| 107 | Cl | (4-OMe)Ph | 619 |

Example 34

3-(6-Acetylamino-pyridin-3-yl)-N-{1-[2,4-dimethyl-3-(2-methyl-quinolin-8-yloxymethyl)-phenyl]-pyrrolidin-2-(R)-ylmethyl}-acrylamide (Compound 112)

A. To 211 mg (2.2 mmol) of NaOtBu, 8.1 mg (0.04 mmol) of (t-Bu)$_3$P, and 18.3 mg (0.02 mmol) of (Pd)$_2$(dba)$_3$ was added a suspension containing 713 mg (2.0 mmol) of 8-(3-bromo-2,6-dimethyl-benzyloxy)-2-methyl-quinoline, 342 mg (2.0 mmol) of D-proline tert-butyl ester and 10 mL of toluene at room temperature under $N_2$. The suspension was allowed to heat to 100° C. and allowed to stir overnight at 100° C. Next day the reaction was cooled and quenched by adding 100 mL of ethyl acetate and 100 mL of water. The organic layer was separated, washed with brine (100 mL), and dried over $Na_2SO_4$. The dried organic layer was concentrated under reduced pressure to obtain a crude product. The crude was chromatographed (hexane:ethyl acetate, 7:1) to obtain 170 mg (19.0% yield) of 1-[2,4-dimethyl-3-(2-methyl-quinolin-8-yloxymethyl)-phenyl]-pyrrolidine-2-(R)-carboxylic acid tert-butyl ester as a light yellow foam. $^1$H NMR (300 MHz, $CD_3OD$) δ 8.00 (1H, d, J=8.4 Hz), 7.17-7.40 (4H, m), 6.99 (2H, s), 5.29-5.40 (2H, m), 4.14 (1H, dd, J=5.4, 8.1 Hz), 3.62 (1H, dd, J=7.1, 15.8 Hz), 2.93 (1H, m), 2.73 (3H, s), 2.45 (3H, s), 2.42 (3H, s), 1.90-2.11 (4H, m), 1.26 (9H, s).

B. To 170 mg (0.38 mmol) of 1-[2,4-dimethyl-3-(2-methyl-quinolin-8-yloxymethyl)-phenyl]-pyrrolidine-2-(R)-carboxylic acid tert-butyl ester at ice-bath temperature was added a solution containing 20 mL of trifluoroacetic acid/methylene chloride (1:1). The reaction solution was slowly warmed to room temperature and allowed to stir 2 hr at room temperature. After 2 hr, solvents were removed under reduced pressure. The crude product was then chromatographed (chloroform:methanol, from 9:1 to 4:1) to obtain 71 mg (47.7%) of 1-[2,4-dimethyl-3-(2-methyl-quinolin-8-yloxymethyl)-phenyl]-pyrrolidine-2-(R)-carboxylic acid as a yellow oil. Mass spectrum (ESI) m/z 391 (M+H$^+$).

C. To a solution containing 135 mg (0.35 mmol) of 1-[2,4-dimethyl-3-(2-methyl-quinolin-8-yloxymethyl)-phenyl]-pyrrolidine-2-(R)-carboxylic acid, 58 µL (0.41 mmol) of triethylamine, and 1 mL of dry THF at −23° C. was added a solution containing 49 µL (0.38 mmol) of isobutyl chloroformate and 1 mL of dry THF dropwise. The solution was slowly warmed to 0° C. and allowed to stir 30 min at 0° C. After 30 min, the suspension was filtered and the filtrate was directly added to a solution containing 26 mg (0.69 mmol) of sodium borohydride and 1 mL of water at −10° C. The reaction suspension was slowly warmed to room temperature and allowed to stir 2 hr at room temperature. After 2 hr, to the solution were added 30 mL of ethyl acetate and 30 mL of water. After separating the aqueous layer, the organic layer was washed with brine (30 mL), dried over Na$_2$SO$_4$, and concentrated under reduced pressure. The crude product was chromatographed (hexane:ethyl acetate, 2:1) to obtain 65 mg (50.0% yield) of {1-[2,4-dimethyl-3-(2-methyl-quinolin-8-yloxymethyl)-phenyl]-pyrrolidin-2-(R)-yl}-methanol as a white foam. $^1$H NMR (300 MHz CD$_3$OD) δ 8.14 (1H, d, J=8.4 Hz), 7.34-7.50 (4H, m), 7.15 (1H, d, J=8.2 Hz), 7.03 (1H, d, J=8.2 Hz), 5.27 (2H, s), 3.24-3.68 (5H, m), 2.64 (3H, s), 2.36 (6H, s), 2.15 (1H, m), 1.81-1.97 (3H, m); Mass spectrum (ESI) m/z 377 (M+H$^+$).

D. To 55 mg (0.146 mmol) of {1-[2,4-dimethyl-3-(2-methyl-quinolin-8-yloxymethyl)-phenyl]-pyrrolidin-2-(R)-yl}-methanol and 22 mg (0.146 mmol) of phthalimide in 2 mL of dry benzene at ice-bath temperature under N$_2$ were added 54 µL (0.219 mmol) of (n-Bu)$_3$P, followed by 38 mg (0.219 mmol) of N,N,N',N'-tetramethylazodicarboxamide. The reaction mixture was slowly warmed to room temperature and allowed to stir 5 days. After 5 days, the crude was concentrated and the concentrated sample was chromatographed (hexane:ethyl acetate, from 4:1 to 2:1) to obtain 60 mg (81.1%) of 2-{1-[2,4-dimethyl-3-(2-methyl-quinolin-8-yloxymethyl)-phenyl]-pyrrolidin-2-(R)-ylmethyl}-isoindole-1,3-dione as a light yellow foam. Mass spectrum (ESI) m/z 506 (M+H$^+$).

E. To 50 mg (0.099 mmol) of 2-{1-[2,4-dimethyl-3-(2-methyl-quinolin-8-yloxymethyl)-phenyl]-pyrrolidin-2-(R)-ylmethyl}-isoindole-1,3-dione in 3 mL of dry ethanol at room temperature under N$_2$ was added 20 µL (0.751 mmol) of H$_2$NNH$_2$ dropwise. The reaction solution was allowed to stir overnight at room temperature. Next day, precipitates were filtered and the precipitates were washed with ethanol. The combined filtrates were concentrated under reduced pressure. The concentrated crude was chromatographed (chloroform:methanol, 9:1) to obtain 30 mg (81.1%) of a clear oil as a primary amine.

F. To a solution containing 30 mg (0.080 mmol) of the amine, 17 mg (0.080 mmol) of 3-(6-acetylamino-pyridin-3-yl)-acrylic acid, and 2 mL of dry methylene chloride were added 17 mg (0.120 mmol) of 1-(3-dimethylamino-propyl)-3-ethylcarbodiimide hydrochloride, and 42 µL (0.240 mmol) of diisopropylethylamine at room temperature under N$_2$. The suspension was allowed to stir overnight at room temperature. Next day, the reaction crude was concentrated and the concentrated crude was chromatographed (from hexane:ethyl acetate, 1:8 to chloroform:methanol, 9:1) to obtain 21 mg (46.7%) of the title compound as a white foam. $^1$H NMR (300 MHz, CD$_3$OD) δ 8.37 (1H, d, J=2.1 Hz), 8.15 (1H, d, J=8.5 Hz), 7.89 (1H, dd, J=2.4, 8.8 Hz), 7.33-7.51 (6H, m), 7.18 (1H, d, J=8.2 Hz), 7.02 (1H, d, J=8.2 Hz), 6.53 (1H, d, J=15.8 Hz), 5.27 (2H, s), 3.82 (1H, m), 3.11-3.51 (4H, m), 2.71 (1H, m), 2.59 (3H, s), 2.42 (3H, s), 2.30 (3H, s), 2.15 (3H, s), 1.67-2.22 (3H, m); Mass spectrum (ESI) m/z 564 (M+H$^+$).

Following the procedure described above for Example 34 and the appropriate reagents, starting materials and purification methods known to those skilled in the art, other compounds of the present invention may be prepared but not limited to:

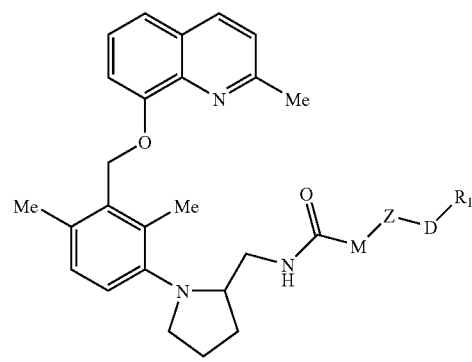

| Cmpd | M | Z | D | R$_1$ | Configuration | MS: (M + 1) |
|---|---|---|---|---|---|---|
| 112 | —CH═CH— | ![pyridine] | —NH—C(O)— | Me | S | 564 |
| 113 | —CH$_2$— | ![Me-pyrrole] | —C(O)— | (4-CN)Ph | S | 626 |

-continued

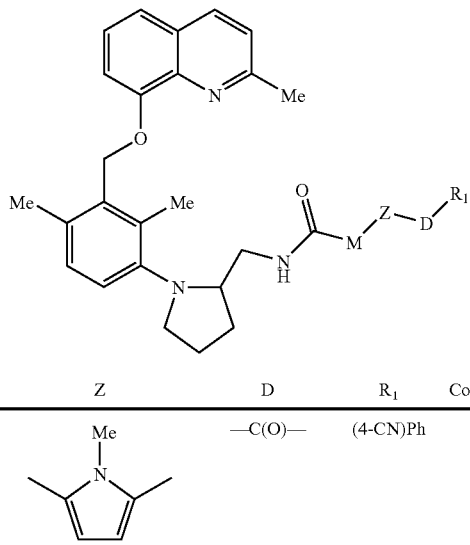

| Cmpd | M | Z | D | R₁ | Configuration | MS: (M + 1) |
|---|---|---|---|---|---|---|
| 114 | —CH₂CH₂— | Me-N(2,5-dimethylpyrrole) | —C(O)— | (4-CN)Ph | S | 640 |

Example 35

2-[4-(4-Cyano-benzoyl)-thiophen-2-yl]-N-[2,4-dichloro-3-(2-methyl-quinolin-8-yloxymethyl)-phenyl]-N-methyl-acetamide (Compound 115)

A. A solution of ethyl-2-thiopheneacetate (2.2 mL, 14.7 mmol) and 4-cyanobenzoyl chloride (2.455 g, 14.8 mmol) in 20 mL methylene chloride was stirred under a nitrogen atmosphere. Tin(IV) chloride (1.90 mL, 16.2 mmol) was added dropwise. After 63 hours the reaction mixture was diluted with 80 mL DCM and washed twice with 50 mL water then once with 50 mL brine. The resulting organics were dried with MgSO₄ and filtered. The residue was chromatographed over silica gel eluting with a gradient of 20% to 35% ethyl acetate/hexanes. The proper fractions were isolated and evaporated in vacuo to yield the product (0.122 g, 0.4 mmol) as a red solid.

B. The ester from the previous reaction (0.120 g, 0.40 mmol) was dissolved in 5 mL EtOH with stirring. The solution was heated to reflux and aqueous NaOH (1 M, 0.40 mL, 0.40 mmol) was added dropwise over 9 minutes. After an additional 1 hour of heating the reaction was cooled and the solvents evaporated in vacuo. The residue was dissolved in 5 mL water and filtered over a pad of celite. The filtrate was acidified with 1 mL 2N HCl. The resulting precipitate was filtered off and rinsed with water and dried under vacuum to yield the product (0.089 g, 0.33 mmol) as a burgundy powder.

C. The acid from the previous reaction (0.027 g, 0.10 mmol) was dissolved in 5 mL DCM along with one drop of DMF and kept under a nitrogen atmosphere. The reaction was cooled on an ice bath and to it was added oxalyl chloride (0.026 mL, 0.30 mmol). The reaction was allowed to stir and then was evaporated under a stream of nitrogen while still on the ice bath. The residue was briefly dried under vacuum and carried on as-is as soon as possible.

D. The acid chloride from the previous reaction (assume 0.10 mmol) was cooled on an ice bath then dissolved in 5 mL DCM with stirring. The dichloroaniline (0.018 g, 0.052 mmol) was added to the solution of the acid chloride followed by a few mgs of DMAP. After 14 hours the reaction was quenched by addition of MeOH. Evaporation of the crude reaction mixture in vacuo gave a residue that was purified twice by reverse phase prep HPLC to give the title product as its TFA salt (0.004 g, 0.006 mmol) as a yellow solid. 1H NMR (CDCl₃): 8.57 (d, 1H), 7.90 (d, 2H), 7.78 (m, 3H), 7.63 (m, 2H), 7.52 (m, 2H), 7.41 (m, 2H), 7.03 (d, 1H), 5.61 (m, 2H), 3.78 (d, 2H), 3.29 (s, 3H), 2.94 (s, 3H); MS: M+1=600.

BIOLOGICAL EXAMPLES

Bradykinin $B_2$ ($BK_2$) receptor binding affinity for the compounds of the present invention were determined according to the following procedures and the indicated results were obtained.

Example 1

Bradykinin $B_2$ ($BK_2$) Receptor Binding Assay

Cell membranes of CHO-K1 cells transfected with human $B_2$ bradykinin receptors (CH)-h$B_2$) were purchased from Receptor Biology, Inc. (Baltimore, Md.). 5.54 mg/mL of membrane protein suspended in 10 mM TRIS-HC pH 7.2, 2 mM EDTA, 10% sucrose.

Incubation for 60 min at 25° C. was performed in a total volume of 1 mL and contained, unless stated differently, 50 mM HEPES, pH 7.2, 5 mM MgCl₂, 0.02 mg/mL 1.10-phenathroline (Sigma, P-9375), 0.25 mg/mL pefebloc SC (Boerhringer, 1429876), 30 μg/mL membrane protein and ~0.25 nM [³HNPC17731 (NEN, Boston). Samples were harvested on a Brandel Cell Harvester on to Wallac filtermat B sheets (96 sample format), and washed three times with 2 mL cold HEPES-buffer (10 mM, pH 7.5), and dried in a microwave oven. To each sample area 2×40 μL of Betaplate Scint scintillation fluid (LKB) was added and the radioactivity quantified on a LKB (Wallac) 1205 BetaPlate liquid scintillation counter.

The data were used to calculate either the % inhibition compared to control binding (when only a single concentration of test compound was evaluated) or a Ki value (when a range of concentrations were tested). Background was subtracted from mean cpm values and % inhibition was calculated as: [(total dpm-test compound dpm)/(total dpm-nonspecific dpm)]×100. Kd and Ki values were calculated using GraphPad PRISM data analysis program.

Example 2

[$^{35}$S]GTPγS Binding Assay in CHO-hB2 Cell Membranes

CHO-hB2 cell membranes were purchased from Receptor Biology, Inc. (Baltimore, Md.). 10 mg/mL of membrane protein was suspended in 10 mM TRIS-HC pH 7.2, 2 mM EDTA, 10% sucrose.

Membranes were added into 15 mL ice cold binding assay buffer. The assay buffer contained 50 mM HEPES, pH 7.6, 5 mM MgCl$_2$, 100 mM NaCl, 1 mM DTT and 1 mM EDTA. The membrane suspension was homogenized twice with a Polytron and centrifuged at 3000 rpm for 10 min. The supernatant was then centrifuged at 18,000 rpm for 20 min. The pellet was saved in a tube and resuspended.

The pellet membranes (40 μg/mL) were preincubated with SPA (scintillation proximity assay) beads (20 mg/mL) at 25C.° for 45 min in the assay buffer. The SPA beads (5 mg/mL) coupled with membranes (10 μg/mL) were then incubated with 0.5 nM [$^3$S]GTPγS in the same HEPES buffer containing 50 μM GDP in total volume of 200 μL. Bradykinin was used to stimulate [$^{35}$S]GTPγS binding. Varying concentrations of drugs were incubated with bradykinin to inhibit bradykinin-stimulated [$^{35}$S]GTPγS binding. The basal binding was tested in the absence of bradykinin and no specific binding was tested in the present 10 μM unlabeled GTPγS. The radioactivity was quantified on a Packard Top Count, and calculated.

% of Basal=(stimulated binding−non specific binding)/(basal binding−non specific binding)×100.

Biological activity measured for select compounds of the present invention are listed in Table 1 below, including bradykinin B$_2$ receptor binding (K$_i$) and functional activity, as determined using the procedures outlined above.

TABLE 1

Bradykinin Receptor Binding and Functional Activity

| Cmpd | B$_2$K$_i$ (nM) | Functional Activity (% Basal) |
|---|---|---|
| 1 | 2910 | |
| 2 | 518 | |
| 3 | 532 | |
| 4 | 1350 | Antagonist (24) |
| 5 | 71 | Antagonist (61) |
| 6 | 41 | |
| 7 | 48 | |
| 8 | 13 | Antagonist (40) |
| 9 | 27 | No effect (1) |
| 10 | 29 | No effect (1) |
| 11 | 48 | No effect (1) |
| 12 | 54 | No effect (1) |
| 13 | 44 | No effect (1) |
| 14 | 6760 | |
| 15 | 6170 | Weak antagonist |
| 16 | 132 | No effect (1) |
| 17 | 342 | No effect (1) |
| 18 | 55 | No effect (1) |
| 19 | 3890 | |
| 21 | 514 | |
| 23 | 5430 | |
| 24 | 5350 | |
| 25 | 4180 | |
| 26 | 4050 | |
| 27 | 3800 | |
| 28 | 2370 | |
| 29 | 2290 | |
| 30 | 1790 | |
| 31 | 1710 | |
| 32 | 1530 | |
| 33 | 1390 | |
| 34 | 1150 | |
| 35 | 1050 | |
| 36 | 869 | |
| 37 | 846 | |
| 38 | 807 | |
| 39 | 784 | |
| 40 | 752 | |
| 41 | 704 | |
| 42 | 688 | |
| 43 | 680 | |
| 44 | 643 | |
| 45 | 579 | |
| 46 | 560 | |
| 47 | 515 | |
| 48 | 510 | |
| 49 | 508 | |
| 50 | 583 | |
| 51 | 476 | |
| 52 | 427 | |
| 53 | 393 | |
| 54 | 356 | |
| 55 | 341 | |
| 56 | 406 | |
| 57 | 361 | |
| 58 | 293 | No effect (1) |
| 59 | 291 | No effect (1) |
| 60 | 400 | |
| 61 | 393 | Weak antagonist (12) |
| 62 | 204 | Antagonist (59) |
| 63 | 178 | Antagonist (33) |
| 64 | 161 | Antagonist (45) |
| 65 | 151 | Antagonist (35) |
| 66 | 169 | Antagonist (35) |
| 67 | 194 | Antagonist (55) |
| 68 | 189 | Weak antagonist (4) |
| 69 | 109 | Antagonist (41) |
| 70 | 162 | |
| 71 | 74 | Antagonist (79) |
| 72 | 85 | Antagonist (74) |
| 73 | 64 | Antagonist (78) |
| 74 | 68 | Antagonist (33) |
| 75 | 47 | Antagonist (73) |
| 76 | 41 | Antagonist (79) |
| 77 | 306 | Antagonist (62) |
| 78 | 286 | Antagonist (83) |
| 79 | 69 | Antagonist (100) |
| 80 | 141 | Weak antagonist (12) |
| 81 | 304 | No effect (1) |
| 82 | 450 | Antagonist (50) |
| 83 | 168 | Antagonist (45) |
| 84 | 304 | Antagonist (57) |
| 85 | 15 | Antagonist (65) |
| 86 | 309 | |
| 87 | 143 | |
| 88 | 126 | Antagonist (41 ) |
| 89 | 57 | Antagonist (51) |
| 90 | 46 | Antagonist (50) |
| 91 | 15 | Antagonist (58) |
| 93 | 30 | Antagonist (74) |
| 96 | 2119 | |
| 97 | 7185 | |
| 98 | 3609 | |
| 99 | 1560 | |
| 100 | 1400 | |
| 101 | 19800 | |

TABLE 1-continued

Bradykinin Receptor Binding and Functional Activity

| Cmpd | $B_2K_i$ (nM) | Functional Activity (% Basal) |
|---|---|---|
| 102 | 47.4 | |
| 103 | 68.5 | |
| 104 | 554 | |
| 105 | 882 | |
| 106 | 375 | |
| 107 | 321 | |
| 108 | 90 | |
| 109 | 53 | |
| 112 | 54 | Antagonist (59) |
| 113 | 7900 | |
| 114 | 545 | |
| 115 | 6.4 | |
| 116 | 17600 | |
| 117 | 86.4 | Antagonist (35) |
| 118 | 428 | |
| 119 | 14000 | |
| 120 | 1560 | |
| 121 | 19800 | |

Example 3

Graded Abdominal Irritant Test

The Graded Abdominal Irritant Test (GrAIT) is a modification of the methods described by Koster et al. (Koster R., Anderson M and DeBeer E. J. *Fed. Proc.* 1959, 18, 412). Prior to the test (30 minutes for oral or subcutaneous administration), each animal was administered a known analgesic, a test compound, or vehicle (0.05N HCl) by one of two routes (oral or subcutaneous).

Kaolin (100 mg/kg) was injected intraperitoneally (using a standard 23G needle) at a volume of 10 ml/kg of body weight. Following the administration of the chemical agent, the animals were placed in glass bell jars (approximately 15 cm in diameter with wood chips on the bottom). The animals were observed to determine the number of occurrences of a characteristic behavioral response. A contraction of the abdominal musculature and an elongation of the body, which extends through to the hindlimbs, characterize this response. The responses were counted during the 15-minute time period after the injection of the kaolin. A mechanical counter or a personal computer was used to collect the number of counts per animal, and animals were observed no more than 5 at a time.

The mean number of counts (±SEM) for a group of animals receiving a known analgesic or test compound was compared to the mean for the group of animals which received only vehicle pretreatment (Control group). For each dose, % inhibition of the response was calculated. For each test compound, the $ED_{50}$ value was calculated using a log dose regression analysis program (PharmTools software).

In vivo biological activity was measured for select compounds of the present invention as listed in Table 4 below, using the procedures outlined above.

TABLE 2

GrAIT Results

| Cmpd | % Inhibition | $ED_{50}$ (μmol/Kg, p.o.) |
|---|---|---|
| 76 | 22 po/ 100 sc | |
| 75 | 50 po/ 93.3 sc | |
| 67 | 78 po/ 100 sc | 68.8 |
| 77 | 70 po | 80.9 |
| 74 | −6 po/ 88 sc | |
| 22 | 41 po/ 100 sc | |
| 60 | 44 po | |
| 78 | 82 po | 114.0 |
| 79 | 68 po | 61.3 |
| 8 | −11 po/ 44 sc | |
| 7 | 26 po/ 42 sc | |
| 17 | −1 po/ 47 sc | |
| 16 | 46 po/ 58 sc | |
| 93 | 66.2 po | |
| 91 | 23 po/ 97.4 sc | |
| 90 | 45 po/ 100 sc | |
| 89 | 98 po | 22.5 |
| 88 | −24 po/ 96 sc | |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

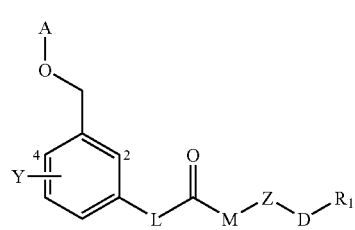

Formula (I)

wherein:

A is

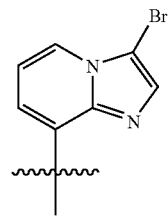

Y is one to three substituents independently selected from the group consisting of halogen and $C_{1-8}$alkyl;

L is:

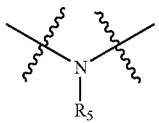

in which $R_5$ is selected from the group consisting of hydrogen, $C_{1-8}$alkyl, $C_{2-8}$alkenyl and aryl($C_{1-8}$)alkyl wherein aryl is optionally substituted with one or more substituents independently selected from the group consisting of $C_{1-8}$alkyl, $C_{1-8}$alkoxy, [($C_{1-8}$)alkyl]$_2$N—, halogen, and cyano;

M is selected from the group consisting of $C_{1-8}$alkylene and $C_{2-8}$alkenylene;

Z is (N—$R_6$)pyrrolylene optionally substituted with one or two $C_{1-4}$alkyl substituents;

$R_6$ is independently selected from the group consisting of $C_{1-8}$alkyl, $C_{2-8}$alkenyl, $C_{3-8}$cycloalkyl($C_{1-8}$)alkyl and aryl($C_{1-8}$)alkyl wherein aryl is optionally substituted with one or more substituents independently selected from the group consisting of $C_{1-8}$alkyl, $C_{1-8}$alkoxy, [($C_{1-8}$s)alkyl]$_2$N—, halogen, and cyano;

D is —C(O)—;

$R_1$ is ($R_7$)phenyl;

$R_7$ is one or two substituents independently selected from the group consisting of hydrogen, $C_{1-8}$alkyl, $C_{2-8}$alkenyl, $C_{2-8}$alkynyl, $C_{3-8}$cycloalkyl, aryl($C_{1-8}$)alkyl, $C_{1-8}$alkoxy, aryloxy, aryl($C_{1-8}$)alkoxy, $C_{1-8}$alkylthio, trifluoro($C_{1-8}$)alkyl, trifluoro($C_{1-8}$)alkoxy, heterocyclyl($C_{1-8}$)alkyl, methylenedioxy, amino, —NH($C_{1-8}$)alkyl, —N[($C_{1-8}$)alkyl]$_2$, —NH(aryl), —N(aryl)$_2$, —NH($C_{1-8}$)alkylaryl, —N[($C_{1-8}$)alkylaryl]$_2$, —CO$_2$($C_{1-8}$)alkyl, —CO$_2$(aryl), —C(O)NH$_2$, —C(O)NH($C_{1-8}$)alkyl, —C(O)N[($C_{1-8}$)alkyl]$_2$, —NHC(O)($C_{1-8}$)alkyl, ($C_{1-8}$alkyl)$_2$—N—($C_{1-8}$)alkyl, S(O)($C_{1-8}$)alkyl, —SO$_2$($C_{1-8}$)alkyl, —SO$_2$NH$_2$, —SO$_2$NH($C_{1-8}$)alkyl, —SO$_2$N[($C_{1-8}$)alkyl]$_2$, —C(O)($C_{1-8}$)alkyl, —C(O)aryl, —C(O)($C_{1-8}$)alkylaryl, halogen, hydroxy, cyano, nitro, phenyl, a 5-membered monocyclic aromatic ring containing one O, S, or N atom and up to three additional N atoms, a 6-membered monocyclic aromatic ring containing at least one N atom and up to two additional N atoms, and a partially saturated or unsaturated 5- or 6-membered monocyclic ring having one O, S or N atom which optionally contains up to one additional O, S or N atom;

and pharmaceutically acceptable enantiomers, diastereomers and salts thereof.

2. A compound of claim 1 wherein M is selected from the group consisting of —CH$_2$CH$_2$— and —CH$_2$—.

3. A compound of claim 1 wherein $R_6$ is independently selected from the group consisting of hydrogen, methyl, ethyl and cyclopropyl-CH$_2$—.

4. A compound of claim 1 wherein $R_7$ is selected from the group consisting of $C_{1-8}$alkyl, $C_{1-8}$alkoxy, $C_{1-8}$thioalkyl, trifluoro($C_{1-8}$)alkyl, heterocyclyl($C_{1-8}$)alkyl, amino, —NH($C_{1-8}$)alkyl, —N[($C_{1-8}$)alkyl]$_2$, —NHC(O)($C_{1-8}$)alkyl, —C(O)NH($C_{1-8}$)alkyl, —C(O)N[($C_{1-8}$)alkyl]$_2$, ($C_{1-8}$alkyl)$_2$—N—($C_{1-8}$)alkyl, —S(O)($C_{1-8}$)alkyl, —SO$_2$($C_{1-8}$)alkyl, —SO$_2$NH$_2$, —CO$_2$($C_{1-8}$)alkyl, halogen, cyano and nitro.

5. A pharmaceutical composition comprising a compound of claim 1 and a pharmaceutically accepted carrier.

6. A method of treating pain comprising administering to the subject a compound of Formula (I):

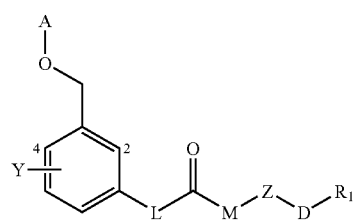

Formula (I)

wherein:

A is

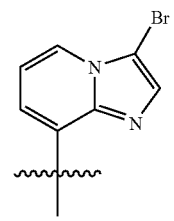

Y is one to three substituents independently selected from the group consisting of halogen and $C_{1-8}$alkyl;

L is:

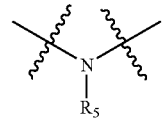

in which $R_5$ is selected from the group consisting of hydrogen, $C_{1-8}$alkyl, $C_{2-8}$alkenyl and aryl($C_{1-8}$)alkyl wherein aryl is optionally substituted with one or more substituents independently selected from the group consisting of $C_{1-8}$alkyl, $C_{1-8}$alkoxy, [($C_{1-8}$)alkyl]$_2$N—, halogen, and cyano;

M is selected from the group consisting of $C_{1-8}$alkylene and $C_{2-8}$alkenylene;

Z is (N—$R_6$)pyrrolylene $R_6$ is independently selected from the group consisting of $C_{1-8}$alkyl, $C_{2-8}$alkenyl, $C_{3-8}$cycloalkyl($C_{1-8}$)alkyl and aryl($C_{1-8}$)alkyl wherein aryl is optionally substituted with one or more substituents independently selected from the group consisting of $C_{1-8}$alkyl, $C_{1-8}$alkoxy, [($C_{1-8}$)alkyl]$_2$N—, halogen, and cyano;

D is —C(O)—, $R_1$ is ($R_7$)phenyl;

$R_7$ is one or two substituents independently selected from the group consisting of hydrogen, $C_{1-8}$alkyl, $C_{1-8}$alkenyl, $C_{1-8}$alkynyl, $C_{3-8}$cycloalkyl, aryl($C_{1-8}$)alkyl, $C_{1-8}$alkoxy, aryloxy, aryl($C_{1-8}$)alkoxy, $C_{1-8}$alkylthio, trifluoro($C_{1-8}$)alkyl, trifluoro($C_{1-8}$)alkoxy, heterocyclyl($C_{1-8}$)alkyl, methylenedioxy, amino, —NH($C_{1-8}$)alkyl, —N[($C_{1-8}$)alkyl]$_2$, —NH(aryl), —N(aryl)$_2$, —NH ($C_{1-8}$)alkylaryl, —N[($C_{1-8}$)alkylaryl]$_2$, —CO$_2$($C_{1-8}$)alkyl, —CO$_2$(aryl), —C(O)NH$_2$, —C(O)NH($C_{1-8}$)alkyl, —C(O)N[($C_{1-8}$)alkyl]$_2$, —NHC(O)($C_{1-8}$)alkyl, ($C_{1-8}$alkyl)$_2$—N—($C_{1-8}$)alkyl, S(O)($C_{1-8}$)alkyl, —SO$_2$($C_{1-8}$)alkyl, —SO$_2$NH$_2$, —SO$_2$NH($C_{1-8}$)alkyl, —SO$_2$N[($C_{1-8}$)alkyl]$_2$, —C(O)($C_{1-8}$)alkyl, —C(O)aryl, —C(O)($C_{1-8}$)alkylaryl, halogen, hydroxy, cyano, nitro, phenyl, a 5-membered monocyclic aromatic ring containing one O, S, or N atom and up to three additional N atoms, a 6-membered monocyclic aromatic ring containing at least one N atom and up to two additional N atoms, and a partially saturated or unsaturated 5- or 6-membered monocyclic ring having one O, S or N atom which optionally contains up to one additional O, S or N atom;

and pharmaceutically acceptable enantiomers, diastereomers and salts thereof.

7. A method of treating pain comprising administering to the subject a compound of claim 1.

8. A method of treating comprising administering to the subject a compound of claim 1 wherein M is selected from the group consisting of —CH$_2$CH$_2$— and —CH$_2$—.

9. A method of treating comprising administering to the subject a compound of claim 1 wherein R$_6$ is independently selected from the group consisting of hydrogen, methyl, ethyl and cyclopropyl-CH$_2$—.

10. A method of treating pain comprising administering to the subject a compound of claim 1 wherein R$_7$ is selected from the group consisting of C$_{1-8}$alkyl, C$_{1-8}$alkoxy, C$_{1-8}$thioalkyl, trifluoro(C$_{1-8}$)alkyl, heterocyclyl(C$_{1-8}$)alkyl, amino, —NH(C$_{1-8}$)alkyl, —N[(C$_{1-8}$)alkyl]$_2$, —NHC(O)(C$_{1-8}$)alkyl, —C(O)NH(C$_{1-8}$)alkyl, —C(O)N[(C$_{1-8}$)alkyl]$_2$, (C$_{1-8}$alkyl)$_2$—N—(C$_{1-8}$)alkyl, —S(O)(C$_{1-8}$)alkyl, —SO$_2$(C$_{1-8}$)alkyl, —SO$_2$NH$_2$, —CO$_2$(C$_{1-8}$)alkyl, halogen, cyano and nitro.

* * * * *